US012616679B2

(12) United States Patent
Dykstra et al.

(10) Patent No.: US 12,616,679 B2
(45) Date of Patent: May 5, 2026

(54) LYOPHILIZED COMPOSITION COMPRISING (S)-ISOPROPYL 2-((S)-2-ACETAMIDO-3-(1H-INDOL-3-YL) PROPANAMIDO)-6-DIAZO-5-OXOHEXANOATE FOR SUBCUTANEOUS ADMINISTRATION AND THE USE THEREOF

(71) Applicant: DRACEN PHARMACEUTICALS, INC., Washington, DC (US)

(72) Inventors: Steven Dykstra, Apex, NC (US); Gary Elliot, Windsor, CO (US); Thomas M. Estok, Williamsburg, VA (US); Stuart R. Gallant, Belmont, MA (US); Robert Christian Wild, Murrieta, CA (US); Jianmin Xu, San Diego, CA (US); Henry Acken Havel, Indianapolis, IN (US)

(73) Assignee: DRACEN PHARMACEUTICALS, INC., Washington, DC (US)

( * ) Notice: Subject to any disclaimer, the term of this patent is extended or adjusted under 35 U.S.C. 154(b) by 401 days.

(21) Appl. No.: 18/247,516

(22) PCT Filed: Oct. 1, 2021

(86) PCT No.: PCT/US2021/053159

§ 371 (c)(1),
(2) Date: Mar. 31, 2023

(87) PCT Pub. No.: WO2022/072820

PCT Pub. Date: Apr. 7, 2022

(65) Prior Publication Data

US 2023/0372294 A1 Nov. 23, 2023

Related U.S. Application Data

(60) Provisional application No. 63/086,972, filed on Oct. 2, 2020.

(51) Int. Cl.
*A61K 31/404* (2006.01)
*A61K 9/19* (2006.01)
(Continued)

(52) U.S. Cl.
CPC .............. *A61K 31/404* (2013.01); *A61K 9/19* (2013.01); *A61K 45/06* (2013.01); *A61K 47/10* (2013.01);
(Continued)

(58) Field of Classification Search
CPC ........ A61K 31/404; A61K 9/19; A61K 45/06; A61K 47/10; A61K 47/183; A61K 57/24;
(Continued)

(56) References Cited

U.S. PATENT DOCUMENTS

| | | | |
|---|---|---|---|
| 3,773,919 | A | 11/1973 | Boswell et al. |
| 4,485,045 | A | 11/1984 | Regen |

(Continued)

FOREIGN PATENT DOCUMENTS

| | | | |
|---|---|---|---|
| EP | 0058481 | A1 | 8/1982 |
| EP | 0102324 | A2 | 3/1984 |

(Continued)

OTHER PUBLICATIONS

Challener âFor Lyophilization, Excipients Really Do Matterâ BioPharm International, 2017, 32-35 (Year: 2017).*

(Continued)

*Primary Examiner* — Brandon J Fetterolf
(74) *Attorney, Agent, or Firm* — STERNE, KESSLER, GOLDSTEIN & FOX P.L.L.C.

(57) ABSTRACT

The present disclosure provides lyophilates comprising (S)-isopropyl 2-((S)-2-acetamido-3-(1H-indol-3-yl)propanamido)-6-diazo-5-oxohexanoate: for subcutaneous administration to a subject, and pharmaceutical compositions, pharmaceutical formulations, and uses thereof (Continued)

19 Claims, 1 Drawing Sheet

(51) Int. Cl.

| | |
|---|---|
| ***A61K 45/06*** | (2006.01) |
| ***A61K 47/10*** | (2017.01) |
| ***A61K 47/18*** | (2017.01) |
| ***A61K 47/24*** | (2006.01) |
| ***A61K 47/26*** | (2006.01) |
| *C07K 16/28* | (2006.01) |

(52) U.S. Cl.

CPC ............ *A61K 47/183* (2013.01); *A61K 47/24* (2013.01); *A61K 47/26* (2013.01); *C07K 16/2803* (2013.01); *C07K 16/2818* (2013.01); *C07K 16/2827* (2013.01)

(58) Field of Classification Search

CPC .. A61K 47/26; A61K 9/0021; A61K 31/4172; C07C 245/18; C08F 26/10

See application file for complete search history.

(56) References Cited

U.S. PATENT DOCUMENTS

| | | | |
|---|---|---|---|
| 4,544,545 | A | 10/1985 | Ryan et al. |
| 5,328,470 | A | 7/1994 | Nabel et al. |
| 6,362,226 | B2 | 3/2002 | Phillips, III et al. |
| 10,336,778 | B2 | 7/2019 | Slusher et al. |
| 10,568,868 | B2 | 2/2020 | Slusher et al. |
| 10,738,066 | B2 | 8/2020 | Slusher et al. |
| 10,842,763 | B2 | 11/2020 | Slusher et al. |
| 10,954,257 | B2 | 3/2021 | Slusher et al. |
| 11,110,104 | B2 | 9/2021 | Slusher et al. |
| 11,185,534 | B2 | 11/2021 | Slusher et al. |
| 2004/0029801 | A1 | 2/2004 | Zhong et al. |
| 2006/0035838 | A1 | 2/2006 | Khosla et al. |
| 2006/0276438 | A1 | 12/2006 | Sethuraman et al. |
| 2008/0107624 | A1 | 5/2008 | D'Andrea et al. |
| 2008/0146526 | A1 | 6/2008 | Gallop et al. |
| 2008/0160024 | A1 | 7/2008 | Ware |
| 2009/0042806 | A1 | 2/2009 | Khosla et al. |
| 2009/0062223 | A1 | 3/2009 | Keicher et al. |
| 2009/0169537 | A1 | 7/2009 | Bausch et al. |
| 2010/0069340 | A1 | 3/2010 | Zacharchuk et al. |
| 2013/0289012 | A1 | 10/2013 | Gu et al. |
| 2014/0004081 | A1 | 1/2014 | Cobbold et al. |
| 2014/0065100 | A1 | 3/2014 | Rossignol et al. |
| 2015/0202291 | A1 | 7/2015 | Bosch et al. |
| 2015/0258082 | A1 | 9/2015 | Parlati et al. |
| 2016/0022674 | A1 | 1/2016 | Steggerda et al. |
| 2016/0113925 | A1 | 4/2016 | Shanmugan et al. |
| 2016/0193239 | A1 | 7/2016 | Baylin et al. |
| 2016/0310453 | A1 | 10/2016 | Mathios et al. |
| 2017/0190657 | A1 | 7/2017 | Gallop et al. |
| 2018/0193362 | A1* | 7/2018 | Slusher et al. |
| 2018/0221395 | A1 | 8/2018 | Slusher et al. |
| 2018/0244783 | A1 | 8/2018 | Hoey et al. |
| 2021/0145779 | A1 | 5/2021 | Slusher et al. |
| 2021/0206787 | A1 | 7/2021 | Slusher et al. |
| 2022/0117938 | A1 | 4/2022 | Wild et al. |
| 2022/0332676 | A1 | 10/2022 | Dykstra et al. |
| 2023/0009398 | A1 | 1/2023 | Slusher et al. |

FOREIGN PATENT DOCUMENTS

| | | | |
|---|---|---|---|
| EP | 0123170 | A2 | 10/1984 |
| EP | 0133988 | A2 | 3/1985 |
| WO | WO-2004113363 | A2 | 12/2004 |
| WO | WO-2005068455 | A1 | 7/2005 |
| WO | WO-2005097108 | A1 | 10/2005 |
| WO | WO-2013019058 | A2 | 2/2013 |
| WO | WO-2014138391 | A1 | 9/2014 |
| WO | WO-2014160071 | A1 | 10/2014 |
| WO | WO-2015101957 | A2 | 7/2015 |
| WO | WO-2020167829 | A1 | 8/2020 |
| WO | WO-2020167831 | A1 | 8/2020 |
| WO | WO-2022232565 | A1 | 11/2022 |

OTHER PUBLICATIONS

International Search Report and Written Opinion for International Application No. PCT/US20/14149, U.S. Patent and Trademark Office, Virginia, mailed on Apr. 7, 2020, 19 pages.

Lemberg, K.M., "We're not "DON" Yet: Optimal Dosing and Prodrug Delivery of 6-Diazo-5-oxo-L-norleicine," Mol. Cancer Ther 17(9): 1824-1832, American Association for Cancer Research, United States (2018).

Liwschitz, Y., et al., "Diazo-ketones with potential tumour-inhibitory properties derived from L-aspartic and L-glutamic acids," Journal of the Chemical Society C: Organic 0:223-225, Royal Society of Chemistry, United Kingdom (1971).

Simplicio, A. L., et al., "Prodrugs for amines," Molecules 13(3):519-547, Multidisciplinary Digital Publishing Institute, Switzerland (2008).

Sznol, M., and Chen, L., "Antagonist antibodies to PD-1 and B7-H1 (PD-L1) in the treatment of advanced human cancer," Clin Cancer Res 19(5):1021-1034, American Association for Cancer Research, United States (2013).

Noonan et al. "Phase 1/11 study of marrow infiltrating lymphocytes (Mils) generates measurable myeloma-specific immunity in the autologous stem cell transplant (SCT) setting," Blood 118(21):997, American Society of Hematology, United States (2011).

Leone, R. D., et al., "A2aR antagonists: Next generation checkpoint blockade for cancer immunotherapy," Comput Struct Biotechnol J 13:265-272, Elsevier, Netherlands (2015).

Abdelmalek, M.F., et.al., "Sirolimus Conversion Regimen Versus Continued Calcineurin Inhibitors in Liver Allograft Recipients: a Randomized Trial.," American Journal of Transplantation : Official Journal of the American Society of Transplantation and the American Society of Transplant Surgeons 12(3):694-705, Wiley-blackwell on Behalf of the American Society of Transplant Surgeons and the American Society of Transplantation, United States (Jan. 2012).

Acevedo., et.al., "Synthesis and Analysis of the Sterically Constrained L-glutamine Analogues (3s,4r)-3,4-dimethyl-1-glutamine and (3s,4r)-3,4-dimethyl-1-pyroglutamic Acid," Tetrahedron 57(30):6353-6359, Elsevier Science Ltd (Jul. 2001).

Ahluwalia.,G.S., et.al., "Metabolism and Action of Amino Acid Analog Anti-cancer Agents.," Pharmacology & Therapeutics 46(2):243-271, Pergamon Press, England (1990).

Alt, J., et.al., "Bioanalysis of 6-diazo-5-oxo-1-norleucine in Plasma and Brain by Ultra-performance Liquid Chromatography Mass Spectrometry.," Analytical Biochemistry 474:28-34, Elsevier, United States (Jan. 2015).

Altschul, S.F., et al., "Basic Local Alignment Search Tool," Journal of Molecular Biology 215(3):403-410, Elsevier, England (Oct. 1990).

(56) References Cited

OTHER PUBLICATIONS

Altschul, S.F., et al., "Gapped BLAST and PSI-BLAST: A New Generation of Protein Database Search Programs," Nucleic Acids Research 25(17):3389-3402, Oxford University Press, England (Sep. 1997).
Antinori, A., et.al., "Updated Research Nosology for HIV-associated Neurocognitive Disorders.," Neurology 69(18):1789-1799, Lippincott Williams & Wilkins, United States (Oct. 2007).
Arnold, R., et.al., "Association Between Calcineurin Inhibitor Treatment and Peripheral Nerve Dysfunction in Renal Transplant Recipients. ," American Journal of Transplantation : Official Journal of the American Society of Transplantation and the American Society of Transplant Surgeons 13(9):2426-2432, Wiley-blackwell on Behalf of the American Society of Transplant Surgeons and the American Society of Transplantation, United States (Jul. 2010).
Barclay, R.K., et.al., "Effects of 6-diazo-5-oxol-norleucine and Other Tumor Inhibitors on the Biosynthesis of Nicotinamide Adenine Dinucleotide in Mice.," Cancer research 26(2):282-286, American Association for Cancer Research, United States (Feb. 1966).
Berge, S.M., et al., "Pharmaceutical Salts," Journal of Pharmaceutical Sciences 66(1):1-19, Wiley, United States (Jan. 1977).
Bestard, O., et.al., "Costimulatory Blockade With Mtor Inhibition Abrogates Effector T-cell Responses Allowing Regulatory T-cell Survival in Renal Transplantation.," Transplant International : Official Journal of the European Society for Organ Transplantation 24(5):451-460, Blackwell Pub, England (May 2011).
Borjabad, A., et.al., "Significant Effects of Antiretroviral Therapy on Global Gene Expression in Brain Tissues of Patients With Hiv-1-associated Neurocognitive Disorders.," Plos Pathogens 7(9):e1002213, Public Library of Science, United States (Sep. 2011).
Buzzai, M., et.al., "Systemic Treatment With the Antidiabetic Drug Metformin Selectively Impairs P53-deficient Tumor Cell Growth.," Cancer Research 67(14):6745-6752, American Association for Cancer Research, United States (Jul. 2007).
Cao, X., et.al., "Astrocyte-derived Atp Modulates Depressive-like Behaviors.," Nature Medicine 19(6):773-777, Nature Publishing Company, United States (Jun. 2013).
Carr, E.L., et.al., "Glutamine Uptake and Metabolism are Coordinately Regulated by Erk/mapk During T Lymphocyte Activation.," Journal of Immunology (Baltimore, MD. : 1950) 185(2):1037-1044, American Association of Immunologists, United States (Jul. 2010).
Cervantes-Madrid, D., et al., "Reviving Lonidamine and 6-Diazo-5-oxo-L-norleucine to be used in Combination for Metabolic Cancer Therapy, " BioMed Research International 2015:690492, Hindawi Pub. Co, United States (2015).
Cham, C.M and Gajewski, T.F, "Glucose Availability Regulates IFN-gamma Production and p70S6 Kinase Activation in CD8+ Effector T Cells," Journal of Immunology (Baltimore, MD. : 1950) 174(8):4670-4677, American Association of Immunologists, United States (Apr. 2005).
Cham, C.M., et.al., "Glucose Deprivation Inhibits Multiple Key Gene Expression Events and Effector Functions in Cd8+ T Cells.," European Journal of Immunology 38(9):2438-2450, Wiley-vch, Germany (Sep. 2008).
Chambers, J.W., et al., "Glutamine Metabolism is Essential for Human Cytomegalovirus Infection," Journal of Virology 84(4):1867-1873, American Society For Microbiology, United States (Feb. 2010).
Chang, L., et al., "Persistent Brain Abnormalities in Antiretroviral-naive HIV Patients 3 Months after HAART," Antiviral Therapy 8(1):17-26, International Medical Press, England (Feb. 2003).
Chapman, A.P., "PEGylated Antibodies and Antibody Fragments for Improved Therapy: a Review," Advanced Drug Delivery Reviews 54(4):531-545, Elsevier Science Publishers, Netherlands (Jun. 2002).
Chen, S.H., et al., "Gene Therapy for Brain Tumors: Regression of Experimental Gliomas by Adenovirus-mediated Gene Transfer in Vivo," Proceedings of the National Academy of Sciences 91(8):3054-3057, National Academy of Sciences, United States (Apr. 1994 ).
Cheng, G., et al., "Mitochondria-targeted Drugs Synergize with 2-deoxyglucose to Trigger Breast Cancer Cell Death," Cancer Research 72(10):2634-2644, American Association for Cancer Research, United States (May 2012).
Cheng, G., et al., "Profiling and Targeting of Cellular Bioenergetics: Inhibition of Pancreatic Cancer Cell Proliferation," British Journal of Cancer 111(1):85-93, Nature Publishing Group on behalf of Cancer Research UK, England (Jul. 2014).
Cheong, J.H., et al., "Dual inhibition of tumor energy pathway by 2-Deoxyglucose and Metformin is Effective against a Broad Spectrum of Preclinical Cancer Models," Molecular Cancer Therapeutics 10(12):2350-2362, American Association for Cancer Research, United States (Dec. 2011).
Cinatl, J., et al., "Antiviral Effects of 6-diazo-5-oxo-L-norleucin on Replication of Herpes Simplex Virus Type 1," Antiviral Research 33(3):165-175, Elsevier, Netherlands (Feb. 1997).
Coffey, G.L., et al., "6-diazo-5-oxo-L-norleucine, a New Tumor-inhibitory Substance. I. Biologic Studies," Antibiotics & Chemotherapy 6(8):487-497, Washington Institute of Medicine, United States (Aug. 1956).
Coggin, Jr., J.H. and Martin, W. R., "6-Diazo-5-Oxo-1-Norleucine Inhibition of *Escherichia coli*," Journal of Bacteriology 89(5):1348-1353, American Society For Microbiology, United States (May 1965).
Corry, R.J., et al., "Primarily Vascularized Allografts of Hearts in Mice. The Role of H-2D, H-2K, and Non-H-2 Antigens in Rejection," Transplantation 16(4):343-350, Lippincott Williams & Wilkins, United States (Oct. 1973).
Csibi, A., et al., "The mTORC1 Pathway Stimulates Glutamine Metabolism and Cell Proliferation by Repressing SIRT4," Cell 153(4):840-854, Cell Press, United States (May 2013).
Cui, F., et al., "Overexpression of Cathepsin L is Associated with Gefitinib Resistance in Non-small Cell Lung Cancer," Clinical & Translational Oncology 18(7):722-727, Springer Italia, Italy (Jul. 2016).
Cunningham-Rundles, C., et al., "Biological Activities of Polyethylene-glycol Immunoglobulin Conjugates. Resistance to Enzymatic Degradation," Journal of Immunological Methods 152(2):177-190, Elsevier, Netherlands (Aug. 1992).
Crutchlow, M.F. and Bloom, R.D., "Transplant-Associated Hyperglycemia: A New Look at an Old Problem," Clinical Journal of the American Society of Nephrology 2(2):343-355, American Society of Nephrology, United States (Mar. 2007).
Dickens, A.M., et al., "Cerebrospinal Fluid Metabolomics Implicate Bioenergetic Adaptation as a Neural Mechanism Regulating Shifts in Cognitive States of HIV-infected Patients," AIDS 29(5):559-569, Lippincott Williams & Wilkins, England (Mar. 2015).
Darmaun, D., et al., "Phenylbutyrate-induced Glutamine Depletion in Humans: Effect on Leucine Metabolism," The American Journal of Physiology 274(5pt1):E801-E807, American Physiological Society, United States (May 1998).
Deberardinis, R.J. and Cheng, T., "Q's Next: the Diverse Functions of Glutamine in Metabolism, Cell Biology and Cancer," Oncogene 29(3):313-324, Nature Publishing Group, England (Jan. 2010).
Delgoffe, G.M., et al., "The Mammalian Target of Rapamycin (mTOR) Regulates the Differentiation of Helper T Cells Through the Selective Activation of Signaling by mTORC1 and mTORC2," Nature Immunology 12(4):295-303, Nature America Inc, United States (Apr. 2011).
Delgoffe, G.M., et al., "mTOR Differentially Regulates Effector and Regulatory T Cell Lineage Commitment," Immunity 30(6):832-844, Cell Press, United States (Jun. 2009).
Dewald, H.A.and Alexander M.M., "6-diazo-5-oxo-L-norleucine, a New Tumor-inhibitory Substance. Preparation of L-, D- and Dl-forms," Journal of the American Chemical Society 80(15):3941-3945, (Aug. 1958).
Dion, H.W., et al., "6-Diazo-5-oxo-L-norleucine, A New Tumor-inhibitory Substance. II. Isolation and Characterization," Journal of the American Chemical Society 78(13):3075-3077, (Jul. 1956).
Dolan, D.E. and Gupta, S., "PD-1 Pathway Inhibitors: Changing the Landscape of Cancer Immunotherapy," Cancer Control 21(3):231-237, Sage Publishing, United States (Jul. 2014).

(56) References Cited

OTHER PUBLICATIONS

Dranoff, G., et al., "Combination Chemotherapy in Vitro Exploiting Glutamine Metabolism of Human Glioma and Medulloblastoma," Cancer Research 45(9):4082-4086, American Association for Cancer Research, United States (Sep. 1985).
Dranoff, G., et al., "Influence of Glutamine on the Growth of Human Glioma and Medulloblastoma in Culture," Cancer Research 45(9):4077-4081, American Association for Cancer Research, United States (Sep. 1985).
Eagan, R.T., et al., "Phase II Study on DON in Patients with Previously Treated Advanced Lung Cancer," Cancer Treatment Reports 66(8):1665-1666, National Cancer Institute, United States (Aug. 1982).
Earhart, R.H., et al., "Phase I Trial of 6-diazo-5-oxo-L-norleucine (DON) Administered by 5-day Courses," Cancer Treatment Reports 66(5):1215-1217, National Cancer Institute, United States (May 1982).
Earhart, R.H., et al., "Phase II Trial of 6-diazo-5-oxo-L-norleucine Versus Aclacinomycin-a in Advanced Sarcomas and Mesotheliomas," Investigational New Drugs 8(1):113-119, Springer, United States (Feb. 1990).
Ellis, R., et al., "HIV and Antiretroviral Therapy in the Brain: Neuronal Injury and Repair," Nature Reviews. Neuroscience 8(1):33-44, Nature Pub. Group, England (Jan. 2007).
El-Mir, M.Y., et al., "Dimethylbiguanide Inhibits Cell Respiration via an Indirect Effect Targeted on the Respiratory Chain Complex I," The Journal of Biological Chemistry 275(1):223-228, American Society for Biochemistry and Molecular Biology, United States (Jan. 2000).
Engels, E.A., et al., "Spectrum of Cancer Risk among U.S. Solid Organ Transplant Recipients: the Transplant Cancer Match Study," JAMA 306(17):1891-1901, American Medical Association, United States (Nov. 2011).
Eppstein, D.A., et al., "Biological activity of liposome-encapsulated murine interferon gamma is mediated by a cell membrane receptor," Proceedings of the National Academy of Sciences 82(11):3688-3692, National Academy of Sciences, United States (1985).
Erickson, J.W. and Cerione R.A., "Glutaminase: A Hot Spot for Regulation of Cancer Cell Metabolism?," Oncotarget 1(8):734-740, Impact Journals, United States (Dec. 2010).
Eshleman, J.S., et al., "Inhibition of the Mammalian Target of Rapamycin Sensitizes U87 Xenografts to Fractionated Radiation Therapy," Cancer Research 62(24):7291-7297, American Association for Cancer Research, United States (Dec. 2002).
Everall, I., et al., "Cliniconeuropathologic Correlates of Human Immunodeficiency Virus in the Era of Antiretroviral Therapy," Journal of Neurovirology 15(5-6):360-370, Springer, United States (Sep. 2009).
Franciosi, M., et al., "Metformin Therapy and Risk of Cancer in Patients with Type 2 Diabetes: Systematic Review," PloS one 8(8):e71583, Public Library of Science, United States (Aug. 2013).
Kull, F.C., et al., "Mixtures of Quaternary Ammonium Compounds and Long-chain Fatty Acids as Antifungal Agents," Applied Microbiology 9(6):538-541, American Society For Microbiology, United States (Nov. 1961).
Fogal, V., et al., "Mitochondrial p32 is Upregulated in Myc Expressing Brain Cancers and Mediates Glutamine Addiction," Oncotarget 6(2):1157-1170, Impact Journals, United States (Jan. 2015).
Gelman, B.B., et al., "The National NeuroAIDS Tissue Consortium Brain Gene Array: Two Types of HIV-associated Neurocognitive Impairment," PLoS One 7(9):e46178, Public Library of Science, United States (2012).
Grayzel, A.I., et al., "Suppression of Uric Acid Synthesis in the Gouty Human by the Use of 6-diazo-5-oxo-L-norleucine.," The Journal of Clinical Investigation 39:447-454, American Society for Clinical Investigation, United States (Mar. 1960).
Gross, M.I., et al., "Antitumor Activity of the Glutaminase Inhibitor CB-839 in Triple-Negative Breast Cancer," Molecular Cancer Therapeutics 13(4):890-901, American Association for Cancer Research, United States (Apr. 2014).
Grupp, S.A., et al., "Chimeric Antigen Receptor-Modified T Cells for Acute Lymphoid Leukemia," The New England Journal of Medicine 368(16):1509-1518, Massachusetts Medical Society, United States (Apr. 2013).
Guba, M., et al., "Pro- and Anti-cancer Effects of Immunosuppressive Agents used in Organ Transplantation," Transplantation 77(12):1777-1782, Lippincott Williams & Wilkins, United States (Jun. 2004).
Harding, J.J., et al., "Safety and Tolerability of Increasing Doses of CB-839, a First-in-class, Orally Administered Small Molecule Inhibitor of Glutaminase, in Solid Tumors," Journal of Clinical Oncology 33(15_suppl ):2512, (May 2015).
Harezlak, J., et al., "Persistence of HIV-associated Cognitive Impairment, Inflammation, and Neuronal Injury in Era of Highly Active Antiretroviral Treatment," AIDS 25(5):625-633, Lippincott Williams & Wilkins, England (Mar. 2011).
Hart, R.G., et al., "Neuroprotection Trials in Parkinson's Disease: Systematic Review," Movement Disorders 24(5):647-654, Wiley-Liss, United States (Apr. 2009).
Hausch, F., et al., "Design, Synthesis, and Evaluation of Gluten Peptide Analogs as Selective Inhibitors of Human Tissue Transglutaminase," Chemistry & Biology 10(3):225-231, Elsevier, United States (Mar. 2003).
Heaton, R.K., et al., "HIV-associated Neurocognitive Disorders Before and During the Era of Combination Antiretroviral Therapy: Differences in Rates, Nature, and Predictors," Journal of Neurovirology 17(1):3-16, Springer, United States (Feb. 2011).
Heaton, R.K., et al., "HIV-associated Neurocognitive Disorders Persist in the Era of Potent Antiretroviral Therapy: Charter Study," Neurology 75(23):2087-2096, Lippincott Williams & Wilkins, United States (Dec. 2010).
Henderson, J.M., et al., "Hepatocellular Carcinoma: Mouse Models and the Potential Roles of Proteases," Cancer Letters 387:106-113, Elsevier Science Ireland, Ireland (Feb. 2017).
Hensley, C.T., et al., "Glutamine and Cancer: Cell Biology, Physiology, and Clinical Opportunities," The Journal of Clinical Investigation 123(9):3678-3684, American Society for Clinical Investigation, United States (Sep. 2013).
Hodes, G.E., et al., "Individual Differences in the Peripheral Immune System Promote Resilience Versus Susceptibility to Social Stress," Proceedings of the National Academy of Sciences of the United States of America 111(45):16136-16141, National Academy of Sciences, United States (Nov. 2014).
Hofer, A., et al., "Trypanosoma Brucei CTP Synthetase: a Target for the Treatment of African Sleeping Sickness," Proceedings of the National Academy of Sciences of the United States of America 98(11):6412-6416, National Academy of Sciences, United States (May 2001).
Hollinger, K.R., et al., "Dose-dependent Inhibition of GCPII to Prevent and Treat Cognitive Impairment in the EAE Model of Multiple Sclerosis," Brain Research 1635:105-112, North-Holland Biomedical Press, Netherlands (Mar. 2016).
Hoorn, E.J., et al., "Pathogenesis of Calcineurin Inhibitor-induced Hypertension," Journal of Nephrology 25(3):269-275, Springer, Italy (May-Jun. 2012).
Hu, X., et al., "Genetic Alterations and Oncogenic Pathways Associated with Breast Cancer Subtypes," Molecular Cancer Research 7(4):511-522, American Association for Cancer Research, United States (Apr. 2009).
Hutchinson, J.A., et al., "Peptide Hormones and Lipopeptides: from Self-assembly to Therapeutic Applications," Journal of Peptide Science 23(2):82-94, John Wiley & Sons, England (Feb. 2017).
Hwang, K.J., et al., "Hepatic uptake and degradation of unilamellar sphingomyelin/cholesterol liposomes: a kinetic study," Proceedings of the National Academy of Sciences 77(7):4030-4034, National Academy of Sciences, United States (1980).
International Search Report and Written Opinion for International Application No. PCT/US2016/044767, Korean Intellectual Property Office, Daejeon, Korea, mailed on Oct. 31, 2016, 9 pages.
International Search Report and Written Opinion for International Application No. PCT/US2016/044810, Korean Intellectual Property Office, Daejeon, Korea, mailed on Dec. 5, 2016, 10 pages.

(56) References Cited

OTHER PUBLICATIONS

International Search Report and Written Opinion for International Application No. PCT/US2016/044825, Korean Intellectual Property Office, Daejeon, Korea, mailed on Nov. 4, 2016, 10 pages.
Jacobs, S.R., et al., "Glucose Uptake is Limiting in T Cell Activation and Requires CD28-Mediated Akt-Dependent and Independent Pathways," Journal of Immunology 180(7):4476-4486, American Association of Immunologists, United States (Apr. 2008).
Jones, R.G. and Thompson, C.B., "Revving the Engine: Signal Transduction Fuels T Cell Activation," Immunity 27(2):173-178, Cell Press, United States (Aug. 2007).
Karlin, S. and Altschul, S.E., "Methods for Assessing the Statistical Significance of Molecular Sequence Features by using General Scoring Schemes," Proceedings of the National Academy of Sciences USA 87(6):2264-2268, National Academy of Sciences, United States (Mar. 1990).
Karlin, S, and Altschul, S.F., "Applications and Statistics for Multiple High-scoring Segments in Molecular Sequences," Proceedings of the National Academy of Sciences USA 90(12):5873-5877, National Academy of Sciences, United States (Jun. 1993).
Kaul, M., et al., "HIV-1 Infection and AIDS: Consequences for the Central Nervous System," Cell Death and Differentiation 12 Suppl 1:878-892, Nature Publishing Group, England (Aug. 2005).
Konopleva., et al., "Phase 1 study: Safety and tolerability of increasing doses of cb-839, an orally-administered small molecule inhibitor of glutaminase," In Acute Leukemia, Haematologica (2015).
Kovach, J.S., et al., "Phase I and Pharmacokinetic Studies of DON," Cancer Treatment Reports 65(11-12):1031-1036, National Cancer Institute, United States (Nov.-Dec. 1981).
Krishnan, V., et al., "Molecular Adaptations Underlying Susceptibility and Resistance to Social Defeat in Brain Reward Regions," Cell 131(2):391-404, Cell Press, United States (Oct. 2007).
Lagodzinski, Z., et al., "Effect of FK506 and Cyclosporine on Primary and Secondary Skin Allograft Survival in Mice," Immunology 71(1):148-150, Blackwell Scientific Publications, England (Sep. 1990).
Langer, R., et al., "Biocompatibility of Polymeric Delivery Systems for Macromolecules," Journal of Biomedical Materials Research 15(2):267-277, John Wiley & Sons, Inc., United States (1981).
Le, A., et al., "Glucose-independent Glutamine Metabolism via TCA Cycling for Proliferation and Survival in B Cells," Cell Metabolism 15(1):110-121, Cell Press, United States (Jan. 2012).
Le Maux, P., et al., "Chemical Reactivity of 6-diazo-5-oxo-L-norleucine (DON) Catalyzed by Metalloporphyrins (Fe,Ru)," Tetrahedron 66(25):4462-4468, Elsevier (Jun. 2010).
Lee, M.D., et al., "New Antitumor Antibiotic, LL-D05139 Beta. Fermentation, Isolation, Structure Determination and Biological Activities," The Journal of Antibiotics 40(12):1657-1663, Nature Publishing Group, Japan (Dec. 1987).
Lee, C.F., et al., "Preventing Allograft Rejection by Targeting Immune Metabolism," Cell Reports 13(4):760-770, Cell Press, United States (Oct. 2015).
Lee, Y.Z., et al., "Discovery of Selective Inhibitors of Glutaminase-2, which Inhibit mTORC1, Activate Autophagy and Inhibit Proliferation in Cancer Cells," Oncotarget 5(15):6087-6101, Impact Journals, United States (Aug. 2014).
Lentz, M.R., et al., "Changes in MRS Neuronal Markers and T Cell Phenotypes Observed During Early HIV Infection," Neurology 72(17):1465-1472, Lippincott Williams & Wilkins, United States (Apr. 2009).
Li, Q., et al., "A Central Role for mTOR Kinase in Homeostatic Proliferation Induced CD8+ T Cell Memory and Tumor Immunity," Immunity 34(4):541-553, Cell Press, United States (Apr. 2011).
Li, Y., et al., "Learning and Reconsolidation Implicate Different Synaptic Mechanisms," Proceedings of the National Academy of Sciences of the United States of America 110(12):4798-4803, National Academy of Sciences, United States (Mar. 2013).
Liddy, N., et al., "Monoclonal TCR-redirected Tumor Cell Killing," Nature Medicine 18(6):980-987, Nature Publishing Company, United States (Jun. 2012).
Lim, J.H., et al., "Targeting Mitochondrial Oxidative Metabolism in Melanoma Causes Metabolic Compensation through Glucose and Glutamine Utilization," Cancer Research 74(13):3535-3545, American Association for Cancer Research, United States (Jul. 2014).
Liu, W., et al., "Reprogramming of Proline and Glutamine Metabolism Contributes to the Proliferative and Metabolic Responses Regulated by Oncogenic Transcription Factor c-MYC," Proceedings of the National Academy of Sciences of the United States of America 109(23):8983-8988, National Academy of Sciences, United States (Jun. 2012).
Lo, Y.C., et al., "Insight into the Role of mTOR and Metabolism in T Cells Reveals New Potential Approaches to Preventing Graft Rejection," Current Opinion in Organ Transplantation 19(4):363-371, Lippincott Williams & Wilkins, United States (Aug. 2014).
Stupp, R., et al., "Effects of Radiotherapy with Concomitant and Adjuvant Temozolomide Versus Radiotherapy Alone on Survival in Glioblastoma in a Randomised Phase III Study: 5-year Analysis of the EORTC-NCIC Trial," The Lancet. Oncology 10(5):459-466, Lancet Pub. Group, England (May 2009).
Lynch, G., et al., "Phase II Evaluation of DON (6-diazo-5-oxo-L-norleucine) in Patients with Advanced Colorectal Carcinoma," American Journal of Clinical Oncology 5(5):541-543, Lippincott Williams & Wilkins, United States (Oct. 1982).
MacIntyre, A.N., et al., "The Glucose Transporter Glut1 is Selectively Essential for CD4 T Cell Activation and Effector Function," Cell Metabolism 20(1):61-72, Cell Press, United States (Jul. 2014).
MacIver, N.J., et al., "Metabolic Regulation of T Lymphocytes," Annual Review of Immunology 31:259-283, Annual Reviews Inc, United States (2013).
Magill, G.B. and Myers, W.P., "Alterations in Calcium Metabolism in Cancer Patients Treated with 6-diazo-5-oxo-L-norleucine," Proceedings of the Society for Experimental Biology and Medicine 93(2):314-318, Blackwell Science, United States (Nov. 1956).
Magill, G.B., et al., "Pharmacological and Initial Therapeutic Observations on 6-diazo-5-oxo-1-norleucine (DON) in Human Neoplastic Disease," Cancer 10(6):1138-1150, Wiley, United States (Nov.-Dec. 1957).
McArthur, J.C., et al., "Human Immunodeficiency Virus-associated Neurocognitive Disorders: Mind the Gap," Annals of Neurology 67(6):699-714, Wiley-Liss, United States (Jun. 2010).
McDermott, L.A., et al., "Design and Evaluation of Novel Glutaminase Inhibitors," Bioorganic & Medicinal Chemistry 24(8):1819-1839, Elsevier Science, England (Apr. 2016).
McGaugh, J.L., "Memory—a Century of Consolidation," Science 287(5451):248-251, American Association for the Advancement of Science, United States (Jan. 2000).
Medina, M.A., et al., "Relevance of Glutamine Metabolism to Tumor Cell Growth," Molecular and Cellular Biochemistry 113(1):1-15, Springer, Netherlands (Jul. 1992).
Michalek, R.D., et al., "Cutting Edge: Distinct Glycolytic and Lipid Oxidative Metabolic Programs are Essential for Effector and Regulatory CD4+ T Cell Subsets," Journal of Immunology 186(6):3299-3303, American Association of Immunologists, United States (Mar. 2011).
Nakaya, M., et al., "Inflammatory T Cell Responses Rely on Amino Acid Transporter ASCT2 Facilitation of Glutamine Uptake and mTORC1 Kinase Activation," Immunity 40(5):692-705, Cell Press, United States (May 2014).
Nedelcovych, M.T., et al., "N-(Pivaloyloxy)alkoxy-carbonyl Prodrugs of the Glutamine Antagonist 6-Diazo-5-oxo-L-norleucine (DON) as a Potential Treatment for HIV Associated Neurocognitive Disorders," Journal of Medicinal Chemistry 60(16):7186-7198, American Chemical Society, United States (Aug. 2017).
Ngiow, S.F., et al., "Prospects for TIM3-Targeted Antitumor Immunotherapy," Cancer Research 71(21):6567-6571, American Association for Cancer Research, United States (Nov. 2011).
Nishio, M., et al., "Antiviral Effect of 6-diazo-5-oxo-L-norleucine, Antagonist of Gamma-glutamyl Transpeptidase, on Replication of Human Parainfluenza Virus Type 2," The Journal of General Virology 71( Pt 1):61-67, Microbiology Society, England (Jan. 1990).

(56) References Cited

OTHER PUBLICATIONS

Oberhuber, R., et al., "Murine Cervical Heart Transplantation Model using a Modified Cuff Technique," Journal of Visualized Experiments 92:e50753, MYJoVE Corporation, United States (Oct. 2014).
Oderup, C., et al., "Costimulation Blockade-Induced Cardiac Allograft Tolerance: Inhibition of T Cell Expansion and Accumulation of Intragraft cD4+Foxp3+ T Cells," Transplantation 82(11):1493-1500, Lippincott Williams & Wilkins, United States (Dec. 2006).
Online Mendelian Inheritance in Man, OMIM as of [retrieved on May 1, May 1, 2010]. World Wide Web Retrieved from the Internet: (URL: http://www.ncbi.nlm.nih.gov/omim/and m OnlineMendelianInheritance in Animals (OMIA) at http://omia.angis.org.au/contact.shtml).
Ostrom, Q.T., et al., "CBTRUS Statistical Report: Primary Brain and Central Nervous System Tumors Diagnosed in the United States in 2008-2012," Neuro-oncology 17(Suppl 4):iv1-iv62, Oxford University Press, England (Oct. 2015).
Ovejera, A.A., et al., "Efficacy of 6-diazo-5-oxo-L-norleucine and N-[N-gamma-glutamyl-6-diazo-5-oxo-norleuciny1]-6-diazo-5-oxo-norleucine against Experimental Tumors in Conventional and Nude Mice," Cancer Research 39(8):3220-3224, American Association for Cancer Research, United States (Aug. 1979).
Pawlik, T.M., et al., "Hepatic Glutamine Transporter Activation in Burn Injury: Role of Amino Acids and Phosphatidylinositol-3-kinase," American Journal of Physiology. Gastrointestinal and Liver Physiology 278(4):G532-G541, American Physiological Society, United States (Apr. 2000).
Pearce, E.L., et al., "Fueling Immunity: Insights into Metabolism and Lymphocyte Function," Science 342(6155):1242454, American Association for the Advancement of Science, United States (Oct. 2013).
Pilon, C.B., et al., "Administration of Low Doses of IL-2 Combined to Rapamycin Promotes Allogeneic Skin Graft Survival in Mice," American Journal of Transplantation 14(12):2874-2882, Wiley-Blackwell, United States (Dec. 2014).
Pollizzi, K.N. and Powell, J.D., "Integrating Canonical and Metabolic Signalling Programmes in the Regulation of T Cell Responses," Nature Reviews. Immunology 14(7):435-446, Nature Pub. Group, England (Jul. 2014).
Potter, M.C., et al., "Neurological Sequelae Induced by Alphavirus Infection of the CNS are Attenuated by Treatment with the Glutamine Antagonist 6-diazo-5-oxo-1-norleucine," Journal of Neurovirology 21(2):159-173, Stockton Press, United States (Apr. 2015).
Potter, M.C., et al., "Targeting the Glutamatergic System for the Treatment of HIV-associated Neurocognitive Disorders," Journal of Neuroimmune Pharmacology 8(3):594-607, Springer Science, United States (Jun. 2013).
Powell, J.D. and Zheng, Y., "Dissecting the Mechanism of T-cell Anergy with Immunophilin Ligands," Current Opinion in Investigational Drugs 7(11):1002-1007, Thomson Reuters, England (Nov. 2006).
Powell, J.D., et al., "A Modified Model of T-Cell Differentiation Based on mTOR Activity and Metabolism," Cold Spring Harbor Symposia on Quantitative Biology 78(1):125-130, Cold Spring Harbor Laboratory Press, United States (2013).
Powell, J.D., et al., "A2ar Antagonists: Next Generation Checkpoint Blockade for Cancer Immunotherapy," Computational and Structural Biotechnology Journal 13:265-272, Elsevier B.V, Netherlands (Apr. 2015).
Pugh, C.R., et al., "Selective Effects of Peripheral Lipopolysaccharide Administration on Contextual and Auditory-cue Fear Conditioning," Brain, Behavior, and Immunity 12(3):212-229, Elsevier, Netherlands (Sep. 1998).
Raez, L.E., et al., "A Phase I Dose-escalation Trial of 2-deoxy-d-glucose Alone or Combined with Docetaxel in Patients with Advanced Solid Tumors," Cancer Chemotherapy and Pharmacology 71(2):523-530, Springer Verlag, Germany (Feb. 2013).
Rahman, A., et al., "Phase I Study and Clinical Pharmacology of 6-diazo-5-oxo-L-norleucine (DON)," Investigational New Drugs 3(4):369-374, Springer, United States (1985).
Rahn, K.A., et al., "Inhibition of Glutamate Carboxypeptidase II (GCPII) Activity as a Treatment for Cognitive Impairment in Multiple Sclerosis," Proceedings of the National Academy of Sciences of the United States of America 109(49):20101-20106, National Academy of Sciences, United States (Dec. 2012).
Rais, R., et al., "Discovery of 6-diazo-5-oxo-L-norleucine (DON) Prodrugs with Enhanced CSF Delivery in Monkeys: a Potential Treatment for Glioblastoma," Journal of Medicinal Chemistry 59(18):8621-8633, American Chemical Society, United States (Sep. 2016).
Rautio, J., et al., "Prodrugs: Design and Clinical Applications," Nature Reviews. Drug Discovery 7(3):255-270, Nature Publishing Group, England (Mar. 2008).
Reitzer, L.J., et al., "Evidence that Glutamine, not Sugar, is the Major Energy Source for Cultured HeLa Cells," The Journal of Biological Chemistry 254(8):2669-2676, American Society for Biochemistry and Molecular Biology, United States (Apr. 1979).
Robertson, K.R., et al., "The Prevalence and Incidence of Neurocognitive Impairment in the HAART Era," AIDS 21(14):1915-1921, Lippincott Williams & Wilkins, England (Sep. 2007).
Roodnat, J.I., et al., "15-year Follow-up of a Multicenter, Randomized, Calcineurin Inhibitor withdrawal Study in Kidney Transplantation," Transplantation 98(1):47-53, Lippincott Williams & Wilkins, United States (Jul. 2014).
Rowe, I., et al., "Defective Glucose Metabolism in Polycystic Kidney Disease Identifies a New Therapeutic Strategy," Nature Medicine 19(4):488-493, Nature Publishing Company, United States (Apr. 2013).
Roybal, K., et al., "Mania-like Behavior Induced by Disruption of CLOCK," Proceedings of the National Academy of Sciences of the United States of America 104(15):6406-6411, National Academy of Sciences, United States (Apr. 2007).
Ru, P., et al., "Tumor Metabolism of Malignant Gliomas," Cancers 5(4):1469-1484, MDPI, Switzerland (Dec. 2013).
Rubin, J., et al., "A Phase II Study of 6-diazo-5-oxo-L-norleucine (DON, NSC-7365) in Advanced Large Bowel Carcinoma," American Journal of Clinical Oncology 6(3):325-326, Lippincott Williams & Wilkins, United States (Jun. 1983).
Sailasuta, N., et al., "Change in Brain Magnetic Resonance Spectroscopy After Treatment During Acute HIV Infection," PLoS One 7(11):e49272, Public Library of Science, United States (2012).
Satake, A., et al., "Inhibition of Calcineurin Abrogates while Inhibition of mTOR Promotes Regulatory T Cell Expansion and Graft-versus-host Disease Protection by IL-2 in Allogeneic Bone Marrow Transplantation," PLoS One 9(3):e92888, Public Library of Science, United States (Mar. 2014).
Sayegh, M.H., and Carpente, C.B., "Transplantation 50 Years Later—progress, Challenges, and Promises," The New England Journal of Medicine 351(26):2761-2766, Massachusetts Medical Society, United States (Dec. 2004).
Sengupta, S., et al., "Regulation of the mTOR Complex 1 Pathway by Nutrients, Growth Factors, and Stress," Molecular Cell 40(2):310-322, Cell Press, United States (Oct. 2010).
Shah, U., and Hodgson, R., "Recent Progress in the Discovery of Adenosine A(2A) Receptor Antagonists for the Treatment of Parkinson's Disease," Current Opinion in Drug Discovery & Development 13(4):466-480, Thomson Reuters, England (Jul. 2010).
Shi, L.Z., et al., "HIF1alpha-dependent Glycolytic Pathway Orchestrates a Metabolic Checkpoint for the Differentiation of TH17 and Treg Cells," The Journal of Experimental Medicine 208(7):1367-1376, Rockefeller University Press, United States (Jul. 2011).
Shijie, J., et al., "Blockade of Glutamate Release from Microglia Attenuates Experimental Autoimmune Encephalomyelitis in Mice," The Tohoku Journal of Experimental Medicine 217(2):87-92, Tohoku University Medical Library, Japan (Feb. 2009).
Schulze, A. and Harris, A.L., "How Cancer Metabolism is Tuned for Proliferation and Vulnerable to Disruption," Nature 491(7424):364-373, Nature Publishing Group, England (Nov. 2012).

(56) References Cited

OTHER PUBLICATIONS

Shelton, L.M., et al., "Glutamine Targeting Inhibits Systemic Metastasis in the VM-M3 Murine Tumor Model," International Journal of Cancer 127(10):2478-2485, International Union Against Cancer, United States (Nov. 2010).
Shukla, K., et al., "Design, Synthesis, and Pharmacological Evaluation of Bis-2-(5-phenylacetamido-1,2,4-thiadiazo1-2-y1)ethyl Sulfide 3 (BPTES) Analogs as Glutaminase Inhibitors," Journal of Medicinal Chemistry 55(23):10551-10563, American Chemical Society, United States (Dec. 2012).
Sidman, et al., "Controlled Release of Macromolecules and Pharmaceuticals from Synthetic Polypeptides Based on Glutamic Acid," Biopolymers 22:547-556, John Wiley & Sons, Inc., United States (Jan. 1983).
Simioni, S., et al., "Cognitive Dysfunction in HIV Patients Despite Long-standing Suppression of Viremia," AIDS 24(9):1243-1250, Lippincott Williams & Wilkins, England (Jun. 2010).
Sklaroff, R.B., et al., "Phase I Study of 6-diazo-5-oxo-L-norleucine (DON)," Cancer Treatment Reports 64(12):1247-1251, National Cancer Institute, United States (1980).
Srikanth, K., et al., "Synthesis, Screening and Quantitative Structure-activity Relationship (QSAR) Studies of Some Glutamine Analogues for Possible Anticancer Activity," Bioorganic & Medicinal Chemistry 10(7):2119-2131, Elsevier Science, England (Jul. 2002).
Stupp, R., et al., "Radiotherapy Plus Concomitant and Adjuvant Temozolomide for Glioblastoma," The New England Journal of Medicine 352(10):987-996, Massachusetts Medical Society, United States (Mar. 2005).
Sullivan, M.P., et al., "A Comparison of the Effectiveness of Standard Dose 6-mercaptopurine, Combination 6-mercaptopurine and DON, and High-loading 6-mercaptopurine Therapies in Treatment of the Acute Leukemias of Childhood: Results of a Coperative Study," Cancer Chemotherapy Reports 18:83-95, National Cancer Institute, United States (May 1962).
Sullivan, M.P., et al., "Pharmacokinetic and Phase I Study of Intravenous DON (6-diazo-5-oxo-L-norleucine) in Children," Cancer Chemotherapy Reports 21(1):78-84, Springer Verlag, Germany (1988).
Suzuki, A., et al., "Memory Reconsolidation and Extinction have Distinct Temporal and Biochemical Signatures," The Journal of Neuroscience 24(20):4787-4795, Society for Neuroscience, United States (May 2004).
Tanaka, K., et al., "Compensatory Glutamine Metabolism Promotes Glioblastoma Resistance to mTOR Inhibitor Treatment," The Journal of Clinical Investigation 125(4):1591-1602, American Society for Clinical Investigation, United States (Apr. 2015).
Tarnowski, G.S., and Stock, C.C., "Effects of Combinations of Azaserine and of 6-diazo-5-oxo-L-norleucine with Purine Analogs and Other Antimetabolites on the Growth of Two Mouse Mammary Carcinomas," Cancer Research 17(10):1033-1039, American Association for Cancer Research, United States (Nov. 1957).
Thangavelu, K., et al., "Structural Basis for the Active Site Inhibition Mechanism of Human Kidney-type Glutaminase (KGA)," Scientific Reports 4:3827, Nature Publishing Group, England (Jan. 2014).
Thomas, A.G., et al., "Kinetic Characterization of Ebselen, Chelerythrine and Apomorphine as Glutaminase Inhibitors," Biochemical and Biophysical Research Communications 438(2):243-248, Elsevier, United States (Aug. 2013).
Thomas, A.G., et al., "Small Molecule Glutaminase Inhibitors Block Glutamate Release from Stimulated Microglia," Biochemical and Biophysical Research Communications 443(1):32-36, Elsevier, United States (Jan. 2014).
Thomson, L.M., and Sutherland, R.J., "Systemic Administration of Lipopolysaccharide and Interleukin-1beta have Different Effects on Memory Consolidation," Brain Research Bulletin 67(1-2):24-29, Elsevier Science, United States (Sep. 2005).
Tran, T.Q., et al., "Glutamine Deficiency Induces DNA Alkylation Damage and Sensitizes Cancer Cells to Alkylating Agents through Inhibition of ALKBH Enzymes," PLoS Biology 15(11):e2002810, Public Library of Science, United States (Nov. 2017).
Tsilidis, K.K., et al., "Metformin does not Affect Cancer Risk: A Cohort Study in the U.K. Clinical Practice Research Datalink Analyzed like an Intention-to-Treat Trial," Diabetes Care 37(9):2522-2532, American Diabetes Association, United States (Sep. 2014).
Ueki, N., et al., "Synthesis and Preclinical Evaluation of a Highly Improved Anticancer Prodrug Activated by Histone Deacetylases and Cathepsin L," Theranostics 6(6):808-816, Ivyspring International Publisher, Australia (Mar. 2016).
Upadhyay, R.K., "Drug Delivery Systems, CNS Protection, and the Blood Brain Barrier," BioMed Research International 2014:869269, Hindawi Pub. Co, United States (2014).
Vander Heiden, M.G., et al., "Understanding the Warburg Effect: The Metabolic Requirements of Cell Proliferation," Science 324(5930):1029-1033, American Association for the Advancement of Science, United States (May 2009).
Varoqui, H., et al., "Cloning and Functional Identification of a Neuronal Glutamine Transporter," The Journal of Biological Chemistry 275(6):4049-4054, American Society for Biochemistry and Molecular Biology, United States (Feb. 2000).
Waickman, A.T., and Powell, J.D., "mTOR, Metabolism, and the Regulation of T-cell Differentiation and Function," Immunological Reviews 249(1):43-58, Blackwell, England (Sep. 2012).
Wang, R., et al., "The Transcription Factor Myc Controls Metabolic Reprogramming upon T Lymphocyte Activation," Immunity 35(6):871-882, Cell Press, United States (Dec. 2011).
Warburg, O., "On Respiratory Impairment in Cancer Cells," Science 124(3215):269-270, American Association for the Advancement of Science, United States (Aug. 1956).
Weller, M., et al., "EANO Guideline for the Diagnosis and Treatment of Anaplastic Gliomas and Glioblastoma.," The Lancet. Oncology 15(9):e395-403, Lancet Pub. Group, England (Aug. 2014).
Willems, L., et al., "Inhibiting Glutamine Uptake Represents an Attractive New Strategy for Treating Acute Myeloid Leukemia," Blood 122(20):3521-3532, American Society of Hematology, United States (Nov. 2013).
Willis, R.C. and Seegmiller, J.E., "The Inhibition by 6-diazo-5-oxo-L-norleucine of Glutamine Catabolismof the Cultured Human Lymphoblast," Journal of Cellular Physiology 93(3):375-382, Wiley-Liss, United States (Dec. 1977).
Windmueller, H.G. and Spaeth, A.E., "Uptake and Metabolism of Plasma Glutamine by the Small Intestine," The Journal of Biological Chemistry 249(16):5070-5079, American Society for Biochemistry and Molecular Biology, United States (Aug. 1974).
Wise, D.R. and Thompson, C.B., "Glutamine Addiction: a New Therapeutic Target in Cancer," Trends in Biochemical Sciences 35(8):427-433, Elsevier Trends Journals, England (Aug. 2010).
Wise, D.R., et al., "Myc Regulates a Transcriptional Program that Stimulates Mitochondrial Glutaminolysis and Leads to Glutamine Addiction," Proceedings of the National Academy of Sciences of the United States of America 105(48):18782-18787, National Academy of Sciences, United States (Dec. 2008).
Wook Koo, J., et al., "Essential Role of Mesolimbic Brain-Derived Neurotrophic Factor in Chronic Social Stress-InducedDepressive Behaviors," Biological Psychiatry 80(6):469-478, Elsevier, United States (Sep. 2016).
Wu, T., et al., "Immunosuppressive Drugs on Inducing Ag-specific CD4(+)CD25(+)Foxp3(+) Treg Cells During Immune Response in Vivo," Transplant Immunology 27(1):30-38, Elsevier, Netherlands (Aug. 2012).
Yamasaki, T., et al., "Exploring a Glycolytic Inhibitor for the Treatment of an FH-deficient Type-2 Papillary RCC," Nature Reviews. Urology 8(3):165-171, Nature Pub. Group, England (Mar. 2011).
Yang, K. and Chi, H., "mTOR and Metabolic Pathways in T Cell Quiescence and Functional Activation," Seminars in Immunology 24(6):421-428, Academic Press, England (Dec. 2012).
Zgodka, D., et al., "A Diffusible Analogue of N3-(4-methoxyfumaroyl)-1-2,3-diaminopropanoic Acid With Antifungal Activity," Microbiology 147(Pt 7):1955-1959, (Jul. 2001).
Zhang, W., et al., "Overexpression of Cysteine Cathepsin L Is a Marker of Invasion and Metastasis in Ovarian Cancer," Oncology Reports 31(3):1334-1342, D.A. Spandidos, Greece (Mar. 2014).

(56) References Cited

OTHER PUBLICATIONS

Zheng, Y., et al., "Anergic T Cells are Metabolically Anergic," Journal of Immunology 183(10):6095-6101, American Association of Immunologists, United States (Nov. 2009).
Zimmermann, S.C., et al., "N-substituted Prodrugs of Mebendazole Provide Improved Aqueous Solubility and Oral Bioavailability in Mice and Dogs," Journal of Medicinal Chemistry 61(9):3918-3929, American Chemical Society, United States (May 2018).
Zink, M.C, "Translational Research Models and Novel Adjunctive Therapies for NeuroAIDS," Journal of Neuroimmune Pharmacology 2(1):14-19, Springer Science + Business Media, United States (Mar. 2007).
Office Action mailed Dec. 14, 2018, for co-pending U.S. Appl. No. 15/885,147, filed Jan. 31, 2018, U.S. Patent and Trademark Office, Alexandria, Virginia.
Daye, D., et al., "Metabolic reprogramming in cancer: Unraveling the role of glutamine in tumorigenesis," Seminars in Cell & Developmental Biology 23:362-369, Elsevier Ltd., (2012).
Ostroukhova, M., et al., "Switching of Glucose Metabolism from Oxidative Phosphorylation to Aerobic Glycolysis (the Warburg Effect) in T-Cells from Patients with Asthma," J Allergy Clin Immunol 125 (Issue 2, Supplement 1) p. AB39, abstract 155 (2010).
Extended European Search Report, European Appl. No. 16833623.8, dated Feb. 12, 2019.
Abo-Ghalia, M, et al., "Synthesis of inhibitors of the meso-diaminopimelate-adding enzyme from *Escherichia coli*", Int. J. Peptide Protein Res. 32:208-222, Munksgaard International Publishers, Copenhagen (1988).
Jancarik, A. "Novel lymphoid targeted prodrugs of the glutamine antagonist DON for the treatment of hematological malignancies", The FASEB Journal, Abstract No. 1b472, Published Online: Apr. 1, 2016.
Englert, J. et al., "Abstract 1035: Targeting glutamine metabolism with the novel inhibitor JHU-083 inhibits tumor growth and alters the tumor immune microenvironment", Proceedings: AACR 107th Annual Meeting, New Orleans, LA, American Association for Cancer Research, Apr. 16-20, 2016.
Extended European Search Report, European Appl. No. 16833638.6, dated May 22, 2019.
Ramsay: "Immune checkpoint blockade immunotherapy to activate anti-tumour T-cell immunity", The British Journal of Haematology 162:313-325, John Wiley & Sons Ltd. (2013).
Renault: "Getting away with murder: how does the BCL-2 family of proteins kill with immunity?: The BCL-2 family as regulators of immunity", Annals of The New York Academy of Sciences 1285:59-79, The New York Academy of Sciences (2013).
Sharma, N.S., et al. Targeting tumor intrinsic metabolic node in pancreatic cancer causes tumor regression, remodels extracellular matrix and sensitizes to anti-PD1 therapy. BioRxiv preprint posted Jan. 12, 2019, DOI:10.1101/519462.
International Search Report and Written Opinion for International Application No. PCT/US2021/053159, U.S. Patent and Trademark Office, Virginia, mailed on Jan. 12, 2022, 22 pages.
International Search Report and Written Opinion for International Application No. PCT/US2020/054071, U.S. Patent and Trademark Office, Virginia, mailed on Jan. 13, 2021, 16 pages.
Kasper, J.C., et al. "Development of a lyophilized plasmid/LPEI polyplex formulation with long-term stability—A step closer from promising technology to application," Journal of Controlled Release 151:246-255, Elsevier B.V., The Netherlands (2011).
Ling, P., ed., *Drug Formulation Technology*, p. 124, China Light Industry Press, Beijing, China (2007).
Li, D., et al., "Advances in antitumor drugs based on glutamine metabolism," Chinese Journal of Clinical Pharmacology and Therapeutics, 25(7):810-816, Chinese Pharmacological Society, China (Jul. 2020).
Wu, F., et al., "Effect of 6-diazo-5-oxo-L-norleucine (DON) on human carcinoid tumor cell aggregates," Anticancer Res. 17(4A):2363-2367, International Institute of Anticancer Research (IIAR), Greece (Jul. 1997).

* cited by examiner

LYOPHILIZED COMPOSITION COMPRISING (S)-ISOPROPYL 2-((S)-2-ACETAMIDO-3-(1H-INDOL-3-YL) PROPANAMIDO)-6-DIAZO-5-OXOHEXANOATE FOR SUBCUTANEOUS ADMINISTRATION AND THE USE THEREOF

BACKGROUND OF THE INVENTION

6-Diazo-5-oxo-L-norleucine (DON) is a glutamine antagonist that exhibits promising activity in preclinical models to treat a variety of diseases such as cancer. See, e.g., Ahluwalia et al., *Pharmac The.* 46:243-371 (1990). But the clinical development of DON has been hampered by its dose-limiting toxicity in humans, especially in the intestinal epithelium. See, e.g., Rosenfeld and Roberts, *Cancer Research* 41:1324-1328 (1981) and Lynch et al., *Am J Clin Oncol* (*CCT*) 5:541-543 (1982). Administering DON as a prodrug may help mitigate this toxicity.

U.S. Pat. No. 10,336,778 B2 discloses (S)-isopropyl 2-((S)-2-acetamido-3-(1H-indol-3-yl)propanamido)-6-diazo-5-oxohexanoate ("Compound 1") and other prodrugs of DON for the treatment of cancer and other diseases. There exists a need for pharmaceutical compositions comprising Compound 1 for subcutaneous administration to a subject in need thereof.

BRIEF SUMMARY OF THE INVENTION

In one aspect, the disclosure provides a lyophilate comprising Compound 1 for subcutaneous administration to a subject in need thereof.

In another aspect, the disclosure provides a lyophilate comprising Compound 1 and a bulking agent, e.g., mannitol.

In another aspect, the disclosure provides a lyophilate comprising Compound 1 and a cellulose-based suspension modulator, e.g., sodium carboxymethyl cellulose.

In another aspect, the disclosure provides a lyophilate comprising Compound 1 and a poloxamer-based suspension modulator, e.g., Poloxamer 188.

In another aspect, the disclosure provides a lyophilate comprising Compound 1 and a lecithin-based suspension modulator, e.g., soy lecithin.

In another aspect, the disclosure provides a lyophilate comprising Compound 1 and a buffering agent, e.g., L-histidine.

In another aspect, the disclosure provides a pharmaceutical composition comprising a lyophilate comprising Compound 1 that has been suspended in a pharmaceutically acceptable excipient, e.g., a solvent, e.g., water.

In another aspect, the disclosure provides a method for treating a cancer in a subject in need thereof comprising subcutaneously administering a therapeutically effective amount of a pharmaceutical composition comprising a lyophilate comprising Compound 1.

In another aspect, the disclosure provides a method of making the lyophilate comprising Compound 1.

In another aspect, the disclosure provides a method of making the pharmaceutical composition comprising a lyophilate comprising Compound 1.

In another aspect, the disclosure provides a kit comprising the lyophilate comprising Compound 1 packaged as single unit dose in a vial.

DETAILED DESCRIPTION OF THE INVENTION

I. Lyophilates of the Disclosure

Figure 1:
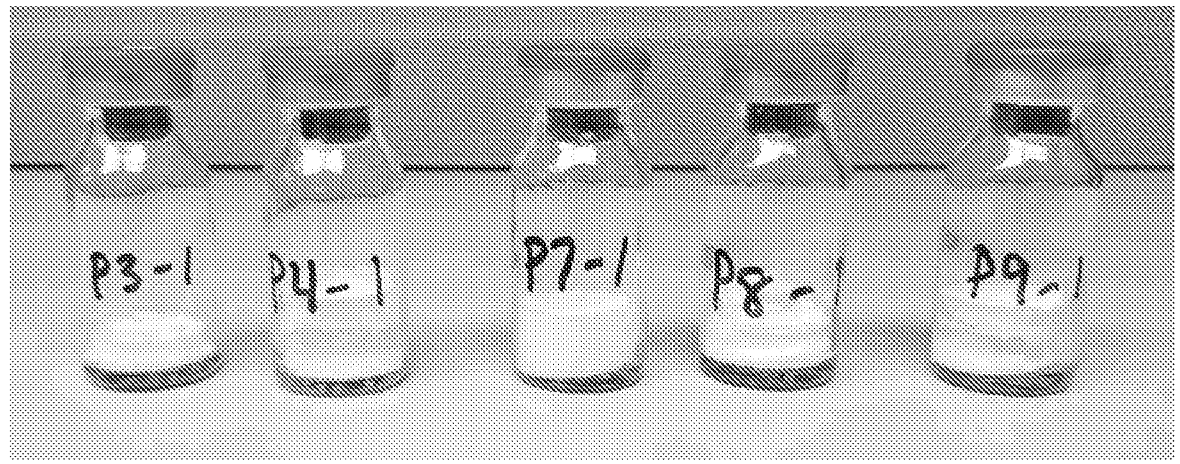
FIG. 1 is an image showing the lyophilized cake appearance of five lyophilates comprising Compound 1.
Figure 2:
FIG. 2 is an image showing the appearance of a pharmaceutical composition comprising Compound 1 suspended in 2.5 mL of water for injection.

In one embodiment, the disclosure provides a lyophilate comprising Compound 1 for subcutaneous administration to a subject in need thereof.

In another embodiment, the disclosure provides a lyophilate comprising Compound 1 and a bulking agent. In another embodiment, the Compound 1/bulking agent weight ratio is about 5 to about 0.05. In another embodiment, the Compound 1/bulking agent weight ratio is about 3 to about 0.1. In another embodiment, the Compound 1/bulking agent weight ratio is about 1 to about 0.2. In another embodiment, the Compound 1/bulking agent weight ratio is about 3, about 2, about 1, about 0.9, about 0.8, about 0.7, about 0.6, about 0.5, about 0.4, about 0.3, about 0.2, or about 0.1. In another embodiment, the bulking agent is mannitol.

In another embodiment, the disclosure provides a lyophilate comprising Compound 1 and a cellulose-based suspension modulator. In another embodiment, the Compound 1/cellulose-based suspension modulator weight ratio is about 25 to about 0.3. In another embodiment, the Compound 1/cellulose-based suspension modulator weight ratio is about 15 to about 0.5. In another embodiment, the Compound 1/cellulose-based suspension modulator weight ratio is about 10 to about 1. In another embodiment, the Compound 1/cellulose-based suspension modulator weight ratio is about 5 to about 2. In another embodiment, the Compound 1/cellulose-based suspension modulator weight ratio is about 10, about 9, about 8, about 7.5, about 7, about 6, about 5, about 4, about 3, about 2.7, about 2, or about 1. In another embodiment, the cellulose-based suspension modulator is sodium carboxymethyl cellulose.

In another embodiment, the disclosure provides a lyophilate comprising Compound 1 and a poloxamer-based suspension modulator. In another embodiment, the Compound 1/poloxamer-based suspension modulator weight ratio is about 80 to about 1. In another embodiment, the Compound 1/poloxamer-based suspension modulator weight ratio is about 40 to about 2. In another embodiment, the Compound 1/poloxamer-based suspension modulator weight ratio is about 20, about 19, about 18, about 17, about 16, about 15, about 14, about 13, about 12, about 11, about 10, about 9, about 8.8, about 7, about 6, about 5, about 4, about 3, or about 2. In another embodiment, the poloxamer-based suspension modulator is Poloxamer 188 (a copolymer of polyoxyethylene and polyoxypropylene).

In another embodiment, the disclosure provides a lyophilate comprising Compound 1 and lecithin-based suspension modulator. In another embodiment, the Compound 1/lecithin-based suspension modulator weight ratio is about 15 to about 0.15. In another embodiment, the Compound 1/lecithin-based suspension modulator weight ratio is about 8 to about 0.3. In another embodiment, the Compound 1/lecithin-based suspension modulator weight ratio is about 5 to about 0.6. In another embodiment, the Compound 1/lecithin-based suspension modulator weight ratio is about 3 to about 1. In another embodiment, the Compound 1/lecithin-based suspension modulator weight ratio is about 5, about 4, about 3, about 2, about 1.5, about 1, about 0.6. In another embodiment, the lecithin-based suspension modulator is soy lecithin.

In another embodiment, the disclosure provides a lyophilate comprising Compound 1 and a buffering agent. In another embodiment, the Compound 1/buffering agent weight ratio is about 50 to about 1. In another embodiment, the Compound 1/buffering agent weight ratio is about 25 to about 10. In another embodiment, the Compound 1/buffering agent weight ratio is about 20 to about 15. In another embodiment, the Compound 1/buffering agent weight ratio is about 25, about 24, about 23, about 22, about 21, about 20, about 21, about 20, about 19, about 18, about 17.4, about 17, about 16, about 15, about 14, about 13, about 12, about 11, or about 10. In another embodiment, the buffering agent is L-histidine.

In another embodiment, the disclosure provides a lyophilate comprising Compound 1, a bulking agent, at least one of a cellulose-based suspension modulator, a poloxamer-based suspension modulator, or a lecithin-based suspension modulator, and, optionally, a buffering agent.

In another embodiment, the disclosure provides a lyophilate comprising Compound 1, a bulking agent, and at least two of a cellulose-based suspension modulator, a poloxamer-based suspension modulator, or a lecithin-based suspension modulator, and, optionally, a buffering agent.

In another embodiment, the disclosure provides a lyophilate comprising Compound 1, a bulking agent, a cellulose-based suspension modulator, a poloxamer-based suspension modulator, and a lecithin-based suspension modulator, and, optionally, a buffering agent.

In another embodiment, the disclosure provides a lyophilate comprising about 20% wt/wt to about 45% wt/wt of Compound 1 and about 35% wt/wt to about 55% wt/wt of a bulking agent.

In another embodiment, the disclosure provides a lyophilate comprising Compound 1, mannitol, sodium carboxymethyl cellulose, poloxamer 188, and soy lecithin, and, optionally, L-histidine.

In another embodiment, the disclosure provides a lyophilate comprising about 10 mg to about 120 mg of Compound 1. In another embodiment, the disclosure provides a lyophilate comprising about 20 mg to about 110 mg of Compound 1. In another embodiment, the disclosure provides a lyophilate comprising about 30 mg to about 100 mg of Compound 1. In another embodiment, the disclosure provides a lyophilate comprising about 40 mg to about 90 mg of Compound 1. In another embodiment, the disclosure provides a lyophilate comprising about 50 mg to about 80 mg of Compound 1. In another embodiment, the disclosure provides a lyophilate comprising about 60 mg to about 70 mg of Compound 1. In another embodiment, the disclosure provides a lyophilate comprising about 10 mg, about 15 mg, about 20 mg, about 25 mg, about 30 mg, about 35 mg, about 40 mg, about 42 mg, about 45 mg, about 50 mg, about 55 mg, about 60 mg, about 62.5 mg, about 65 mg, about 67.5 mg, about 70 mg, about 75 mg, about 80 mg, about 85 mg, about 90 mg, about 95 mg, about 100 mg, about 105 mg, about 110 mg, or about 120 mg of Compound 1.

In another embodiment, the disclosure provides a lyophilate comprising about 50 mg to about 250 mg of a bulking agent. In another embodiment, the disclosure provides a lyophilate comprising about 60 mg to about 210 mg of a bulking agent. In another embodiment, the disclosure provides a lyophilate comprising about 70 mg to about 200 mg of a bulking agent. In another embodiment, the disclosure provides a lyophilate comprising about 80 mg to about 190 mg of a bulking agent. In another embodiment, the disclosure provides a lyophilate comprising about 90 mg to about 180 mg of a bulking agent. In another embodiment, the disclosure provides a lyophilate comprising about 100 mg to about 170 mg of a bulking agent. In another embodiment, the disclosure provides a lyophilate comprising about 110 mg to about 160 mg of a bulking agent. In another embodiment, the disclosure provides a lyophilate comprising about 120 mg to about 150 mg of a bulking agent. In another embodiment, the disclosure provides a lyophilate comprising about 125 mg to about 140 mg of a bulking agent. In another embodiment, the disclosure provides a lyophilate comprising about 50 mg, about 55 mg, about 60 mg, about 65 mg, about 70 mg, about 75 mg, about 80 mg, about 85 mg, about 90 mg, about 95 mg, about 100 mg, about 105, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180, about 185 mg, about 190 mg, about 195 mg, about 200 mg, about 205 mg, about 210 mg, about 215 mg, or about 220 mg of a bulking agent. In another embodiment, the bulking agent is mannitol.

In another embodiment, the disclosure provides a lyophilate comprising about 1 mg to about 100 mg of a cellulose-based suspension modulator. In another embodiment, the disclosure provides a lyophilate comprising about 5 mg to about 75 mg of a cellulose-based suspension modulator. In another embodiment, the disclosure provides a lyophilate comprising about 5 mg to about 50 mg of a cellulose-based suspension modulator. In another embodiment, the disclosure provides a lyophilate comprising about 5 mg to about 10 mg of a cellulose-based suspension modulator. In another embodiment, the disclosure provides a lyophilate comprising about 20 mg to about 30 mg of a cellulose-based suspension modulator. In another embodiment, the disclosure provides a lyophilate comprising about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 25.2 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, or about 50 mg of a cellulose-based suspension modulator. In another embodiment, the cellulose-based suspension modulator is sodium carboxymethyl cellulose.

In another embodiment, the disclosure provides a lyophilate comprising about 0.5 mg to about 70 mg of a poloxamer-based suspension modulator. In another embodiment, the disclosure provides a lyophilate comprising about 1 mg to about 40 mg of a poloxamer-based suspension modulator. In another embodiment, the disclosure provides a lyophilate comprising about 2 mg to about 30 mg of a poloxamer-based suspension modulator. In another embodiment, the disclosure provides a lyophilate comprising about 3 mg to about 20 mg of a poloxamer-based suspension modulator. In another embodiment, the disclosure provides a lyophilate comprising about 4 mg to about 10 mg of a poloxamer-based suspension modulator. In another embodiment, the disclosure provides a lyophilate comprising about 3 mg, about 4 mg, about 5 mg, about 6 mg, about 7 mg, about 7.65 mg, about 8, about 9, about 10 mg, about 11 mg, about 12 mg, about 13 mg, about 14 mg, about 15 mg, about 16 mg, about 17 mg, about 18 mg, about 19 mg, or about 20 mg of a poloxamer-based suspension modulator. In another embodiment, the poloxamer-based suspension modulator is Poloxamer 188.

In another embodiment, the disclosure provides a lyophilate comprising about 1 mg to about 100 mg of a lecithin-based suspension modulator. In another embodiment, the disclosure provides a lyophilate comprising about 10 mg to about 80 mg of a lecithin-based suspension modulator. In another embodiment, the disclosure provides a lyophilate comprising about 20 mg to about 70 mg of a lecithin-based suspension modulator. In another embodiment, the disclosure provides a lyophilate comprising about 30 mg to about 60 mg of a lecithin-based suspension modulator. In another embodiment, the disclosure provides a lyophilate comprising about 40 mg to about 50 mg of a lecithin-based suspension modulator. In another embodiment, the disclosure provides a lyophilate comprising about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59, or about 60 mg of a lecithin-based suspension modulator. In another embodiment, the lecithin-based suspension modulator is soy lecithin In another embodiment, the disclosure provides a lyophilate comprising about 0.1 mg to about 20 mg of a buffering agent. In another embodiment, the disclosure provides a lyophilate comprising about 0.5 mg to about 15 mg of a buffering agent. In another embodiment, the disclosure provides a lyophilate comprising about 1 mg to about 10 mg of a buffering agent. In another embodiment, the disclosure provides a lyophilate comprising about 2 mg to about 8 mg of a buffering agent. In another embodiment, the disclosure provides a lyophilate comprising about 3 mg to about 5 mg of a buffering agent. In another embodiment, the disclosure provides a lyophilate comprising about 0.1 mg, about 0.5 mg, about 1 mg, about 1.5 mg, about 2 mg, about 2.5 mg, about 3 mg, about 3.5 mg, about 3.9 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 10.5 mg, about 11 mg, about 11.5 mg, about 12 mg, about 12.5 mg, about 13 mg, about 13.5 mg, about 14 mg, about 14.5 mg, or about 15 mg of a buffering agent. In another embodiment, the buffering agent is L-histidine.

The present disclosure provides the following particular embodiments:

Embodiment I. A lyophilate comprising about 60 mg to about 70 mg of Compound 1 for subcutaneous administration to a subject.

Embodiment II. The lyophilate of Embodiment I comprising about 125 mg to about 140 mg of bulking agent, e.g., mannitol.

Embodiment III. The lyophilate of Embodiments I or II comprising about 8 mg to about 30 mg of a cellulose-based suspension modulator, e.g., sodium carboxymethyl cellulose.

Embodiment IV. The lyophilate of any one of Embodiments I-III comprising about 5 mg to about 10 mg of a poloxamer-based suspension modulator, e.g., Poloxamer 188.

Embodiment V. The lyophilate of any one of Embodiments I-IV comprising about 40 mg to about 50 mg of a lecithin-based suspension modulator, e.g., soy lecithin.

Embodiment VI. The lyophilate of any one of Embodiments I-V comprising about 2 mg to about 5 mg of a buffering agent, e.g., L-histidine.

The present disclosure provides the following particular embodiments:

Embodiment I-A. A lyophilate comprising about 110 mg to about 130 mg of Compound 1 for subcutaneous administration to a subject.

Embodiment II-A. The lyophilate of Embodiment I-A comprising about 110 mg to about 250 mg of bulking agent, e.g., mannitol.

Embodiment III-A. The lyophilate of Embodiments I-A or II-A comprising about 5 mg to about 30 mg of a cellulose-based suspension modulator, e.g., sodium carboxymethyl cellulose.

Embodiment IV-A. The lyophilate of any one of Embodiments I-A to III-A comprising about 5 mg to about 15 mg of a poloxamer-based suspension modulator, e.g., Poloxamer 188.

Embodiment V-A. The lyophilate of any one of Embodiments I-A to IV-A comprising about 40 mg to about 90 mg of a lecithin-based suspension modulator, e.g., soy lecithin.

Embodiment VI-A. The lyophilate of any one of Embodiments I-A to V-A comprising about 2 mg to about 10 mg of a buffering agent, e.g., L-histidine.

Representative lyophilates (designated L1-L5) of the present disclosure comprise Compound 1, mannitol, NaCMC, Poloxamer 188, NF, histidine, and soy lecithin in the following amounts:

| Ingredient | L1 | L2 | L2 | L4 | L5 |
|---|---|---|---|---|---|
| Compound 1 | 67.5 mg | 67.5 mg | 62.5 mg | 120.2 mg | 120.2 mg |
| | 23.7% wt/wt | 25.2% wt/wt | 25.1% wt/wt | 24.6% wt/wt | 40.1% wt/wt |
| Mannitol | 135 mg | 135 mg | 125 mg | 240.4 mg | 120.2 mg |
| | 47.5% wt/wt | 50.4% wt/wt | 50.2% wt/wt | 49.3% wt/wt | 40.1% wt/wt |
| NaCMC | 25.2 mg | 9.0 mg | 8.33 mg | 16.0 mg | 8.0 mg |
| | 8.9% wt/wt | 3.4% wt/wt | 3.3% wt/wt | 3.3% wt/wt | 2.7% wt/wt |
| Poloxamer | 7.65 mg | 7.65 mg | 7.08 mg | 13.6 mg | 6.8 mg |
| 188, NF | 2.7% wt/wt | 2.9% wt/wt | 2.8% wt/wt | 2.8% wt/wt | 2.3% wt/wt |
| Histidine | 3.88 mg | 3.88 mg | 4.31 mg | 8.3 mg | 4.1 mg |
| | 1.4% wt/wt | 1.4% wt/wt | 1.7% wt/wt | 1.7% wt/wt | 1.4% wt/wt |
| Soy Lecithin | 45 mg | 45 mg | 41.7 mg | 80.2 mg | 40.1 mg |
| | 15.8% wt/wt | 16.8% wt/wt | 16.8% wt/wt | 16.4% wt/wt | 13.4% wt/wt |
| Total | 284.23 mg | 268.03 mg | 248.9 mg | 487.7 mg | 299.4 mg |

In another embodiment, the moisture content of the lyophilate is about 4% or less as determined by the Karl Fischer method. In another embodiment, the moisture content of the lyophilate is about 3% or less. In another embodiment, the moisture content of the lyophilate is about 2% or less. In another embodiment, the moisture content of the lyophilate is about 1% or less. In another embodiment, the moisture content of the lyophilate is about 0.9%. In another embodiment, the moisture content of the lyophilate is about 0.8%. In another embodiment, the moisture content of the lyophilate is about 0.7%. In another embodiment, the moisture content of the lyophilate is about 0.6%. In another embodiment, the moisture content of the lyophilate is about 0.5%. In another embodiment, the moisture content of the lyophilate is about 0.4%. In another embodiment, the moisture content of the lyophilate is about 0.3%. In another embodiment, the moisture content of the lyophilate is about 0.2%. In another embodiment, the moisture content of the lyophilate is about 0.1%.

In another embodiment, the chemical purity of Compound 1 in the lyophilate is about 96% to about 99.9% as measured by HPLC. In another embodiment, the chemical purity of Compound 1 in the lyophilate is about 96%. In another embodiment, the chemical purity of Compound 1 in the lyophilate is about 96.5%. In another embodiment, the chemical purity of Compound 1 in the lyophilate is about 97%. In another embodiment, the chemical purity of Compound 1 in the lyophilate is about 97.5%. In another embodiment, the chemical purity of Compound 1 in the lyophilate is about 98%. In another embodiment, the chemical purity of Compound 1 in the lyophilate is about 98.5%. In another embodiment, the chemical purity of Compound 1 in the lyophilate is about 99.0%. In another embodiment, the chemical purity of Compound 1 in the lyophilate is about 99.5%.

In another embodiment, the disclosure provides a lyophilate comprising about 67.5 mg of Compound 1, about 135 mg of mannitol, about 25.2 mg of sodium carboxymethyl cellulose, about 7.65 mg of poloxamer 188, about 3.88 mg of L-histidine, and about 45 mg of soy lecithin.

In another embodiment, the disclosure provides a lyophilate consisting essentially of about 67.5 mg of Compound 1, about 135 mg of mannitol, about 25.2 mg of sodium carboxymethyl cellulose, about 7.65 mg of poloxamer 188, about 3.88 mg of L-histidine, and about 45 mg of soy lecithin.

In another embodiment, the disclosure provides a lyophilate consisting of about 67.5 mg of Compound 1, about 135 mg of mannitol, about 25.2 mg of sodium carboxymethyl cellulose, about 7.65 mg of poloxamer 188, about 3.88 mg of L-histidine, and about 45 mg of soy lecithin.

In another embodiment, the disclosure provides a lyophilate comprising about 67.5 mg of Compound 1, about 135 mg of mannitol, about 9.0 mg of sodium carboxymethyl cellulose, about 7.65 mg of poloxamer 188, about 3.88 mg of L-histidine, and about 45 mg of soy lecithin.

In another embodiment, the disclosure provides a lyophilate consisting essentially of about 67.5 mg of Compound 1, about 135 mg of mannitol, about 9.0 mg of sodium carboxymethyl cellulose, about 7.65 mg of poloxamer 188, about 3.88 mg of L-histidine, and about 45 mg of soy lecithin.

In another embodiment, the disclosure provides a lyophilate consisting of about 67.5 mg of Compound 1, about 135 mg of mannitol, about 9.0 mg of sodium carboxymethyl cellulose, about 7.65 mg of poloxamer 188, about 3.88 mg of L-histidine, and about 45 mg of soy lecithin.

In another embodiment, the disclosure provides a lyophilate comprising about 62.5 mg of Compound 1, about 125 mg of mannitol, about 8.33 mg of sodium carboxymethyl cellulose, about 7.08 mg of poloxamer 188, about 4.31 mg of L-histidine, and about 41.7 mg of soy lecithin.

In another embodiment, the disclosure provides a lyophilate consisting essentially of about 62.5 mg of Compound 1, about 125 mg of mannitol, about 8.33 mg of sodium carboxymethyl cellulose, about 7.08 mg of poloxamer 188, about 4.31 mg of L-histidine, and about 41.7 mg of soy lecithin.

In another embodiment, the disclosure provides a lyophilate consisting of about 62.5 mg of Compound 1, about 125 mg of mannitol, about 8.33 mg of sodium carboxymethyl cellulose, about 7.08 mg of poloxamer 188, about 4.31 mg of L-histidine, and about 41.7 mg of soy lecithin.

In another embodiment, the disclosure provides a lyophilate comprising about 120.2 mg of Compound 1, about 240.4 mg of mannitol, about 16 mg of sodium carboxymethyl cellulose, about 13.6 mg of poloxamer 188, about 8.3 mg of L-histidine, about 80.2 mg of soy lecithin.

In another embodiment, the disclosure provides a lyophilate consisting essentially of about 120.2 mg of Compound 1, about 240.4 mg of mannitol, about 16 mg of sodium carboxymethyl cellulose, about 13.6 mg of poloxamer 188, about 8.3 mg of L-histidine, about 80.2 mg of soy lecithin.

In another embodiment, the disclosure provides a lyophilate consisting of about 120.2 mg of Compound 1, about 240.4 mg of mannitol, about 16 mg of sodium carboxymethyl cellulose, about 13.6 mg of poloxamer 188, about 8.3 mg of L-histidine, about 80.2 mg of soy lecithin.

In another embodiment, the disclosure provides a lyophilate comprising about 120.2 mg of Compound 1, about 120.2 mg of mannitol, about 8 mg of sodium carboxymethyl cellulose, about 6.8 mg of poloxamer 188, about 4.1 mg of L-histidine, about 40.1 mg of soy lecithin.

In another embodiment, the disclosure provides a lyophilate consisting essentially of about 120.2 mg of Compound 1, about 120.2 mg of mannitol, about 8 mg of sodium carboxymethyl cellulose, about 6.8 mg of poloxamer 188, about 4.1 mg of L-histidine, about 40.1 mg of soy lecithin.

In another embodiment, the disclosure provides a lyophilate consisting of about 120.2 mg of Compound 1, about 120.2 mg of mannitol, about 8 mg of sodium carboxymethyl cellulose, about 6.8 mg of poloxamer 188, about 4.1 mg of L-histidine, about 40.1 mg of soy lecithin.

The lyophilates described in this section are collectively referred to as a "Lyophilate of the Disclosure."

II. Pharmaceutical Compositions of the Disclosure

In another embodiment, the disclosure provides a pharmaceutical composition comprising a Lyophilate of the Disclosure suspended in a solvent. In one embodiment, the solvent comprises water. In one embodiment, the solvent is water, e.g., sterile water for injection, USP.

In another embodiment, the disclosure provides a pharmaceutical composition comprising a Lyophilate of the Disclosure suspended in a solvent, wherein the concentration of Compound 1 is about 20 mg/mL to about 60 mg/mL, e.g., about 24 mg/mL to about 35 mg/mL. In another embodiment, the concentration of Compound 1 is about 25 mg/mL to about 30 mg/mL. In another embodiment, the concentration of Compound 1 is about 20 mg/mL. In another embodiment, the concentration of Compound 1 is about 21 mg/mL. In another embodiment, the concentration of Compound 1 is about 22 mg/mL. In another embodiment, the concentration of Compound 1 is about 23 mg/mL. In another embodiment, the concentration of Compound 1 is about 24 mg/mL. In another embodiment, the concentration of Compound 1 is about 25 mg/mL. In another embodiment, the concentration of Compound 1 is about 26 mg/mL. In another embodiment, the concentration of Compound 1 is about 27 mg/mL. In another embodiment, the concentration of Compound 1 is about 28 mg/mL. In another embodiment, the concentration of Compound 1 is about 29 mg/mL. In another embodiment, the concentration of Compound 1 is about 30 mg/mL. In another embodiment, the concentration of Compound 1 is about 31 mg/mL. In another embodiment, the concentration of Compound 1 is about 32 mg/mL. In another embodiment, the concentration of Compound 1 is about 33 mg/mL. In another embodiment, the concentration of Compound 1 is about 34 mg/mL. In another embodiment, the concentration of Compound 1 is about 35 mg/mL. In another embodiment, the concentration of Compound 1 is about 40 mg/mL. In another embodiment, the concentration of Compound 1 is about 45 mg/mL. In another embodiment, the concentration of Compound 1 is about 50 mg/mL. In another embodiment, the concentration of Compound 1 is about 55 mg/mL. In another embodiment, the concentration of Compound 1 is about 60 mg/mL.

In another embodiment, the disclosure provides a pharmaceutical composition comprising a Lyophilate of the Disclosure suspended in a solvent, wherein the average particle size distribution of Compound 1 in the suspension is about 0.1 μm to about 50 μm after 3 days at 2-8° C. In another embodiment, the average particle size distribution of Compound 1 in the suspension is about 1 μm to about 40 μm after 3 days at 2-8° C. In another embodiment, the average particle size distribution of Compound 1 in the suspension is about 10 μm to about 30 μm after 3 days at 2-8° C. In another embodiment, the average particle size distribution of Compound 1 in the suspension is about 10 μm to about 30 μm. In another embodiment, the average particle size distribution of Compound 1 in the suspension is about 10 μm after 3 days at 2-8° C. In another embodiment, the average particle size distribution of Compound 1 in the suspension is about 15 μm after 3 days at 2-8° C. In another embodiment, the average particle size distribution of Compound 1 in the suspension is about 20 μm after 3 days at 2-8° C. In another embodiment, the average particle size distribution of Compound 1 in the suspension is about 25 μm after 3 days at 2-8° C.

In another embodiment, the disclosure provides a pharmaceutical composition comprising about 67.5 mg of Compound 1, about 135 mg of mannitol, about 25.2 mg of sodium carboxymethyl cellulose, about 7.65 mg of poloxamer 188, about 3.88 mg of L-histidine, about 45 mg of soy lecithin, and about 2.5 mL of sterile water for injection, USP (WFI USP).

In another embodiment, the disclosure provides a pharmaceutical composition consisting essentially of about 67.5 mg of Compound 1, about 135 mg of mannitol, about 25.2 mg of sodium carboxymethyl cellulose, about 7.65 mg of poloxamer 188, about 3.88 mg of L-histidine, about 45 mg of soy lecithin, and about 2.5 mL of sterile water for injection, USP.

In another embodiment, the disclosure provides a pharmaceutical composition consisting of about 67.5 mg of Compound 1, about 135 mg of mannitol, about 25.2 mg of sodium carboxymethyl cellulose, about 7.65 mg of poloxamer 188, about 3.88 mg of L-histidine, about 45 mg of soy lecithin, and about 2.5 mL of sterile water for injection, USP.

In another embodiment, the disclosure provides a pharmaceutical composition comprising about 67.5 mg of Compound 1, about 135 mg of mannitol, about 9.0 mg of sodium carboxymethyl cellulose, about 7.65 mg of poloxamer 188, about 3.88 mg of L-histidine, about 45 mg of soy lecithin, and about 2.25 mL of sterile water for injection, USP.

In another embodiment, the disclosure provides a pharmaceutical composition consisting essentially of about 67.5 mg of Compound 1, about 135 mg of mannitol, about 9.0 mg of sodium carboxymethyl cellulose, about 7.65 mg of poloxamer 188, about 3.88 mg of L-histidine, about 45 mg of soy lecithin, and about 2.25 mL of sterile water for injection, USP.

In another embodiment, the disclosure provides a pharmaceutical composition consisting of about 67.5 mg of Compound 1, about 135 mg of mannitol, about 9.0 mg of sodium carboxymethyl cellulose, about 7.65 mg of poloxamer 188, about 3.88 mg of L-histidine, about 45 mg of soy lecithin, and about 2.25 mL of sterile water for injection, USP.

In another embodiment, the disclosure provides a pharmaceutical composition comprising about 62.5 mg of Compound 1, about 125 mg of mannitol, about 8.33 mg of sodium carboxymethyl cellulose, about 7.08 mg of poloxamer 188, about 4.31 mg of L-histidine, about 41.7 mg of soy lecithin, and about 2.5 mL of sterile water for injection, USP.

In another embodiment, the disclosure provides a pharmaceutical composition consisting essentially of about 62.5 mg of Compound 1, about 125 mg of mannitol, about 8.33 mg of sodium carboxymethyl cellulose, about 7.08 mg of poloxamer 188, about 4.31 mg of L-histidine, about 41.7 mg of soy lecithin, and about 2.5 mL of sterile water for injection, USP.

In another embodiment, the disclosure provides a pharmaceutical composition consisting of about 62.5 mg of Compound 1, about 125 mg of mannitol, about 8.33 mg of sodium carboxymethyl cellulose, about 7.08 mg of poloxamer 188, about 4.31 mg of L-histidine, about 41.7 mg of soy lecithin, and about 2.5 mL of sterile water for injection, USP.

In another embodiment, the disclosure provides a pharmaceutical composition comprising about 120.2 mg of Compound 1, about 240.4 mg of mannitol, about 16 mg of sodium carboxymethyl cellulose, about 13.6 mg of poloxamer 188, about 8.3 mg of L-histidine, about 80.2 mg of soy lecithin, and about 2.5 mL of sterile water for injection, USP.

In another embodiment, the disclosure provides a pharmaceutical composition consisting essentially of about 120.2 mg of Compound 1, about 240.4 mg of mannitol, about 16 mg of sodium carboxymethyl cellulose, about 13.6 mg of poloxamer 188, about 8.3 mg of L-histidine, about 80.2 mg of soy lecithin, and about 2.5 mL of sterile water for injection, USP.

In another embodiment, the disclosure provides a pharmaceutical composition consisting of about 120.2 mg of Compound 1, about 240.4 mg of mannitol, about 16 mg of sodium carboxymethyl cellulose, about 13.6 mg of poloxamer 188, about 8.3 mg of L-histidine, about 80.2 mg of soy lecithin, and about 2.5 mL of sterile water for injection, USP.

In another embodiment, the disclosure provides a pharmaceutical composition comprising about 120.2 mg of Compound 1, about 120.2 mg of mannitol, about 8.0 mg of sodium carboxymethyl cellulose, about 6.8 mg of poloxamer 188, about 4.1 mg of L-histidine, about 40.1 mg of soy lecithin, and about 2.5 mL of sterile water for injection, USP.

In another embodiment, the disclosure provides a pharmaceutical composition consisting essentially of about 120.2 mg of Compound 1, about 120.2 mg of mannitol, about 8.0 mg of sodium carboxymethyl cellulose, about 6.8 mg of poloxamer 188, about 4.1 mg of L-histidine, about 40.1 mg of soy lecithin, and about 2.5 mL of sterile water for injection, USP.

In another embodiment, the disclosure provides a pharmaceutical composition consisting of about 120.2 mg of Compound 1, about 120.2 mg of mannitol, about 8.0 mg of sodium carboxymethyl cellulose, about 6.8 mg of poloxamer 188, about 4.1 mg of L-histidine, about 40.1 mg of soy lecithin, and about 2.5 mL of sterile water for injection, USP.

In another embodiment, the disclosure provides a pharmaceutical composition comprising lyophilate L1, L2, L3, L4, or L5, see table above, and 1 mL WFI USP, 1.5 mL WFI USP, 2.0 mL WFI USP, 2.5 mL WFI USP, 3.0 mL WFI USP, 3.5 mL WFI USP, 4.0 mL WFI USP, 4.5 mL WFI USP, or 5 mL WFI USP.

The pharmaceutical compositions described in this section are collectively referred to as a "Pharmaceutical Composition of the Disclosure."

III. Therapeutic Methods

In another embodiment, the disclosure provides a method for treating cancer in a subject in need thereof comprising subcutaneously administering a therapeutically effective amount of a Pharmaceutical Composition of the Disclosure to the subject.

In another embodiment, the disclosure provides a method for treating cancer in a subject in need thereof comprising subcutaneously administering a therapeutically effective amount of a Pharmaceutical Composition of the Disclosure to the subject in combination with one or more optional therapeutic agents.

In another embodiment, the disclosure provides a Pharmaceutical Composition of the Disclosure for use in treating cancer in a subject.

In another embodiment, the disclosure provides a Pharmaceutical Composition of the Disclosure for use in treating cancer in a subject, wherein the Pharmaceutical Composition of the Disclosure is to be subcutaneously administered in combination with one or more optional therapeutic agents.

In another embodiment, the Pharmaceutical Composition of the Disclosure is subcutaneously administered to the subject according to an intermittent dosing schedule. For example, the Pharmaceutical Composition of the Disclosure may be administered to a subject three days a week on non-consecutive days, e.g., Monday-Wednesday-Friday, or two days a week on non-consecutive days, e.g., Monday and Thursday.

In one embodiment, the cancer is a solid tumor.

In another embodiment, the cancer is a hematological cancer. In another embodiment, the hematological cancer is acute lymphocytic leukemia, chronic lymphocytic leukemia (including B-cell chronic lymphocytic leukemia), or acute myeloid leukemia.

In another embodiment, the cancer is any one or more of the cancers of Table 1.

TABLE 1

| | | | |
|---|---|---|---|
| adrenal cancer | acinic cell carcinoma | acoustic neuroma | acral lentigious melanoma |
| acrospiroma | acute eosinophilic leukemia | acute erythroid leukemia | acute lymphoblastic leukemia |
| acute megakaryoblastic leukemia | acute monocytic leukemia | acute promyelocytic leukemia | adenocarcinoma |
| adenoid cystic carcinoma | adenoma | adenomatoid odontogenic tumor | adenosquamous carcinoma |
| adipose tissue neoplasm | adrenocortical carcinoma | adult T-cell leukemia/lymphoma | aggressive NK-cell leukemia |
| AIDS-related lymphoma | alveolar rhabdomyosarcoma | alveolar soft part sarcoma | ameloblastic fibroma |
| anaplastic large cell lymphoma | anaplastic thyroid cancer | angioimmunoblastic T-cell lymphoma | angiomyolipoma |
| angiosarcoma | astrocytoma | atypical teratoid rhabdoid tumor | B-cell chronic lymphocytic leukemia |
| B-cell prolymphocytic leukemia | B-cell lymphoma | basal cell carcinoma | biliary tract cancer |
| bladder cancer | blastoma | bone cancer | Brenner tumor |
| Brown tumor | Burkitt's lymphoma | breast cancer | brain cancer |
| carcinoma | carcinoma in situ | carcinosarcoma | cartilage tumor |
| cementoma | myeloid sarcoma | chondroma | chordoma |
| choriocarcinoma | choroid plexus papilloma | clear-cell sarcoma of the kidney | craniopharyngioma |
| cutaneous T-cell lymphoma | cervical cancer | colorectal cancer | Degos disease |
| desmoplastic small round cell tumor | diffuse large B-cell lymphoma | dysembryoplastic neuroepithelial tumor | dysgerminoma |
| embryonal carcinoma | endocrine gland neoplasm | endodermal sinus tumor | enteropathy-associated T-cell lymphoma |
| esophageal cancer | fetus in fetu | fibroma | fibrosarcoma |
| follicular lymphoma | follicular thyroid cancer | ganglioneuroma | gastrointestinal cancer |
| germ cell tumor | gestational choriocarcinoma | giant cell fibroblastoma | giant cell tumor of the bone |
| glial tumor | glioblastoma multiforme | glioma | gliomatosis cerebri |

TABLE 1-continued

| | | | |
|---|---|---|---|
| glucagonoma | gonadoblastoma | granulosa cell tumor | gynandroblastoma |
| gallbladder cancer | gastric cancer | hairy cell leukemia | hemangioblastoma |
| head and neck cancer | hemangiopericytoma | hematological cancer | hepatoblastoma |
| hepatosplenic T-cell lymphoma | Hodgkin's lymphoma | non-Hodgkin's lymphoma | invasive lobular carcinoma |
| intestinal cancer | kidney cancer | laryngeal cancer | lentigo maligna |
| lethal midline carcinoma | leukemia | leydig cell tumor | liposarcoma |
| lung cancer | lymphangioma | lymphangiosarcoma | lymphoepithelioma |
| lymphoma | acute lymphocytic leukemia | acute myelogeous leukemia | chronic lymphocytic leukemia |
| liver cancer | small cell lung cancer | non-small cell lung cancer | MALT lymphoma |
| malignant fibrous histiocytoma | malignant peripheral nerve sheath tumor | malignant triton tumor | mantle cell lymphoma |
| marginal zone B-cell lymphoma | mast cell leukemia | mediastinal germ cell tumor | medullary carcinoma of the breast |
| medullary thyroid cancer | medulloblastoma | melanoma | meningioma |
| merkel cell cancer | mesothelioma | metastatic urothelial carcinoma | mixed Mullerian tumor |
| mucinous tumor | multiple myeloma | muscle tissue neoplasm | mycosis fungoides |
| myxoid liposarcoma | myxoma | myxosarcoma | nasopharyngeal carcinoma |
| neurinoma | neuroblastoma | neurofibroma | neuroma |
| nodular melanoma | ocular cancer | oligoastrocytoma | oligodendroglioma |
| oncocytoma | optic nerve sheath meningioma | optic nerve tumor | oral cancer |
| osteosarcoma | ovarian cancer | Pancoast tumor | papillary thyroid cancer |
| paraganglioma | pinealoblastoma | pineocytoma | pituicytoma |
| pituitary adenoma | pituitary tumor | plasmacytoma | polyembryoma |
| precursor T-lymphoblastic lymphoma | primary central nervous system lymphoma | primary effusion lymphoma | preimary peritoneal cancer |
| prostate cancer | pancreatic cancer | pharyngeal cancer | pseudomyxoma periotonei |
| renal cell carcinoma | renal medullary carcinoma | retinoblastoma | rhabdomyoma |
| rhabdomyosarcoma | Richter's transformation | rectal cancer | sarcoma |
| Schwannomatosis | seminoma | Sertoli cell tumor | sex cord-gonadal stromal tumor |
| signet ring cell carcinoma | skin cancer | small blue round cell tumors | small cell carcinoma |
| soft tissue sarcoma | somatostatinoma | soot wart | spinal tumor |
| splenic marginal zone lymphoma | squamous cell carcinoma | synovial sarcoma | Sezary's disease |
| small intestine cancer | squamous carcinoma | stomach cancer | T-cell lymphoma |
| testicular cancer | thecoma | thyroid cancer | transitional cell carcinoma |
| throat cancer | urachal cancer | urogenital cancer | urothelial carcinoma |
| uveal melanoma | uterine cancer | verrucous carcinoma | visual pathway glioma |
| vulvar cancer | vaginal cancer | Waldenstrom's macroglobulinemia | Warthin's tumor |
| Wilms' tumor | | | |

In another embodiment, the cancer is any one or more of the cancers of Table 2.

TABLE 2

| | |
|---|---|
| acute lymphocytic leukemia (ALL) | acute eosinophilic leukemia |
| acute myeloid leukemia (AML) | acute erythroid leukemia |
| chronic lymphocytic leukemia (CLL) | acute lymphoblastic leukemia |
| small lymphocytic lymphoma (SLL) | acute megakaryoblastic leukemia |
| multiple myeloma (MM) | acute monocytic leukemia |
| Hodgkins lymphoma (HL) | acute promyelocytic leukemia |
| non-Hodgkin's lymphoma (NHL) | acute myelogeous leukemia |
| mantle cell lymphoma (MCL) | B-cell prolymphocytic leukemia |

TABLE 2-continued

| | |
|---|---|
| marginal zone B-cell lymphoma | B-cell lymphoma |
| splenic marginal zone lymphoma | MALT lymphoma |
| follicular lymphoma (FL) | precursor T-lymphoblastic lymphoma |
| Waldenstrom's macroglobulinemia (WM) | T-cell lymphoma |
| diffuse large B-cell lymphoma (DLBCL) | mast cell leukemia |
| marginal zone lymphoma (MZL) | adult T cell leukemia/lymphoma |
| hairy cell leukemia (HCL) | aggressive NK-cell leukemia |
| Burkitt's lymphoma (BL) | angioimmunoblastic T-cell lymphoma |
| Richter's transformation | |

In another embodiment, the cancer is selected from the group consisting of squamous cell carcinoma of the head and neck (SCCHN), adenocarcinoma squamous cell carcinoma of the esophagus, adenocarcinoma of the stomach, adenocarcinoma of the colon, hepatocellular carcinoma, cholangiocarcinoma of the biliary system, adenocarcinoma of gall bladder, adenocarcinoma of the pancreas, ductal carcinoma in situ of the breast, adenocarcinoma of the breast, adenocarcinoma of the lungs, squamous cell carcinoma of the lungs, transitional cell carcinoma of the bladder, squamous cell carcinoma of the bladder, squamous cell carcinoma of the cervix, adenocarcinoma of the cervix, endometrial carcinoma, penile squamous cell carcinoma, and squamous cell carcinoma of the skin.

In another embodiment, a precancerous tumor is selected from the group consisting of leukoplakia of the head and neck, Barrett's esophagus, metaplasia of the stomach, adenoma of the colon, chronic hepatitis, bile duct hyperplasia, pancreatic intraepithelial neoplasia, atypical adenomatous hyperplasia of the lungs, dysplasia of the bladder, cervical initraepithelial neoplasia, penile intraepithelial neoplasia, and actinic keratosis of the skin.

In another embodiment, the cancer is selected from the group consisting of hepatocellular carcinoma, glioblastoma, lung cancer, breast cancer, head and neck cancer, prostate cancer, melanoma, and colorectal cancer.

In another embodiment, the cancer is selected from the group consisting of colorectal cancer, breast cancer, lymphoma, melanoma, kidney cancer, and lung cancer.

In another embodiment, the cancer has become resistant to conventional cancer treatments. The term "conventional cancer treatments" as used herein refers to any cancer drugs, biologics, or radiotherapy, or combination of cancer drugs and/or biologics and/or radiotherapy that have been tested and/or approved for therapeutic use in humans by the U.S. Food and Drug Administration, European Medicines Agency, or similar regulatory agency.

IV. Optional Therapeutic Agents

In some therapeutic methods and uses of the disclosure, a Pharmaceutical Composition of the Disclosure is administered to a subject having cancer as a single agent. In other therapeutic methods and uses of the disclosure, a Pharmaceutical Composition of the Disclosure is administered to a subject having cancer in combination with one or more optional therapeutic agents. In one embodiment, a Pharmaceutical Composition of the Disclosure is administered in combination with one optional therapeutic agent. In another embodiment, a Pharmaceutical Composition of the Disclosure is administered in combination with two optional therapeutic agents. In another embodiment, a Pharmaceutical Composition of the Disclosure is administered in combination with three optional therapeutic agents. Optional therapeutic agents useful in treating cancer patients include those known in the art as well as those developed in the future.

Optional therapeutic agents are administered in an amount to provide their desired therapeutic effect. The effective dosage range for each optional therapeutic agent is known in the art, and the optional therapeutic agent is administered to an individual in need thereof within such established ranges.

A Pharmaceutical Composition of the Disclosure and the optional therapeutic agent(s) can be administered separately as multi-unit doses in any order, e.g., wherein a Pharmaceutical Composition of the Disclosure is administered before the optional therapeutic agent(s), or vice versa. One or more doses of a Pharmaceutical Composition of the Disclosure and the optional therapeutic agent(s) can be administered to the subject.

In one embodiment, the optional therapeutic agent comprises one or more immune checkpoint inhibitors. Examples of immune checkpoint inhibitors include PD-1 inhibitors, PD-L1 inhibitors, CTLA-4 inhibitors, LAG3 inhibitors, TIM3 inhibitors, cd47 inhibitors, TIGIT inhibitors, and B7-H1 inhibitors. Thus, in one embodiment, the immune checkpoint inhibitor is selected from the group consisting of a PD-1 inhibitor, a PD-L1 inhibitor, a CTLA-4 inhibitor, a LAG3 inhibitor, a TIM3 inhibitor, and a cd47 inhibitor.

In another embodiment, the immune checkpoint inhibitor is a programmed cell death (PD-1) inhibitor. PD-1 is a T-cell coinhibitory receptor that plays a pivotal role in the ability of tumor cells to evade the host's immune system. Blockage of interactions between PD-1 and PD-L1, a ligand of PD-1, enhances immune function and mediates antitumor activity. Examples of PD-1 inhibitors include antibodies that specifically bind to PD-1. Particular anti-PD-1 antibodies include, but are not limited to nivolumab, pembrolizumab, STI-A1014, pidilzumab, and cemiplimab-rwlc. For a general discussion of the availability, methods of production, mechanism of action, and clinical studies of anti-PD-1 antibodies, see U.S. 2013/0309250, U.S. Pat. Nos. 6,808,710, 7,595,048, 8,008,449, 8,728,474, 8,779,105, 8,952,136, 8,900,587, 9,073,994, 9,084,776, and Naido et al., *British Journal of Cancer* 111:2214-19 (2014).

In another embodiment, the immune checkpoint inhibitor is a PD-L1 (also known as B7-H1 or CD274) inhibitor. Examples of PD-L1 inhibitors include antibodies that specifically bind to PD-L1. Particular anti-PD-L1 antibodies include, but are not limited to, avelumab, atezolizumab, durvalumab, and BMS-936559. For a general discussion of the availability, methods of production, mechanism of action, and clinical studies, see U.S. Pat. No. 8,217,149, U.S. 2014/0341917, U.S. 2013/0071403, WO 2015036499, and Naido et al., *British Journal of Cancer* 111:2214-19 (2014).

In another embodiment, the immune checkpoint inhibitor is a CTLA-4 inhibitor. CTLA-4, also known as cytotoxic T-lymphocyte antigen 4, is a protein receptor that down-regulates the immune system. CTLA-4 is characterized as a "brake" that binds costimulatory molecules on antigen-presenting cells, which prevents interaction with CD28 on T cells and also generates an overtly inhibitory signal that constrains T cell activation. Examples of CTLA-4 inhibitors include antibodies that specifically bind to CTLA-4. Particular anti-CTLA-4 antibodies include, but are not limited to, ipilimumab and tremelimumab. For a general discussion of the availability, methods of production, mechanism of action, and clinical studies, see U.S. Pat. Nos. 6,984,720, 6,207,156, and Naido et al., *British Journal of Cancer* 111:2214-19 (2014).

In another embodiment, the immune checkpoint inhibitor is a LAG3 inhibitor. LAG3, Lymphocyte Activation Gene 3, is a negative co-stimulatory receptor that modulates T cell homeostasis, proliferation, and activation. In addition, LAG3 has been reported to participate in regulatory T cells (Tregs) suppressive function. A large proportion of LAG3 molecules are retained in the cell close to the microtubule-organizing center, and only induced following antigen specific T cell activation. U.S. 2014/0286935. Examples of LAG3 inhibitors include antibodies that specifically bind to LAG3. Particular anti-LAG3 antibodies include, but are not limited to, GSK2831781. For a general discussion of the availability, methods of production, mechanism of action, and studies, see, U.S. 2011/0150892, U.S. 2014/0093511, U.S. 20150259420, and Huang et al., *Immunity* 21:503-13 (2004).

In another embodiment, the immune checkpoint inhibitor is a TIM3 inhibitor. TIM3, T-cell immunoglobulin and mucin domain 3, is an immune checkpoint receptor that functions to limit the duration and magnitude of $T_H1$ and $T_C1$ T-cell responses. The TIM3 pathway is considered a target for anticancer immunotherapy due to its expression on dysfunctional $CD8^+$ T cells and Tregs, which are two reported immune cell populations that constitute immunosuppression in tumor tissue. Anderson, *Cancer Immunology Research* 2:393-98 (2014). Examples of TIM3 inhibitors include antibodies that specifically bind to TIM3. For a general discussion of the availability, methods of production, mechanism of action, and studies of TIM3 inhibitors, see U.S. 20150225457, U.S. 20130022623, U.S. Pat. No. 8,522,156, Ngiow et al., *Cancer Res* 71: 6567-71 (2011), Ngiow, et al., *Cancer Res* 71:3540-51 (2011), and Anderson, *Cancer Immunology Res* 2:393-98 (2014).

In another embodiment, the immune checkpoint inhibitor is a cd47 inhibitor. See Unanue, E. R., *PNAS* 110:10886-87 (2013).

In another embodiment, the immune checkpoint inhibitor is a TIGIT inhibitor. See Harjunpää 1 and Guillerey, *Clin Exp Immunol* 200:108-119 (2019).

The one or more immune checkpoint inhibitors are administered to the subject in therapeutically effective amounts. These amounts are guided by standard clinical practice, e.g., according to the prescribing information associated with the immune checkpoint inhibitors.

For example, when the immune checkpoint inhibitor(s) is a monoclonal antibody, about 1 to about 2000 mg can be administered as an intravenous infusion every 2-4 weeks. For example, about 10 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1100 mg, about 1200 mg, about 1300 mg, about 1400 mg, about 1500 mg, about 1600 mg, about 1700 mg, about 1800 mg, about 1900 mg, or about 2000 mg of the antibody can be administered.

For example, when immune checkpoint inhibitor is nivolumab, 240 mg may be administered to the subject by intravenous infusion every two weeks, or 480 mg may be administered by intravenous infusion every for weeks.

For example, when the immune checkpoint inhibitors is pembrolizumab, 200 mg may be administered to the subject by intravenous infusion every three weeks, or 400 mg may be administered to the subject by intravenous infusion every six weeks.

For example, when the immune checkpoint inhibitors is avelumab, 800 mg may be administered to the subject by intravenous infusion every two weeks.

For example, when immune checkpoint inhibitors is atezolizumab, 840 mg may be administered by intravenous infusion every two weeks, or 1200 mg may be administered by intravenous infusion every three weeks, or 1680 mg may be administered by intravenous infusion every four weeks.

For example, when the immune checkpoint inhibitors is ipilumumab, 3 mg/kg may be administered to the subject by intravenous infusion every three weeks.

For example, when the immune checkpoint inhibitors is tremelimumab, 3 to 20 mg/kg may be administered to the subject by intravenous infusion every four weeks.

For example, when immune checkpoint inhibitors is GSK2831781, 1.5 to 5 mg/kg may be administered to the subject by intravenous infusion every 2-4 weeks.

Representative dosing regimens for certain immune checkpoint inhibitors to treat certain cancers are provided in Table 3.

TABLE 3

| Drug | Body-Weight-Based Dose | Flat Dose | Clinical Applications |
|---|---|---|---|
| Ipilimumab | 3 mg/kg Q3 W<br>10 mg/kg Q3 W | | Metastatic melanoma<br>Cutaneous melanoma<br>Advanced renal cell carcinoma |
| Nivolumab | 3 mg/kg Q2 W | 240 mg Q2 W<br>480 mg Q4 W | Metastatic melanoma<br>Metastatic NSCLC<br>Hodgkin lymphoma<br>Advanced renal cell carcinoma<br>Advanced or metastatic urothelial carcinoma<br>Metastatic colorectal cancer<br>Hepatocellular carcinoma |
| Pembrolizumab | 2 mg/kg Q3 W | 200 mg Q3 W<br>400 mg Q6 W | Melanoma<br>NSCLC |

TABLE 3-continued

| Drug | Body-Weight-Based Dose | Flat Dose | Clinical Applications |
|---|---|---|---|
| | | | Head and neck squamous cell cancer<br>Classical Hodgkin lymphoma<br>Primary mediastinal large b-cell lymphoma<br>Urothelial carcinoma<br>Microsatellite instability-high cancer<br>Gastric cancer<br>Cervical cancer<br>Hepatocellular carcinoma<br>Merkel cell carcinoma |
| Cemiplimab | | 350 mg Q3 W | Metastatic CSCC<br>Locally advanced CSCC |
| Atezolizumab | | 840 mg Q2 W<br>1200 mg Q3 W<br>1680 mg Q4 W | Urothelical Carcinoma<br>NSCLC<br>TNBC<br>Metastatic treatment of TNBC |
| Avelumab | 10 mg/kg Q2 W | 800 mg Q2 W | Metastatic Merkel cell carcinoma<br>Advanced or metastatic urothelial carcinoma<br>Advanced renal cell carcinoma (+axitinib) |
| Durvalumab | 10 mg/kg Q2 W | 750 mg Q2 W<br>1500 mg Q4 W | Locally advanced or metastatic urothelical carcinoma<br>Unresectable stage III NSCLC |

In one embodiment, the immune checkpoint inhibitor(s) is an antibody, and 1 to 20 mg/kg is administered to the subject by intravenous infusion every 2-4 weeks. In another embodiment, 20-2000 mg of the antibody is administered to the subject by intravenous infusion every 2-4 weeks. In another embodiment, Compound 1 is administered prior to administration of the antibody. In another embodiment, Compound 1 is administered to the subject 1, 2, 3, 4, 5, 6, or 7 days prior to the day of administration of the antibody. In another embodiment, Compound 1 is administered to the subject the day the antibody is administered. In another embodiment, Compound 1 is administered to the subject 1, 2, 3, 4, 5, 6, or 7 days after the day of administration of the antibody.

For example, the subject receives pembrolizumab administered by intravenous infusion every three weeks and Compound 1 administered two times a week by subcutaneous infusion, wherein the first dose of Compound 1 is administered prior to the first dose of pembrolizumab, the first dose of Compound 1 is administered on the same day as the first dose of pembrolizumab, or the first dose of Compound 1 is administered after to the first dose of pembrolizumab, e.g., until disease progression or until there is no therapeutic benefit.

For example, the subject receives nivolumab administered by intravenous infusion every two weeks and Compound 1 administered two times a week by subcutaneous infusion, wherein the first dose of Compound 1 is administered prior to the first dose of nivolumab, the first dose of Compound 1 is administered on the same day as the first dose of nivolumab, or the first dose of Compound 1 is administered after to the first dose of nivolumab, e.g., until disease progression or until there is no therapeutic benefit.

In another embodiment, the treatment of the cancer patient with Compound 1 and one or more an immune checkpoint inhibitors induces anti-proliferative response faster than when the immune checkpoint inhibitor is administered alone.

The term "antibody" is meant to include intact monoclonal antibodies, polyclonal antibodies, multispecific antibodies formed from at least two intact antibodies, and antibody fragments, so long as they exhibit the desired biological activity. In another embodiment, "antibody" is meant to include soluble receptors that do not possess the Fc portion of the antibody. In one embodiment, the antibodies are humanized monoclonal antibodies and fragments thereof made by means of recombinant genetic engineering.

Another class of immune checkpoint inhibitors include polypeptides that bind to and block PD-1 receptors on T-cells without triggering inhibitor signal transduction. Such peptides include B7-DC polypeptides, B7-H1 polypeptides, B7-1 polypeptides and B7-2 polypeptides, and soluble fragments thereof, as disclosed in U.S. Pat. No. 8,114,845.

Another class of immune checkpoint inhibitors include compounds with peptide moieties that inhibit PD-1 signaling. Examples of such compounds are disclosed in U.S. Pat. No. 8,907,053.

Another class of immune checkpoint inhibitors include inhibitors of certain metabolic enzymes, such as indoleamine 2,3 dioxygenase (IDO), which is expressed by infiltrating myeloid cells and tumor cells, and isocitrate dehydrogenase (IDH), which is mutated in leukemia cells. Mutants of the IDH enzyme lead to increased levels of 2-hydroxyglutarate (2-HG), which prevent myeloid differentiation. Stein et al., *Blood* 130:722-31 (2017); Wouters, *Blood* 130:693-94 (2017). Particular mutant IDH blocking agents include, but are not limited to, ivosidenib and enasidenib mesylate. Dalle and DiNardo, *Ther Adv Hematol* 9(7):163-73 (2018); Nassereddine et al., *Onco Targets Ther* 12:303-08 (2018). The IDO enzyme inhibits immune responses by depleting amino acids that are necessary for anabolic functions in T cells or through the synthesis of particular natural ligands for cytosolic receptors that are able to alter lymphocyte functions. Pardoll, *Nature Reviews. Cancer* 12:252-64 (2012); Löb, *Cancer Immunol Immunother* 58:153-57 (2009). Particular IDO blocking agents include, but are not limited to, levo-1-methyl typtophan (L-1MT) and 1-methyl-tryptophan (1MT). Qian et al., *Cancer Res* 69:5498-504 (2009); and Löb et al., *Cancer Immunol Immunother* 58:153-7 (2009).

In one embodiment, the immune checkpoint inhibitor is nivolumab, pembrolizumab, pidilizumab, STI-A1110, avelumab, atezolizumab, durvalumab, STI-A1014, ipilimumab, tremelimumab, GSK2831781, BMS-936559 or MED14736.

In another embodiment, the optional therapeutic agent is an epigenetic drug. As used herein, the term "epigenetic drug" refers to a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, but are not limited to, vorinostat and panobinostat lactate.

Additional examples of conventional therapies and anticancer agents that can be used in combination with a Pharmaceutical Composition of the Disclosure include surgery, radiotherapy, e.g., gamma-radiation, neutron beam radiotherapy, electron beam radiotherapy, proton therapy, brachytherapy, and systemic radioactive isotopes, endocrine therapy, a biologic response modifier, e.g., an interferon, an interleukin, tumor necrosis factor (TNF), hyperthermia and cryotherapy, an agent to attenuate any adverse effect (e.g., an antiemetic), and any other approved biologic therapy or chemotherapy, e.g., a treatment regimen that uses drugs to stop the growth of cancer cells, either by killing the cells or by stopping them from dividing. Chemotherapy may be given by mouth, injection, or infusion, or on the skin, depending on the type and stage of the cancer being treated.

Nonlimiting exemplary antiproliferative compounds include an aromatase inhibitor; an anti-estrogen; an anti-androgen; a gonadorelin agonist; a topoisomerase I inhibitor; a topoisomerase II inhibitor; a microtubule active agent; an alkylating agent, e.g., temozolomide; a retinoid, a carontenoid, or a tocopherol; a cyclooxygenase inhibitor; an MMP inhibitor; an mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a compound used in the treatment of hematologic malignancies; a Flt-3 inhibitor; an Hsp90 inhibitor; a kinesin spindle protein inhibitor; a MEK inhibitor; an antitumor antibiotic; a nitrosourea; a compound targeting/decreasing protein or lipid kinase activity, a compound targeting/decreasing protein or lipid phosphatase activity, or any further anti-angiogenic compound.

Nonlimiting exemplary aromatase inhibitors include steroids, such as atamestane, exemestane, and formestane, and non-steroids, such as aminoglutethimide, roglethimide, pyridoglutethimide, trilostane, testolactone, ketokonazole, vorozole, fadrozole, anastrozole, and letrozole.

Nonlimiting anti-estrogens include tamoxifen, fulvestrant, raloxifene, and raloxifene hydrochloride. Anti-androgens include, but are not limited to, bicalutamide and apalutamide. Gonadorelin agonists include, but are not limited to, abarelix, goserelin, and goserelin acetate.

Nonlimiting exemplary topoisomerase I inhibitors include topotecan, gimatecan, irinotecan, camptothecin and its analogues, 9-nitrocamptothecin, and the macromolecular camptothecin conjugate PNU-166148. Topoisomerase II inhibitors include, but are not limited to, anthracyclines, such as doxorubicin, daunorubicin, epirubicin, idarubicin, and nemorubicin; anthraquinones, such as mitoxantrone and losoxantrone; and podophillotoxines, such as etoposide and teniposide.

Microtubule active agents include microtubule stabilizing, microtubule destabilizing compounds, and microtubulin polymerization inhibitors including, but not limited to, taxanes, such as paclitaxel and docetaxel; discodermolides; cochicine and epothilones and derivatives thereof.

Nonlimiting exemplary alkylating agents include cyclophosphamide, ifosfamide, melphalan, trabectedin, and nitrosoureas, such as carmustine and lomustine.

Nonlimiting exemplary matrix metalloproteinase inhibitors ("MMP inhibitors") include collagen peptidomimetic and nonpeptidomimetic inhibitors, tetracycline derivatives, batimastat, marimastat, prinomastat, metastat, BMS-279251, BAY 12-9566, TAA211, MMI270B, and AAJ996.

Nonlimiting exemplary mTOR inhibitors include compounds that inhibit the mammalian target of rapamycin (mTOR) and possess antiproliferative activity such as sirolimus, everolimus, CCI-779, and ABT578.

Nonlimiting exemplary antimetabolites include 5-fluorouracil (5-FU), capecitabine, gemcitabine, DNA demethylating compounds, such as 5-azacytidine and decitabine, methotrexate and edatrexate, and folic acid antagonists, such as pemetrexed.

Nonlimiting exemplary platin compounds include carboplatin, cis-platin, cisplatinum, and oxaliplatin.

Nonlimiting exemplary methionine aminopeptidase inhibitors include bengamide or a derivative thereof and PPI-2458.

Nonlimiting exemplary bisphosphonates include etridonic acid, clodronic acid, tiludronic acid, pamidronic acid, alendronic acid, ibandronic acid, risedronic acid, and zoledronic acid.

Nonlimiting exemplary heparanase inhibitors include compounds that target, decrease, or inhibit heparin sulfate degradation, such as PI-88 and OGT2115.

Nonlimiting exemplary compounds which target, decrease, or inhibit the oncogenic activity of Ras include farnesyl transferase inhibitors, such as L-744832, DK8G557, tipifarnib, and lonafarnib.

Nonlimiting exemplary telomerase inhibitors include compounds that target, decrease, or inhibit the activity of telomerase, such as compounds that inhibit the telomerase receptor, such as telomestatin.

Nonlimiting exemplary proteasome inhibitors include compounds that target, decrease, or inhibit the activity of the proteasome including, but not limited to, bortezomib. In some embodiments, the proteasome inhibitor is carfilzomib or ixazomib.

Nonlimiting exemplary FMS-like tyrosine kinase inhibitors, which are compounds targeting, decreasing or inhibiting the activity of FMS-like tyrosine kinase receptors (Flt-3R), include gilteritinib, interferon, I-β-D-arabinofuransylcytosine (ara-c), and bisulfan; and ALK inhibitors, which are compounds that target, decrease, or inhibit anaplastic lymphoma kinase, include alectinib, brigatinib, and lorlatinib.

Nonlimiting exemplary Flt-3 inhibitors include PKC412, midostaurin, a staurosporine derivative, SU11248, MLN518, and gilteritinib.

Nonlimiting exemplary HSP90 inhibitors include compounds targeting, decreasing, or inhibiting the intrinsic ATPase activity of HSP90; or degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins, or antibodies that inhibit the ATPase activity of HSP90, such as 17-allylamino,17-demethoxygeldanamycin (17AAG), a geldanamycin derivative; other geldanamycin related compounds; radicicol and HDAC inhibitors.

Nonlimiting exemplary protein tyrosine kinase and/or serine and/or threonine kinase inhibitors or lipid kinase inhibitors, include a) a compound targeting, decreasing, or inhibiting the activity of the platelet-derived growth factor-receptors (PDGFR), such as a compound that targets, decreases, or inhibits the activity of PDGFR, including olaratumab and N-phenyl-2-pyrimidine-amine derivatives, such as imatinib, SUlOl, SU6668, and GFB-111; b) a compound targeting, decreasing, or inhibiting the activity of the fibroblast growth factor-receptors (FGFR), such as erdafitinib and lenvatinib; c) a compound targeting, decreasing, or inhibiting the activity of the insulin-like growth factor receptor I (IGF-IR), such as brigatinib; d) a compound targeting, decreasing, or inhibiting the activity of the vascular endothelial growth factor-receptors (VEGFR), such as lenvatinib; e) a compound targeting, decreasing, or inhibiting the activity of the Trk receptor tyrosine kinase family, or ephrin B4 inhibitors, such as larotrectinib; f) a compound targeting, decreasing, or inhibiting the activity of the Axl receptor tyrosine kinase family; g) a compound targeting, decreasing, or inhibiting the activity of the Ret receptor tyrosine kinase, such as alectinib; h) a compound targeting, decreasing, or inhibiting the activity of the Kit/SCFR receptor tyrosine kinase, such as imatinib; i) a compound targeting, decreasing, or inhibiting the activity of the c-Kit receptor tyrosine kinases, such as imatinib; j) a compound targeting, decreasing, or inhibiting the activity of members of the c-Abl family, their gene-fusion products (e.g. Bcr-Abl kinase) and mutants, such as an N-phenyl-2-pyrimidine-amine derivative, such as imatinib or nilotinib; PD180970; AG957; NSC 680410; PD173955; or dasatinib; k) a compound targeting, decreasing, or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK), such as a staurosporine derivative disclosed in U.S. Pat. No. 5,093,330, such as midostaurin; examples of further compounds include UCN-01, safingol, BAY 43-9006, bryostatin 1, perifosine; ilmofosine; RO 318220 and RO 320432; GO 6976; Isis 3521; LY333531/LY379196; a isochinoline compound; a farnesyl transferase inhibitor; PD184352 or QAN697, or AT7519; abemaciclib; binimetinib; cobimetinib; encorafenib; neratinib; palbociclib; ribociclib; l) a compound targeting, decreasing or inhibiting the activity of a protein-tyrosine kinase, such as acalabrutinib, imatinib mesylate or a tyrphostin, such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl) methyl]amino}-benzoic acid adamantyl ester; NSC 680410, adaphostin); m) a compound targeting, decreasing, or inhibiting the activity of the epidermal growth factor family of receptor tyrosine kinases (EGFR, ErbB2, ErbB3, ErbB4 as homo- or heterodimers) and their mutants, such as brigatinib, CP 358774, ZD 1839, ZM 105180; trastuzumab, cetuximab, gefitinib, erlotinib, osimertinib, dacomitinib, necitumumab, neratinib, OSI-774, C1-1033, EKB-569, GW-2016, antibodies EL1, E2.4, E2.5, E6.2, E6.4, E2.11, E6.3 and E7.6.3, and 7H-pyrrolo-[2,3-d]pyrimidine derivatives; n) a compound targeting, decreasing or inhibiting the activity of a phosphatidylinositol 3-kinase (PI3K), such as alpelisib, copanlisib, and duvelisib; and o) a compound targeting, decreasing, or inhibiting the activity of the c-Met receptor.

Nonlimiting exemplary compounds that target, decrease, or inhibit the activity of a protein or lipid phosphatase include inhibitors of phosphatase 1, phosphatase 2A, or CDC25, such as okadaic acid or a derivative thereof.

Further anti-angiogenic compounds include compounds having another mechanism for their activity unrelated to protein or lipid kinase inhibition, e.g., thalidomide and TNP-470.

Additional, nonlimiting, exemplary chemotherapeutic compounds, one or more of which may be used in combination with a Pharmaceutical Composition of the Disclosure include: avastin, daunorubicin, adriamycin, Ara-C, VP-16, teniposide, mitoxantrone, idarubicin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, 2-hydroxy-1H-isoindole-1,3-dione derivatives, 1-(4-chloroanilino)-4-(4-pyridylmethyl)phthalazine or a pharmaceutically acceptable salt thereof, 1-(4-chloroanilino)-4-(4-pyridylmethyl)phthalazine succinate, angiostatin, endostatin, anthranilic acid amides, ZD4190, ZD6474, SU5416, SU6668, bevacizumab, rhuMAb, rhuFab, macugon; FLT-4 inhibitors, FLT-3 inhibitors, VEGFR-2 IgGI antibody, RPI 4610, porfimer sodium, anecortave, triamcinolone, hydrocortisone, 11-a-epihydrocotisol, cortex olone, 17a-hydroxyprogesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA, and siRNA.

A number of suitable optional therapeutic, e.g., anticancer, agents, are contemplated for use in the therapeutic methods provided herein. Indeed, the methods provided herein can include, but are not limited to, administration of numerous optional therapeutic agents such as: agents that induce apoptosis; polynucleotides (e.g., antisense, ribozymes, siRNA); polypeptides (e.g., enzymes and antibodies); biological mimetics (e.g., gossypol or BH3 mimetics); agents that bind (e.g., oligomerize or complex) with a Bcl-2 family protein such as Bax; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-$\alpha$) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-$\kappa$B modulators; anti-CDK compounds; HDAC inhibitors; and the like. Numerous other examples of optional therapeutic agents such as chemotherapeutic compounds and anticancer therapies suitable for co-administration with the disclosed compounds are known to those skilled in the art.

In certain embodiments, optional therapeutic agents comprise agents that induce or stimulate apoptosis. Agents that induce or stimulate apoptosis include, for example, agents that interact with or modify DNA, such as by intercalating, cross-linking, alkylating, or otherwise damaging or chemically modifying DNA. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-R1 or TRAIL-R2); kinase inhibitors (e.g., epidermal growth factor receptor (EGFR) kinase inhibitor). Additional anticancer agents include: vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen); anti-androgens (e.g., flutamide, apalutamide, bicalutamide, finasteride, aminoglutethamide, ketoconazole, and corticosteroids); BCL-2 inhibitors (e.g., venetoclax); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the therapeutic methods provided herein include administering to a subject having cancer (a cancer patient) therapeutically effective amounts of a Pharmaceutical Composition of the Disclosure, an immune checkpoint inhibitor, and at least one additional optional therapeutic agent, e.g., an anti-hyperproliferative or antineoplastic agent selected from alkylating agents, antimetabolites, and natural products (e.g., herbs and other plant and/or animal derived compounds).

Alkylating agents suitable for use in the present methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyltriazenoimidazolecarboxamide).

In some embodiments, antimetabolites suitable for use in the present methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the methods of the present disclosure include, but are not limited to: 1) *vinca* alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the therapeutic methods of the present disclosure. For example, the U.S. Food and Drug Administration (FDA) maintains a formulary of oncolytic agents approved for use in the United States. International counterpart agencies to the FDA maintain similar formularies. Those skilled in the art will appreciate that the "product labels" required on all U.S. approved chemotherapeutics describe approved indications, dosing information, toxicity data, and the like, for the exemplary agents.

Anticancer agents further include compounds which have been identified to have anticancer activity. Examples include, but are not limited to, 3-AP, 12-O-tetradecanoylphorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calaspargase pegol-mknl, calcitriol, CCI-779, CDB-2914, cefixime, cetuximab, CG0070, cilengitide, clofarabine, combretastatin A4 phosphate, CP-675,206, CP-724,714, CpG 7909, curcumin, daratumumab, decitabine, DENSPM, dinutuximab, doxercalciferol, E7070, E7389, ecteinascidin 743, efaproxiral, eflornithine, EKB-569, elotuzumab, enzastaurin, erlotinib, exisulind, fenretinide, flavopiridol, fludarabine, flutamide, fotemustine, FR901228, G17DT, galiximab, gefitinib, genistein, glasdegib, glufosfamide, GTI-2040, histrelin, HKI-272, homoharringtonine, HSPPC-96, hu14.18-interleukin-2 fusion protein, HuMax-CD4, iloprost, imiquimod, infliximab, inotuzumab ozogamicin, interleukin-12, IPI-504, irofulven, ixabepilone, lapatinib, lenalidomide, lestaurtinib, leuprolide, LMB-9 immunotoxin, lonafarnib, luniliximab, lutetium Lu 177 dotatate, mafosfamide, MB07133, MDX-010, MLN2704, mogamulizumab-kpkc, monoclonal antibody 3F8, monoclonal antibody J591, motexafin, moxetumomab pasudotox-tdfk, MS-275, MVA-MUC1-IL2, nilutamide, niraparib, nitrocamptothecin, nolatrexed dihydrochoride, nolvadex, NS-9, O6-benzylguanine, oblimersen sodium, ONYX-015, oregovomab, OSF-774, panitumumab, paraplatin, PD-0325901, pemetrexed, PHY96, pioglitazone, pirfenidone, pixantrone, polatuzumab vedotin-piiq, P)-341, PSC 833, PXD101, pyrazoloacridine, R115777, RAD001, ranpirnase, rebeccamycin analogue, rhuAngiostatin protein, rhuMab 2C4, rosiglitazone, rubitecan, rucaparib, S-1, S-8184, satraplatin, SB-, 15992, SGN-0010, SGN-40, sonidegib, sorafenib, SR31747A, ST1571, SU011248, suberoylanilide hydroxamic acid, suramin, tagraxofusp-erzs, talabostat, talampanel, talazoparib, tariquidar, temsirolimus, TGFa-PE38 immunotoxin, thalidomide, thymalfasin, tipifarnib, tirapazamine, TLK286, trabectedin, trifluridine and tipiracil hydrochloride, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

In one embodiment, the optional therapeutic agent comprises one of the anti-cancer drugs or anti-cancer drug combinations listed in Table 5.

TABLE 5

| | | | |
|---|---|---|---|
| Abemaciclib | Abiraterone Acetate | Abraxane (Paclitaxel Albumin-stabilized Nanoparticle Formulation) | ABVD |
| ABVE | ABVE-PC | AC | Acalabrutinib |
| AC-T | Actemra (Tocilizumab) | Adcetris (Brentuximab Vedotin) | ADE |
| Ado-Trastuzumab Emtansine | Adriamycin (Doxorubicin Hydrochloride) | Afatinib Dimaleate | Afinitor (Everolimus) |
| Akynzeo (Netupitant and Palonosetron Hydrochloride) | Aldara (Imiquimod) | Aldesleukin | Alecensa (Alectinib) |
| Alectinib | Alemtuzumab | Alimta (Pemetrexed Disodium) | Aliqopa (Copanlisib Hydrochloride) |
| Alkeran for Injection (Melphalan Hydrochloride) | Alkeran Tablets (Melphalan) | Aloxi (Palonosetron Hydrochloride) | Alunbrig (Brigatinib) |
| Ameluz (Aminolevulinic Acid) | Amifostine | Aminolevulinic Acid | Anastrozole |
| Apalutamide | Aprepitant | Aranesp (Darbepoetin Alfa) | Aredia (Pamidronate Disodium) |
| Arimidex (Anastrozole) | Aromasin (Exemestane) | Arranon (Nelarabine) | Arsenic Trioxide |
| Arzerra (Ofatumumab) | Asparaginase Erwinia chrysanthemi | Atezolizumab | Avastin (Bevacizumab) |
| Avelumab | Axicabtagene Ciloleucel | Axitinib | Azacitidine |
| Azedra (Iobenguane I 131) | Bavencio (Avelumab) | BEACOPP | Beleodaq (Belinostat) |
| Belinostat | Bendamustine Hydrochloride | Bendeka (Bendamustine Hydrochloride) | BEP |
| Besponsa (Inotuzumab Ozogamicin) | Bevacizumab | Bexarotene | Bicalutamide |
| BICNU (Carmustine) | Binimetinib | Bleomycin | Blinatumomab |
| Blincyto (Blinatumomab) | Bortezomib | Bosulif (Bosutinib) | Bosutinib |
| Braftovi (Encorafenib) | Brentuximab Vedotin | Brigatinib | BuMel |
| Busulfan | Busulfex (Busulfan) | Cabazitaxel | Cabometyx (Cabozantinib-S-Malate) |
| Cabozantinib-S-Malate | CAF | Calquence (Acalabrutinib) | Campath (Alemtuzumab) |
| Camptosar (Irinotecan Hydrochloride) | Capecitabine | CAPOX | Carac (Fluorouracil--Topical) |
| Carboplatin | CARBOPLATIN-TAXOL | Carfilzomib | Carmustine |
| Carmustine Implant | Casodex (Bicalutamide) | CEM | Cemiplimab-rwlc |
| Ceritinib | Cerubidine (Daunorubicin Hydrochloride) | Cervarix (Recombinant HPV Bivalent Vaccine) | Cetuximab |
| CEV | Chlorambucil | CHLORAMBUCIL-PREDNISONE | CHOP |
| Cisplatin | Cladribine | Clofarabine | Clolar (Clofarabine) |
| CMF | Cobimetinib | Cometriq (Cabozantinib-S-Malate) | Copanlisib Hydrochloride |
| COPDAC | Copiktra (Duvelisib) | COPP | COPP-ABV |
| Cosmegen (Dactinomycin) | Cotellic (Cobimetinib) | Crizotinib | CVP |
| Cyclophosphamide | Cyramza (Ramucirumab) | Cytarabine | Cytarabine Liposome |

TABLE 5-continued

| | | | |
|---|---|---|---|
| Cytosar-U (Cytarabine) | Dabrafenib | Dacarbazine | Dacogen (Decitabine) |
| Dacomitinib | Dactinomycin | Daratumumab | Darbepoetin Alfa |
| Darzalex (Daratumumab) | Dasatinib | Daunorubicin Hydrochloride | Daunorubicin Hydrochloride and Cytarabine Liposome |
| Decitabine | Defibrotide Sodium | Defitelio (Defibrotide Sodium) | Degarelix |
| Denileukin Diftitox | Denosumab | DepoCyt (Cytarabine Liposome) | Dexamethasone |
| Dexrazoxane Hydrochloride | Dinutuximab | Docetaxel | Doxil (Doxorubicin Hydrochloride Liposome) |
| Doxorubicin Hydrochloride | Doxorubicin Hydrochloride Liposome | Dox-SL (Doxorubicin Hydrochloride Liposome) | Durvalumab |
| Duvelisib | Efudex (Fluorouracil--Topical) | Eligard (Leuprolide Acetate) | Elitek (Rasburicase) |
| Ellence (Epirubicin Hydrochloride) | Elotuzumab | Eloxatin (Oxaliplatin) | Eltrombopag Olamine |
| Emend (Aprepitant) | Empliciti (Elotuzumab) | Enasidenib Mesylate | Encorafenib |
| Enzalutamide | Epirubicin Hydrochloride | EPOCH | Epoetin Alfa |
| Epogen (Epoetin Alfa) | Erbitux (Cetuximab) | Eribulin Mesylate | Erivedge (Vismodegib) |
| Erleada (Apalutamide) | Erlotinib Hydrochloride | Erwinaze (Asparaginase Erwinia chrysanthemi) | Ethyol (Amifostine) |
| Etopophos (Etoposide Phosphate) | Etoposide | Etoposide Phosphate | Evacet (Doxorubicin Hydrochloride Liposome) |
| Everolimus | Evista (Raloxifene Hydrochloride) | Evomela (Melphalan Hydrochloride) | Exemestane |
| 5-FU (Fluorouracil Injection) | 5-FU (Fluorouracil--Topical) | Fareston (Toremifene) | Farydak (Panobinostat lactate) |
| Faslodex (Fulvestrant) | FEC | Femara (Letrozole) | Filgrastim |
| Firmagon (Degarelix) | Fludarabine Phosphate | Fluoroplex (Fluorouracil--Topical) | Fluorouracil Injection |
| Fluorouracil--Topical | Flutamide | FOLFIRI | FOLFIRI-BEVACIZUMAB |
| FOLFIRI-CETUXIMAB | FOLFIRINOX | FOLFOX | Folotyn (Pralatrexate) |
| Fostamatinib Disodium | FU-LV | Fulvestrant | Fusilev (Leucovorin Calcium) |
| Gardasil (Recombinant HPV Quadrivalent Vaccine) | Gardasil 9 (Recombinant HPV Nonavalent Vaccine) | Gazyva (Obinutuzumab) | Gefitinib |
| Gemcitabine Hydrochloride | GEMCITABINE-CISPLATIN | GEMCITABINE-OXALIPLATIN | Gemtuzumab Ozogamicin |
| Gemzar (Gemcitabine Hydrochloride) | Gilotrif (Afatinib Dimaleate) | Gleevec (Imatinib Mesylate) | Gliadel Wafer (Carmustine Implant) |
| Glucarpidase | Goserelin Acetate | Granisetron | Granisetron Hydrochloride |
| Granix (Filgrastim) | Halaven (Eribulin Mesylate) | Hemangeol (Propranolol Hydrochloride) | Herceptin (Trastuzumab) |
| HPV Bivalent Vaccine, Recombinant | HPV Nonavalent Vaccine, Recombinant | HPV Quadrivalent Vaccine, Recombinant | Hycamtin (Topotecan Hydrochloride) |
| Hydrea (Hydroxyurea) | Hydroxyurea | Hyper-CVAD | Ibrance (Palbociclib) |
| Ibritumomab Tiuxetan | Ibrutinib | ICE | Iclusig (Ponatinib Hydrochloride) |
| Idarubicin Hydrochloride | Idelalisib | Idhifa (Enasidenib Mesylate) | Ifex (Ifosfamide) |
| Ifosfamide | IL-2 (Aldesleukin) | Imatinib Mesylate | Imbruvica (Ibrutinib) |
| Imfinzi (Durvalumab) | Imiquimod | Imlygic (Talimogene Laherparepvec) | Inlyta (Axitinib) |
| Inotuzumab | Interferon Alfa- | Interleukin-2 | Intron A |

TABLE 5-continued

| | | | |
|---|---|---|---|
| Ozogamicin | 2b, Recombinant | (Aldesleukin) | (Recombinant Interferon Alfa-2b) |
| Iobenguane I 131 | Ipilimumab | Iressa (Gefitinib) | Irinotecan Hydrochloride |
| Irinotecan Hydrochloride Liposome | Istodax (Romidepsin) | Ivosidenib | Ixabepilone |
| Ixazomib Citrate | Ixempra (Ixabepilone) | Jakafi (Ruxolitinib Phosphate) | JEB |
| Jevtana (Cabazitaxel) | Kadcyla (Ado-Trastuzumab Emtansine) | Kepivance (Palifermin) | Keytruda (Pembrolizumab) |
| Kisqali (Ribociclib) | Kymriah (Tisagenlecleucel) | Kyprolis (Carfilzomib) | Lanreotide Acetate |
| Lapatinib Ditosylate | Larotrectinib Sulfate | Lartruvo (Olaratumab) | Lenalidomide |
| Lenvatinib Mesylate | Lenvima (Lenvatinib Mesylate) | Letrozole | Leucovorin Calcium |
| Leukeran (Chlorambucil) | Leuprolide Acetate | Levulan Kerastik (Aminolevulinic Acid) | Libtayo (Cemiplimab-rwlc) |
| LipoDox (Doxorubicin Hydrochloride Liposome) | Lomustine | Lonsurf (Trifluridine and Tipiracil Hydrochloride) | Lorbrena (Lorlatinib) |
| Lorlatinib | Lumoxiti (Moxetumomab Pasudotox-tdfk) | Lupron (Leuprolide Acetate) | Lupron Depot (Leuprolide Acetate) |
| Lutathera (Lutetium Lu 177-Dotatate) | Lutetium (Lu 177-Dotatate) | Lynparza (Olaparib) | Marqibo (Vincristine Sulfate Liposome) |
| Matulane (Procarbazine Hydrochloride) | Mechlorethamine Hydrochloride | Megestrol Acetate | Mekinist (Trametinib) |
| Mektovi (Binimetinib) | Melphalan | Melphalan Hydrochloride | Mercaptopurine |
| Mesna | Mesnex (Mesna) | Methotrexate | Methylnaltrexone Bromide |
| Midostaurin | Mitomycin C | Mitoxantrone Hydrochloride | Mogamulizumab-kpkc |
| Moxetumomab Pasudotox-tdfk | Mozobil (Plerixafor) | Mustargen (Mechlorethamine Hydrochloride) | MVAC |
| Myleran (Busulfan) | Mylotarg (Gemtuzumab Ozogamicin) | Nanoparticle Paclitaxel (Paclitaxel Albumin-stabilized Nanoparticle Formulation) | Navelbine (Vinorelbine Tartrate) |
| Necitumumab | Nelarabine | Neratinib Maleate | Nerlynx (Neratinib Maleate) |
| Netupitant and Palonosetron Hydrochloride | Neulasta (Pegfilgrastim) | Neupogen (Filgrastim) | Nexavar (Sorafenib Tosylate) |
| Nilandron (Nilutamide) | Nilotinib | Nilutamide | Ninlaro (Ixazomib Citrate) |
| Niraparib Tosylate Monohydrate | Nivolumab | Nplate (Romiplostim) | Obinutuzumab |
| Odomzo (Sonidegib) | OEPA | Ofatumumab | OFF |
| Olaparib | Olaratumab | Omacetaxine Mepesuccinate | Oncaspar (Pegaspargase) |
| Ondansetron Hydrochloride | Onivyde (Irinotecan Hydrochloride Liposome) | Ontak (Denileukin Diftitox) | Opdivo (Nivolumab) |
| OPPA | Osimertinib | Oxaliplatin | Paclitaxel |
| Paclitaxel Albumin-stabilized Nanoparticle Formulation | PAD | Palbociclib | Palifermin |
| Palonosetron Hydrochloride | Palonosetron Hydrochloride and Netupitant | Pamidronate Disodium | Panitumumab |
| Panobinostat Lactate | Pazopanib Hydrochloride | PCV | PEB |

TABLE 5-continued

| | | | |
|---|---|---|---|
| Pegaspargase | Pegfilgrastim | Peginterferon Alfa-2b | PEG-Intron (Peginterferon Alfa-2b) |
| Pembrolizumab | Pemetrexed Disodium | Perjeta (Pertuzumab) | Pertuzumab |
| Plerixafor | Pomalidomide | Pomalyst (Pomalidomide) | Ponatinib Hydrochloride |
| Portrazza (Necitumumab) | Poteligeo (Mogamulizumab-kpkc) | Pralatrexate | Prednisone |
| Procarbazine Hydrochloride | Procrit (Epoetin Alfa) | Proleukin (Aldesleukin) | Prolia (Denosumab) |
| Promacta (Eltrombopag Olamine) | Propranolol Hydrochloride | Provenge (Sipuleucel-T) | Purinethol (Mercaptopurine) |
| Purixan (Mercaptopurine) | Radium 223 Dichloride | Raloxifene Hydrochloride | Ramucirumab |
| Rasburicase | R-CHOP | R-CVP | Recombinant Human Papillomavirus (HPV) Bivalent Vaccine |
| Recombinant Human Papillomavirus (HPV) Nonavalent Vaccine | Recombinant Human Papillomavirus (HPV) Quadrivalent Vaccine | Recombinant Interferon Alfa-2b | Regorafenib |
| Relistor (Methylnaltrexone Bromide) | R-EPOCH | Retacrit (Epoetin Alfa) | Revlimid (Lenalidomide) |
| Rheumatrex (Methotrexate) | Ribociclib | R-ICE | Rituxan (Rituximab) |
| Rituxan Hycela (Rituximab and Hyaluronidase Human) | Rituximab | Rituximab and Hyaluronidase Human | Rolapitant Hydrochloride |
| Romidepsin | Romiplostim | Rubidomycin (Daunorubicin Hydrochloride) | Rubraca (Rucaparib Camsylate) |
| Rucaparib Camsylate | Ruxolitinib Phosphate | Rydapt (Midostaurin) | Sancuso (Granisetron) |
| Sclerosol Intrapleural Aerosol (Talc) | Siltuximab | Sipuleucel-T | Somatuline Depot (Lanreotide Acetate) |
| Sonidegib | Sorafenib Tosylate | Sprycel (Dasatinib) | STANFORD V |
| Sterile Talc Powder (Talc) | Steritalc (Talc) | Stivarga (Regorafenib) | Sunitinib Malate |
| Sustol (Granisetron) | Sutent (Sunitinib Malate) | Sylatron (Peginterferon Alfa-2b) | Sylvant (Siltuximab) |
| Synribo (Omacetaxine Mepesuccinate) | Tabloid (Thioguanine) | TAC | Tafinlar (Dabrafenib) |
| Tagrisso (Osimertinib) | Talc | Talimogene Laherparepvec | Tamoxifen Citrate |
| Tarabine PFS (Cytarabine) | Tarceva (Erlotinib Hydrochloride) | Targretin (Bexarotene) | Tasigna (Nilotinib) |
| Tavalisse (Fostamatinib Disodium) | Taxol (Paclitaxel) | Taxotere (Docetaxel) | Tecentriq (Atezolizumab) |
| Temodar (Temozolomide) | Temozolomide | Temsirolimus | Thalidomide |
| Thalomid (Thalidomide) | Thioguanine | Thiotepa | Tibsovo (Ivosidenib) |
| Tisagenlecleucel | Tocilizumab | Tolak (Fluorouracil--Topical) | Topotecan Hydrochloride |
| Toremifene | Torisel (Temsirolimus) | Totect (Dexrazoxane Hydrochloride) | TPF |
| Trabectedin | Trametinib | Trastuzumab | Treanda (Bendamustine Hydrochloride) |
| Trexall (Methotrexate) | Trifluridine and Tipiracil Hydrochloride | Trisenox (Arsenic Trioxide) | Tykerb (Lapatinib Ditosylate) |
| Unituxin (Dinutuximab) | Uridine Triacetate | VAC | Valrubicin |
| Valstar (Valrubicin) | Vandetanib | VAMP | Varubi (Rolapitant Hydrochloride) |

TABLE 5-continued

| | | | |
|---|---|---|---|
| Vectibix (Panitumumab) | VeIP | Velcade (Bortezomib) | Vemurafenib |
| Venclexta (Venetoclax) | Venetoclax | Verzenio (Abemaciclib) | Vidaza (Azacitidine) |
| Vinblastine Sulfate | Vincristine Sulfate | Vincristine Sulfate Liposome | Vinorelbine Tartrate |
| VIP | Vismodegib | Vistogard (Uridine Triacetate) | Vitrakvi (Larotrectinib Sulfate) |
| Vizimpro (Dacomitinib) | Voraxaze (Glucarpidase) | Vorinostat | Votrient (Pazopanib Hydrochloride) |
| Vyxeos (Daunorubicin Hydrochloride and Cyarabine Liposome) | Xalkori (Crizotinib) | Xeloda (Capecitabine) | XELIRI |
| XELOX | Xgeva (Denosumab) | Xofigo (Radium 223 Dichloride) | Xtandi (Enzalutamide) |
| Yervoy (Ipilimumab) | Yescarta (Axicabtagene Ciloleucel) | Yondelis (Trabectedin) | Zaltrap (Ziv-Aflibercept) |
| Zarxio (Filgrastim) | Zejula (Niraparib Tosylate Monohydrate) | Zelboraf (Vemurafenib) | Zevalin (Ibritumomab Tiuxetan) |
| Zinecard (Dexrazoxane Hydrochloride) | Ziv-Aflibercept | Zofran (Ondansetron Hydrochloride) | Zoladex (Goserelin Acetate) |
| Zoledronic Acid | Zolinza (Vorinostat) | Zometa (Zoledronic Acid) | Zydelig (Idelalisib) |
| Zykadia (Ceritinib) | Zytiga (Abiraterone Acetate) | | |

For a more detailed description of anticancer agents and other optional therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

In another embodiment, the methods of treating cancer provided herein comprise administering a Pharmaceutical Composition of the Disclosure to a subject in combination with radiation therapy and, optionally, an immune checkpoint inhibitor. The methods provided herein are not limited by the types, amounts, or delivery and administration systems used to deliver the therapeutic dose of radiation to a patient. For example, the patient may receive photon radiotherapy, particle beam radiation therapy, other types of radiotherapies, and combinations thereof. In some embodiments, the radiation is delivered to the patient using a linear accelerator. In still other embodiments, the radiation is delivered using a gamma knife.

The source of radiation can be external or internal to the patient. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by patients. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The patient may optionally receive radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to a patient, so long as the dose of radiation is tolerated by the patient without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581 incorporated herein by reference in its entirety). The effects of radiation can be at least partially controlled by the clinician. In one embodiment, the dose of radiation is fractionated for maximal target cell exposure and reduced toxicity.

In one embodiment, the total dose of radiation administered to a patient is about 0.01 Gray (Gy) to about 100 Gy.

In another embodiment, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), or 1-2 Gy (e.g., 1.5-2 Gy). The daily dose of radiation should be sufficient to induce destruction of the targeted cells. If stretched over a period, in one embodiment, radiation is not administered every day, thereby allowing the animal to rest and the effects of the therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects. Radiation therapy can be initiated at any time in the therapeutic period. In one embodiment, radiation is initiated in week 1 or week 2, and is administered for the remaining duration of the therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the methods provided herein.

V. Methods of Making Lyophilates of the Disclosure

In another embodiment, the disclosure provides a method of making a Lyophilate of the Disclosure, the method comprising:

(i) preparing a pre-lyophilization solution comprising Compound 1, a bulking agent, and water;

(ii) cooling the pre-lyophilization solution until it is frozen; and (iii) applying a vacuum to the frozen pre-lyophilization solution to give the lyophilate.

In another embodiment, the bulking agent is mannitol.

In another embodiment, the pre-lyophilization solution further comprises ethanol. In another embodiment, the pre-lyophilization solution further comprises t-butanol.

In another embodiment, the disclosure provides a method of making a Lyophilate of the Disclosure, the method comprising:

(i) dissolving Compound 1 and a bulking agent, e.g., mannitol, in a mixture of t-butanol, ethanol, and water at a temperature of about 20° C. to about 50° C. to give a pre-lyophilization solution;

(ii) cooling the pre-lyophilization solution until it is frozen or partially frozen; and (iii) applying a vacuum to the frozen or partially frozen pre-lyophilization solution to give the lyophilate.

In another embodiment, Compound 1 is dissolved in a mixture of t-butanol, ethanol, and water at a temperature of about 25° C. to about 35° C. In another embodiment, the temperature is about 25° C. to about 30° C. In another embodiment, the temperature is about 25° C. In another embodiment, the temperature is about 30° C.

In another embodiment, the pre-lyophilization solution further comprises sodium carboxymethyl cellulose. In another embodiment, the pre-lyophilization solution further comprises poloxamer 188. In another embodiment, the pre-lyophilization solution further comprises soy lecithin. In another embodiment, the pre-lyophilization solution further comprises L-histidine. In another embodiment, the pre-lyophilization solution further comprises ethanol, t-butanol, sodium carboxymethyl cellulose, poloxamer 188, soy lecithin, and L-histidine.

In another embodiment, the concentration of Compound 1 in the pre-lyophilization solution is about 1 mg/mL to about 15 mg/mL. In another embodiment, the concentration of Compound 1 in the pre-lyophilization solution is about 10 mg/mL.

VI. Methods of Making Pharmaceutical Compositions

In another embodiment, the disclosure provides a method of making a Pharmaceutical Composition of the Disclosure, the method comprising suspending a Lyophilate of the Disclosure in a solvent. In another embodiment, the solvent comprises water.

VII. Kits

In another embodiment, the disclosure provides a kit comprising a Lyophilate of the Disclosure packaged as single unit dose in a vial. In another embodiment, the vial has a stopper and a cap. In another embodiment, the vial is glass.

In another embodiment, the disclosure provides a kit comprising a Lyophilate of the Disclosure packaged as single unit dose in a vial for the treatment of cancer in a subject.

In another embodiment, the kit further comprises instructions for suspending the lyophilate in a solvent to give a Pharmaceutical Composition of the Disclosure.

In another embodiment, the kit further comprises instructions for administering the Pharmaceutical Composition of the Disclosure to a subject.

In another embodiment, the kit further comprises an optional therapeutic agent.

In another embodiment, the kit further comprises a device suitable for administering the Pharmaceutical Composition of the Disclosure to a subject subcutaneously.

VIII. Definitions

The terms "(S)-isopropyl 2-((S)-2-acetamido-3-(1H-indol-3-yl)propanamido)-6-diazo-5-oxohexanoate" and "Compound 1" refer to a prodrug of 6-diazo-5-oxo-L-norleucine (DON) having the following structure:

Compound 1 is described in U.S. Pat. No. 10,336,778 B2.

The term "lyophilate" as used herein refers to a powder obtained by lyophilization.

The terms "lyophilization," "lyophilizing," and "lyophilized" as used herein refer to a freeze-drying process by which Compound 1 is frozen and, while still in the frozen state, water and other solvents, if present, are removed by sublimation under vacuum. Compound 1 may be lyophilized in the presence of other agents, e.g., bulking agents, cellulose-based suspension modulators, poloxamer-based suspension modulators, lecithin-based suspension modulators, buffering agents, in order to enhance the properties of the lyophilate thus obtained and/or the properties of any pharmaceutical composition comprising the lyophilate.

The term "solvent" as used herein refers to a liquid e.g., water, or mixture of liquids, e.g., water and ethanol, that is suitable for administration to a subject as part of a pharmaceutical composition or formulation. In one embodiment, the solvent comprises a combination of water and one, two, three, or four additional pharmaceutically acceptable water miscible solvents, e.g., dioxolanes, dimethylacetamide, butylene glycol, polyethylene glycol, glycerin, ethanol, and the like, or a combination thereof. In another embodiment, the solvent is water. In another embodiment, the solvent is a combination of water and one additional pharmaceutically acceptable water miscible solvent. In another embodiment, the solvent is a combination of water and ethanol. In another embodiment, the solvent comprises a combination of water and one, two, three, or four additional pharmaceutically acceptable water immiscible solvents, e.g., peanut oil, ethyl oleate, and the like. In another embodiment, the solvent comprises about 10% to about 30% of water and about 70% to about 90% of a water miscible solvent, e.g., ethanol. In another embodiment, the solvent comprises about 15% to about 25% of water and about 75% to about 85% of a water miscible solvent. In another embodiment, the solvent consists essentially of about 20% of water and about 80% of a water miscible solvent.

The term "bulking agent" as used herein refers to a pharmaceutically acceptable excipient that provides structure to the lyophilized cake to prevent shrinkage and collapse. Exemplary non-limiting bulking agents include mannitol, lactose, sucrose, polyethylene glycol, and glycine.

The term "cellulose-based suspension modulator" as used herein refers to a polysaccharide consisting of a linear chain of β(1→4) linked D-glucose units. Exemplary non-limiting cellulose-based suspension modulators include hydroxypropylcellulose, hydroxymethylcellulose, and sodium carboxymethyl cellulose.

The term "poloxamer-based suspension modulator" as used herein refers to nonionic triblock copolymer comprising a central hydrophobic chain of polyoxypropylene flanked by two hydrophilic chains of polyoxyethylene. Exemplary non-limiting poloxamer-based suspension modulators include poloxamer 188, NF (Pluronic© F-68) and poloxamer 407 (Pluronic© F-127).

The term "lecithin-based suspension modulator" as used herein refers to a mixture comprising glycerophospholipids, e.g., phosphatidyl choline, phosphatidyl ethanolamine, phosphatidyl inositol, phosphatidyl serine, and phosphatidic acid. An exemplary non-limiting lecithin-based suspension modulator is soy lecithin.

The term "buffering agent" as used herein refers to a pharmaceutically acceptable excipient that helps maintain the pH during lyophilization and after reconstitution of the resulting lyophilate. Exemplary non-limiting buffering agents include glycine, L-histidine, phosphate, acetic acid, lactic acid, citric acid, and Tris.

The term "diluent" as used herein refers to a liquid used to dilute a pharmaceutical composition before parenteral administration to a subject. In one embodiment, the diluent is normal saline, 5% dextrose, lactated Ringer's solution, or any other sterile fluid designed to be compatible with administration, e.g., by intravenous infusion, to humans. In another embodiment, the diluent is normal saline.

The term "weight ratio" as used herein refers to mass of Compound 1 divided by the mass of another agent, e.g., a bulking agent or a buffering agent, in the lyophilate. For example, the Compound 1/bulking agent weight ratio in a lyophilate comprising 67.5 mg of Compound 1 and 135 mg of mannitol is 0.5. The Compound 1/buffering agent weight ratio in a lyophilate comprising 67.5 mg of Compound 1, 135 mg of mannitol, and 3.88 mg of L-histidine is 17.4.

The term "% wt/wt" as used herein refers to the mass of one lyophilate ingredient divided by the combined mass of all lyophilate ingredients, times 100. For example, the % wt/wt of Compound 1 in a lyophilate comprising 62.5 mg of Compound 1, 125 mg of mannitol, 8.33 mg of sodium carboxymethyl cellulose (NaCMC), 7.08 mg of Poloxamer 188, NF, 4.31 mg of histidine, and 41.7 mg of soy lecithin is 25.1% (62.5 mg/248.92 mg=0.251×100=25.1% wt/wt).

The term "average particle size distribution" or "$D_{50}$" as used herein is the diameter where 50 mass-% of the particles have a larger equivalent diameter, and the other 50 mass-% have a smaller equivalent diameter as determined by laser diffraction.

The terms "intermittent dose administration," "intermittent dosing schedule," and similar terms as used herein refer to non-continuous administration of a Pharmaceutical Composition of the Disclosure to a subject. Intermittent dose administration regimens useful in the present disclosure encompass any discontinuous administration regimen that provides a therapeutically effective amount of a Pharmaceutical Composition of the Disclosure to a subject in need thereof. Intermittent dosing regimens can use equivalent, lower, or higher doses of a Pharmaceutical Composition of the Disclosure than would be used in continuous dosing regimens. Advantages of intermittent dose administration include, but are not limited to, improved safety, decreased toxicity, e.g., decreased weight loss, increased exposure, increased efficacy, and/or increased subject compliance. These advantages may be realized when a Pharmaceutical Composition of the Disclosure is administered as a single agent or when administered in combination with one or more additional therapeutic agents, e.g., an immune checkpoint inhibitor.

In one embodiment, a Pharmaceutical Composition of the Disclosure is administered to the subject according to an intermittent dosing schedule to treat cancer. In another embodiment, the intermittent dosing schedule increases the therapeutic index of the Pharmaceutical Composition of the Disclosure. The therapeutic index is a comparison of the amount of the Pharmaceutical Composition of the Disclosure that causes the therapeutic effect, e.g., decrease in tumor mass, increase in time to tumor progression, and/or increase in subject survival time, to the amount that causes toxicity, e.g. body weight loss.

In one embodiment, the Pharmaceutical Composition of the Disclosure is administered to the subject every other day.

In another embodiment, the Pharmaceutical Composition of the Disclosure is administered to the subject once a week.

In another embodiment, the Pharmaceutical Composition of the Disclosure is administered to the subject twice a week on consecutive days, e.g., on Monday and Tuesday.

In another embodiment, the Pharmaceutical Composition of the Disclosure is administered to the subject twice a week on non-consecutive days, e.g., on Monday and Wednesday, on Monday and Thursday, or on Tuesday and Friday.

In another embodiment, the Pharmaceutical Composition of the Disclosure is administered to the subject twice a week on Monday and Thursday.

In another embodiment, the Pharmaceutical Composition of the Disclosure is administered to the subject twice a week on Tuesday and Friday.

In another embodiment, the Pharmaceutical Composition of the Disclosure is administered to the subject three times a week on consecutive days, e.g., on Monday, Tuesday, and Wednesday.

In another embodiment, the Pharmaceutical Composition of the Disclosure is administered to the subject three times a week on non-consecutive days, e.g., on Monday, Wednesday, and Friday.

In another embodiment, the Pharmaceutical Composition of the Disclosure is administered to the subject four times a week on consecutive days, e.g., on Monday, Tuesday, Wednesday and Thursday.

In another embodiment, the Pharmaceutical Composition of the Disclosure is administered to the subject four times a week on nonconsecutive days, e.g., on Monday, Tuesday, Thursday, and Friday.

In another embodiment, the Pharmaceutical Composition of the Disclosure is administered to the subject five times a week on consecutive days, e.g., on Monday, Tuesday, Wednesday, Thursday and Friday.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to an individual in a sequence and sufficiently close in time so as to provide the desired therapeutic effect and can act in concert. For example, a Pharmaceutical Composition of the Disclosure can be administered to a subject at the same time or sequentially in any order at different points in time as the optional therapeutic agent. A Pharmaceutical Composition of the Disclosure and an optional therapeutic agent can be administered separately, in any appropriate form and by any suitable route. When a Pharmaceutical Composition of the Disclosure and an optional therapeutic agent are not administered concurrently, it is understood that they can be administered in any order to a subject in need thereof. For example, a Pharmaceutical Composition of the Disclosure can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, or more before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, or more after) an optional therapeutic agent.

The terms "a" and "an" refer to one or more than one.

The term "about," as used herein, includes the recited number ±10%. Thus, "about 10" means 9 to 11.

As used herein, the terms "treat," "treating," "treatment," "therapeutic methods," and the like refer to eliminating, reducing, or ameliorating a disease or condition, and/or symptoms associated therewith. Although not precluded, treating a disease or condition does not require that the disease, condition, or symptoms associated therewith be completely eliminated. However, in one embodiment, administration of Compound 1 and, optionally, one or more optional therapeutic agents leads to remission of the cancer.

The term "therapeutically effective amount," as used herein, refers to that amount of the therapeutic agent sufficient to result in amelioration of one or more symptoms of a disorder, or prevent advancement of a disorder, or cause regression of the disorder. For example, with respect to the treatment of cancer, in one embodiment, a therapeutically effective amount will refer to the amount of a therapeutic agent that causes a therapeutic response, e.g., normalization of blood counts, decrease in the rate of tumor growth, decrease in tumor mass, decrease in the number of metastases, increase in time to tumor progression, and/or increase subject survival time by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%, or more.

The term "pharmaceutically acceptable carrier" or "pharmaceutically acceptable vehicle" encompasses any of the standard pharmaceutical carriers, solvents, surfactants, or vehicles. Suitable pharmaceutically acceptable vehicles include aqueous vehicles and nonaqueous vehicles. Standard pharmaceutical carriers and their formulations are described in Remington's Pharmaceutical Sciences, Mack Publishing Co., Easton, PA, 19th ed. 1995.

The term "container" means any receptacle and closure therefore suitable for storing, shipping, dispensing, and/or handling a pharmaceutical product. In one embodiment, the container is a vial.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

In some embodiments, when administered in combination, two or more agents can have a synergistic effect. The terms "synergy," "synergistic," "synergistically" and derivations thereof, such as in a "synergistic effect" or a "synergistic combination" or a "synergistic composition" as used herein refer to circumstances under which the biological activity of a combination of an agent and at least one additional therapeutic agent is greater than the sum of the biological activities of the respective agents when administered individually. For example, the term "synergistically effective" as used herein refers to the interaction between Compound 1 and one or more immune checkpoint inhibitors that causes the total effect of the drugs to be greater than the sum of the individual effects of each drug. See, e.g, Berenbaum, *Pharmacological Reviews* 41:93-141 (1989).

IX. Particular Embodiments

In another aspect, the disclosure provides the following particular embodiments.

Embodiment 1. A lyophilate comprising Compound 1 and a bulking agent.

Embodiment 2. The lyophilate of Embodiment 1 comprising about 67.5 mg of Compound 1.

Embodiment 3. The lyophilate of Embodiments 1 or 2, wherein the Compound 1/bulking agent weight ratio is about 5 to about 0.05.

Embodiment 4. The lyophilate of Embodiment 3, wherein the Compound 1/bulking agent weight ratio is about 1 to about 0.2.

Embodiment 5. The lyophilate of Embodiment 5, wherein the Compound 1/bulking agent weight ratio is about 0.5

Embodiment 6. The lyophilate of any one of Embodiments 1-5, wherein the bulking agent is mannitol.

Embodiment 7. The lyophilate of Embodiment 6 comprising about 135 mg of mannitol.

Embodiment 8. The lyophilate of any one of Embodiments 1-7 further comprising a cellulose-based suspension modulator.

Embodiment 9. The lyophilate of Embodiment 8, wherein the Compound 1/cellulose-based suspension modulator ratio is about 25 to about 0.3.

Embodiment 10. The lyophilate of Embodiment 9, wherein the Compound 1/cellulose-based suspension modulator weight ratio is about 5 to about 2.

Embodiment 11. The lyophilate of Embodiment 10, wherein the Compound 1/cellulose-based suspension modulator weight ratio is about 2.7 or about 7.5.

Embodiment 12. The method of any one of Embodiments 8-11, wherein the cellulose-based suspension modulator is sodium carboxymethyl cellulose.

Embodiment 13. The lyophilate of Embodiment 12 comprising about 25.2 mg or about 9.0 mg of sodium carboxymethyl cellulose.

Embodiment 14. The lyophilate of any one of Embodiments 1-13 further comprising a poloxamer-based suspension modulator.

Embodiment 15. The lyophilate of Embodiment 14, wherein the Compound 1/poloxamer-based suspension modulator ratio is about 80 to about 1.

Embodiment 16. The lyophilate of Embodiment 15, wherein the Compound 1/poloxamer-based suspension modulator weight ratio is about 10 to about 6.

Embodiment 17. The lyophilate of Embodiment 16, wherein the Compound 1/poloxamer-based suspension modulator weight ratio is about 8.8.

Embodiment 18. The lyophilate of any one of Embodiments 14-17, wherein the poloxamer-based suspension modulator is Poloxamer 188.

Embodiment 19. The lyophilate of Embodiment 18 comprising about 7.65 mg of Poloxamer 188.

Embodiment 20. The lyophilate of any one of Embodiments 1-19 further comprising a lecithin-based suspension modulator.

Embodiment 21. The lyophilate of Embodiment 20, wherein the Compound 1/lecithin-based suspension modulator ratio is about 20 to about 0.1.

Embodiment 22. The lyophilate of Embodiment 21, wherein the Compound 1/lecithin-based suspension modulator weight ratio is about 10 to about 0.5.

Embodiment 23. The lyophilate of Embodiment 22, wherein the Compound 1/lecithin-based suspension modulator weight ratio is about 1.5.

Embodiment 24. The lyophilate of any one of Embodiments 20-23, wherein the lecithin-based suspension modulator is soy lecithin.

Embodiment 25. The lyophilate of Embodiment 24 comprising about 45 mg of soy lecithin.

Embodiment 26. The lyophilate of any one of Embodiments 1-25 further comprising a buffering agent.

Embodiment 27. The lyophilate of Embodiment 26, wherein the Compound 1/buffering agent weight ratio is about 50 to about 1.

Embodiment 28. The lyophilate of Embodiment 27, wherein the Compound 1/buffering agent weight ratio is about 20 to about 10.

Embodiment 29. The lyophilate of Embodiment 28, wherein the Compound 1/buffering agent weight ratio is about 17.4.

Embodiment 30. The lyophilate of any one of Embodiments 26-29, wherein buffering agent is L-histidine.

Embodiment 31. The lyophilate of Embodiment 30 comprising about 3.88 mg of L-histidine.

Embodiment 32. A pharmaceutical composition comprising the lyophilate of any one of Embodiments 1-31, wherein the lyophilate is suspended in a solvent.

Embodiment 33. The pharmaceutical composition of Embodiment 32, wherein the solvent comprises water.

Embodiment 34. The pharmaceutical composition of Embodiments 32 or 33, wherein the Compound 1 concentration is about 25 mg/mL to about 30 mg/mL.

Embodiment 35. The pharmaceutical composition of any one of Embodiments 32-34, wherein the average particle size distribution of Compound 1 in the suspension is about 1 μm to about 30 μm after 3 days at 2-8° C.

Embodiment 36. A method for treating cancer in a subject in need thereof, the method comprising administering a therapeutically effective amount of the pharmaceutical composition of any one of Embodiments 32-35 to the subject.

Embodiment 37. The method of Embodiment 36, wherein the pharmaceutical composition is administered subcutaneous to the subject.

Embodiment 38. The method of Embodiments 36 or 37 further comprising administering an optional therapeutic agent to the subject.

Embodiment 39. A method of making the lyophilate of Embodiment 1, the method comprising:

(i) preparing a pre-lyophilization solution comprising Compound 1, a bulking agent, and water;

(ii) cooling the pre-lyophilization solution until it is frozen or partially frozen; and (iii) applying a vacuum to the frozen or partially frozen pre-lyophilization solution to give the lyophilate.

Embodiment 40. The method of Embodiment 39, wherein the bulking agent is mannitol.

Embodiment 41. The method of Embodiments 39 or 40, wherein the pre-lyophilization solution further comprises ethanol.

Embodiment 42. The method of any one of Embodiments 39-41, wherein the pre-lyophilization solution further comprises t-butanol.

Embodiment 43. The method of any one of Embodiments 39-42, wherein the pre-lyophilization solution further comprises sodium carboxymethyl cellulose.

Embodiment 44. The method of any one of Embodiments 39-43, wherein the pre-lyophilization solution further comprises poloxamer 188.

Embodiment 45. The method of any one of Embodiments 39-44, wherein the pre-lyophilization solution further comprises soy lecithin.

Embodiment 46. The method of any one of Embodiments 39-45, wherein the pre-lyophilization solution further comprises L-histidine.

Embodiment 47. A method of making the pharmaceutical composition of Embodiment 32, the method comprising suspending the lyophilate in a solvent.

Embodiment 48. The method of Embodiment 47, wherein the solvent comprises water.

Embodiment 49. A kit comprising the lyophilate of any one of Embodiments 1-31 packaged as single unit dose in a vial.

Embodiment 50. The kit of Embodiment 49 for the treatment of cancer in a subject in need thereof.

Embodiment 51. The kit of Embodiments 49 or 50 further comprising instructions for suspending the lyophilate in a solvent to give a pharmaceutical composition.

Embodiment 52. The kit of Embodiments 49-51 further comprising instructions for administering the pharmaceutical composition to the subject.

In another aspect, the disclosure provides the following particular embodiments.

Embodiment A1. A lyophilate comprising about 20% wt/wt to about 45% wt/wt of Compound 1 and about 35% wt/wt to about 55% wt/wt of a bulking agent.

Embodiment A2. The lyophilate of Embodiment A1 further comprising about 1% wt/wt to about 10% wt/wt of a cellulose-based suspension modulator.

Embodiment A3. The lyophilate of Embodiments A1 or A2 further comprising about 1% wt/wt to about 5% wt/wt of a poloxamer-based suspension modulator.

Embodiment A4. The lyophilate of any one of Embodiments A1-A3 further comprising about 10% wt/wt to about 20% wt/wt of a lecithin-based suspension modulator.

Embodiment A5. The lyophilate of any one of Embodiments A1-A5 further comprising about 0.5% wt/wt to about 2.5% wt/wt of a buffer.

Embodiment A6. The lyophilate of any one of Embodiments A1-A5 comprising:

(i) about 20% wt/wt to about 30% wt/wt of Compound 1;

(ii) about 45% wt/wt to about 55% wt/wt of a bulking agent;

(iii) about 1% wt/wt to about 9% wt/wt of a cellulose-based suspension modulator;

(iv) about 1% wt/wt to about 4% wt/wt of a poloxamer-based suspension modulator;

(v) about 12% wt/wt to about 20% wt/wt of a lecithin-based suspension modulator; and (vi) about 1% wt/wt to about 2% wt/wt of a buffer.

Embodiment A7. The lyophilate of any one of Embodiments A1-A6 comprising about 25.1% wt/wt of Compound 1.

Embodiment A8. The lyophilate of any one of Embodiments A1-A7 comprising about 50.2% wt/wt of the bulking agent.

Embodiment A9. The lyophilate of any one of Embodiments A1-A8 comprising about 3.3% wt/wt of a cellulose-based suspension modulator.

Embodiment A10. The lyophilate of any one of Embodiments A1-A9 comprising about 2.8% wt/wt poloxamer-based suspension modulator.

Embodiment A11. The lyophilate of any one of Embodiments A1-A10 comprising about 16.8% wt/wt of a lecithin-based suspension modulator.

Embodiment A12. The lyophilate of any one of Embodiments A1-A11 comprising about 1.7% wt/wt of a buffer.

Embodiment A13. The lyophilate of any one of Embodiments A1-A12, wherein the bulking agent is mannitol.

Embodiment A14. The lyophilate of any one of Embodiments A1-A13, wherein the cellulose-based suspension modulator is sodium carboxymethyl cellulose.

Embodiment A15. The lyophilate of any one of Embodiments A1-A14, wherein the poloxamer-based suspension modulator is Poloxamer 188 (copolymer of ethylene oxide and propylene oxide).

Embodiment A16. The lyophilate of any one of Embodiments A1-A15, wherein the lecithin-based suspension modulator is soy lecithin.

Embodiment A17. The lyophilate of any one of Embodiments A1-A16, wherein the buffer is histidine.

Embodiment A18. The lyophilate of Embodiment A1 comprising:

(i) about 62.5 mg of Compound 1;

(ii) about 125 mg of mannitol;

(iii) about 8.3 mg of sodium carboxymethyl cellulose;

(iv) about 7.1 mg of Poloxamer 188, NF;

(v) about 41.7 mg of soy lecithin; and (vi) about 4.3 mg of histidine.

Embodiment A19. A pharmaceutical composition comprising the lyophilate of any one of Embodiments A1-A18, wherein the lyophilate is suspended in a pharmaceutically acceptable carrier.

Embodiment A20. The pharmaceutical composition of Embodiment A19, wherein the pharmaceutically acceptable carrier comprises water.

Embodiment A21. The pharmaceutical composition of Embodiments A19 or A20, wherein the Compound 1 concentration is about 20 mg/mL to about 60 mg/mL.

Embodiment A22. The pharmaceutical composition of Embodiment A21, wherein the Compound 1 concentration is about 25 mg/mL.

Embodiment A23. The pharmaceutical composition of any one of Embodiments A19-22, wherein the average particle size distribution of Compound 1 in the suspension is about 1 μm to about 30 μm.

Embodiment A24. A method for treating cancer in a subject in need thereof, the method comprising administering a therapeutically effective amount of the pharmaceutical composition of any one of Embodiments A19-A23 to the subject.

Embodiment A25. The method of Embodiment A24, wherein the cancer is a solid tumor.

Embodiment A26. The method of Embodiment A24, wherein the cancer is a hematological cancer.

Embodiment A27. The method of Embodiment A24, wherein the cancer is one or more of cancers listed in Table 1.

Embodiment A28. The method of Embodiment A24, wherein the cancer is of hepatocellular carcinoma, glioblastoma, lung cancer, breast cancer, head and neck cancer, prostate cancer, melanoma, or colorectal cancer.

Embodiment A29. The method of Embodiment A24, wherein the cancer is colorectal cancer, breast cancer, lymphoma, melanoma, kidney cancer, or lung cancer.

Embodiment A30. The method of Embodiment A24, wherein the cancer is an advanced solid tumor, non-small cell lung cancer, or squamous cell carcinoma of head and neck.

Embodiment A31. The method of any one of Embodiments A24-30, wherein the pharmaceutical composition is administered subcutaneously to the subject.

Embodiment A32. The method of Embodiment A31, wherein the pharmaceutical composition is administered to the subject according to an intermittent dosing schedule.

Embodiment A33. The method of Embodiment A32, wherein the wherein the pharmaceutical composition is administered to the subject twice a week on non-consecutive days.

Embodiment A34. The method of any one of Embodiments A24-3A3 further comprising administering one or more optional therapeutic agents to the subject.

Embodiment A35. The method of Embodiment A34, wherein the one or more optional therapeutic agents comprise one or more immune checkpoint inhibitors.

Embodiment A36. The method of Embodiment A35, wherein the one or more immune checkpoint inhibitors comprise a PD-1 inhibitor, a PD-L1 inhibitor, a CTLA-4 inhibitor, a LAG3 inhibitor, a TIM3 inhibitor, or a TIGIT inhibitor, or a combination thereof.

Embodiment A37. The method of Embodiment A36, wherein the one or more immune checkpoint inhibitors comprise an anti-PD-1 antibody.

Embodiment A38. The method of Embodiment A37, wherein the anti-PD-1 antibody is nivolumab, pembrolizumab, pidilizumab, STI-A1110, (spartalizumab), JTX-4014, sintilimab, MEDI 0680, AGEN2034, BGB-A317, AB122, dostarlimab, PF-06801591, cemiplimab, tislelizumab, toripalimab, camrelizumab, SYM021, JNJ 63723283, HLX10, LZM009, or MGA012.

Embodiment A39. The method of any one of Embodiments A35-A38, wherein the one or more immune checkpoint inhibitors comprise an anti-PD-L1 antibody.

Embodiment A40. The method of Embodiment A39, wherein the anti-PD-L1 antibody is avelumab, atezolizumab, durvalumab, KN035, or STI-A1014.

Embodiment A41. The method of any one of Embodiments A35-A40, wherein the one or more immune checkpoint inhibitors comprise an anti-CTLA-4 antibody.

Embodiment A42. The method of Embodiment A41, wherein the anti-CTLA-4 antibody is ipilimumab or tremelimumab.

Embodiment A43. The method of any one of Embodiments A35-A42, wherein the one or more immune checkpoint inhibitors comprise an anti-LAG3 antibody.

Embodiment A44. The method of Embodiment A43, wherein the anti-LAG3 antibody is GSK2831781.

Embodiment A45. The method of any one of Embodiments A35-A44, wherein the one or more immune checkpoint inhibitors comprise an anti-TIM3 antibody.

Embodiment A46. The method of any one of Embodiments A35-A45, wherein the one or more immune checkpoint inhibitors comprise an anti-TIGIT antibody.

Embodiment A47. The method of Embodiment A46, wherein the anti-TIGIT antibody is vibostolimab (MK-7684), tiragolumab (RG6058), EOS-448, BMS-986207, BGB-A1217, MTIG7192A, AB154, ASP8374, or MK-7684.

Embodiment A48. The method of any one of Embodiments A35-A47, wherein the cancer is or has become resistant to treatment with at least one immune checkpoint inhibitor.

Embodiment A49. A kit comprising the lyophilate of any one of Embodiments A1-A18 packaged as single unit dose in a container.

Embodiment A50. The kit of Embodiment A49 further comprising instructions for suspending the lyophilate in a solvent to give a pharmaceutical composition.

Embodiment A51 The kit of Embodiments A49 or A50 further comprising a label with instructions on how to use the kit according to the methods of any one of Embodiments A24-48.

Embodiment A52. The kit of Embodiment A51 wherein the label is approved by the United States Food and Drug Administration (FDA), the European Medicines Agency (EMA), the China Food and Drug Administration (CFDA) or the Japanese Ministry of Health Labor and Welfare (MHLW)

Embodiment A53. A method of making the lyophilate of Embodiment A1, the method comprising:

(i) preparing a pre-lyophilization solution comprising Compound 1, a bulking agent, and water;
(ii) cooling the pre-lyophilization solution until it is frozen or partially frozen; and
(iii) applying a vacuum to the frozen or partially frozen pre-lyophilization solution to give the lyophilate.

Embodiment A54. The method of Embodiment A54, wherein the bulking agent is mannitol.

Embodiment A55. The method of Embodiments A53 or A54, wherein the pre-lyophilization solution further comprises ethanol.

Embodiment A56. The method of any one of Embodiments A53-A55, wherein the pre-lyophilization solution further comprises t-butanol.

Embodiment A57. The method of any one of Embodiments A53-A56, wherein the pre-lyophilization solution further comprises sodium carboxymethyl cellulose.

Embodiment A58. The method of any one of Embodiments A53-A57, wherein the pre-lyophilization solution further comprises poloxamer 188.

Embodiment A59. The method of any one of Embodiments A53-A58, wherein the pre-lyophilization solution further comprises soy lecithin.

Embodiment A60. The method of any one of Embodiments A53-A59, wherein the pre-lyophilization solution further comprises L-histidine.

Embodiment A61. A method of making the pharmaceutical composition of Embodiment A19, the method comprising suspending the lyophilate in a solvent.

Embodiment A62. The method of Embodiment A61, wherein the solvent comprises water.

Embodiment A63. A kit for carrying out the methods of any one of Embodiments A24-A48, the kit comprising a single unit dose of the lyophilate of any one of Embodiments A1-18 packaged in a container.

Embodiment A64. The kit of Embodiment A63 further comprising instructions for suspending the lyophilate in a solvent to give a pharmaceutical composition.

Embodiment A65. The kit of Embodiments A63 or A64 further comprising a label that is approved by the United States Food and Drug Administration (FDA), the European Medicines Agency (EMA), the China Food and Drug Administration (CFDA) or the Japanese Ministry of Health Labor and Welfare (MHLW).

Embodiment A66. The pharmaceutical composition of any one of Embodiments A19-A23 for use in treating cancer in a subject in need thereof.

Embodiment A67. The pharmaceutical composition for use of Embodiment A66, wherein the cancer is a solid tumor.

Embodiment A68. The pharmaceutical composition for use of Embodiment A66, wherein the cancer is a hematological cancer.

Embodiment A69. The pharmaceutical composition for use of Embodiment A66, wherein the cancer is one or more of cancers listed in Table 1.

Embodiment A70. The pharmaceutical composition for use of Embodiment A66, wherein the cancer is of hepatocellular carcinoma, glioblastoma, lung cancer, breast cancer, head and neck cancer, prostate cancer, melanoma, or colorectal cancer.

Embodiment A71. The pharmaceutical composition for use of Embodiment A66, wherein the cancer is colorectal cancer, breast cancer, lymphoma, melanoma, kidney cancer, or lung cancer.

Embodiment A72. The pharmaceutical composition for use of Embodiment A66, wherein the cancer is an advanced solid tumor, non-small cell lung cancer, or squamous cell carcinoma of head and neck.

Embodiment A73. The pharmaceutical composition for use of any one of Embodiments A66-A72, wherein the pharmaceutical composition is to be administered subcutaneously to the subject.

Embodiment A74. The pharmaceutical composition for use of Embodiment A73, wherein the pharmaceutical composition is to be administered to the subject according to an intermittent dosing schedule.

Embodiment A75. The pharmaceutical composition for use of Embodiment A74, wherein the wherein the pharmaceutical composition is to be administered to the subject twice a week on non-consecutive days.

Embodiment A76. The pharmaceutical composition for use of any one of Embodiments A66-A75, wherein the pharmaceutical composition is to be administered with one or more optional therapeutic agents to the subject.

Embodiment A77. The pharmaceutical composition for use of Embodiment A76, wherein the one or more optional therapeutic agents comprise one or more immune checkpoint inhibitors.

Embodiment A78. The pharmaceutical composition for use of Embodiment A77, wherein the one or more immune checkpoint inhibitors comprise a PD-1 inhibitor, a PD-L1 inhibitor, a CTLA-4 inhibitor, a LAG3 inhibitor, a TIM3 inhibitor, or a TIGIT inhibitor, or a combination thereof.

Embodiment A79. The pharmaceutical composition for use of Embodiment A78, wherein the one or more immune checkpoint inhibitors comprise an anti-PD-1 antibody.

Embodiment A80. The pharmaceutical composition for use of Embodiment A79, wherein the anti-PD-1 antibody is nivolumab, pembrolizumab, pidilizumab, STI-A1110, (spartalizumab), JTX-4014, sintilimab, MEDI 0680, AGEN2034, BGB-A317, AB122, dostarlimab, PF-06801591, cemiplimab, tislelizumab, toripalimab, camrelizumab, SYM021, JNJ 63723283, HLX10, LZM009, or MGA012.

Embodiment A81. The pharmaceutical composition for use of any one of Embodiments A77-A80, wherein the one or more immune checkpoint inhibitors comprise an anti-PD-L1 antibody.

Embodiment A82. The pharmaceutical composition for use of Embodiment A81, wherein the anti-PD-L1 antibody is avelumab, atezolizumab, durvalumab, KN035, or STI-A1014.

Embodiment A83. The pharmaceutical composition for use of any one of Embodiments A77-A82, wherein the one or more immune checkpoint inhibitors comprise an anti-CTLA-4 antibody.

Embodiment A84. The pharmaceutical composition for use of Embodiment A83, wherein the anti-CTLA-4 antibody is ipilimumab or tremelimumab.

Embodiment A85. The pharmaceutical composition for use of any one of Embodiments A77-A84, wherein the one or more immune checkpoint inhibitors comprise an anti-LAG3 antibody.

Embodiment A86. The pharmaceutical composition for use of Embodiment A85, wherein the anti-LAG3 antibody is GSK2831781.

Embodiment A87. The pharmaceutical composition for use of any one of Embodiments A77-A86, wherein the one or more immune checkpoint inhibitors comprise an anti-TIM3 antibody.

Embodiment A88. The pharmaceutical composition for use of any one of Embodiments A77-A87, wherein the one or more immune checkpoint inhibitors comprise an anti-TIGIT antibody.

Embodiment A89. The pharmaceutical composition for use of Embodiment A88, wherein the anti-TIGIT antibody is vibostolimab (MK-7684), tiragolumab (RG6058), EOS-448, BMS-986207, BGB-A1217, MTIG7192A, AB154, ASP8374, or MK-7684.

Embodiment A90. The pharmaceutical composition for use of any one of Embodiments A77-A89, wherein the cancer is or has become resistant to treatment with at least one immune checkpoint inhibitor.

Embodiment A91. Use of the pharmaceutical composition of any one of Embodiments A19-A23 in the manufacture of a medicament for treating cancer in a subject in need thereof.

Embodiment A92. The use of Embodiment A91, wherein the cancer is a solid tumor.

Embodiment A93. The use of Embodiment A91, wherein the cancer is a hematological cancer.

Embodiment A94. The use of Embodiment A91, wherein the cancer is one or more of cancers listed in Table 1.

Embodiment A95. The use of Embodiment A91, wherein the cancer is of hepatocellular carcinoma, glioblastoma, lung cancer, breast cancer, head and neck cancer, prostate cancer, melanoma, or colorectal cancer.

Embodiment A96. The use of Embodiment A91, wherein the cancer is colorectal cancer, breast cancer, lymphoma, melanoma, kidney cancer, or lung cancer.

Embodiment A97. The use of Embodiment A91, wherein the cancer is an advanced solid tumor, non-small cell lung cancer, or squamous cell carcinoma of head and neck.

Embodiment A98. The use of any one of Embodiments A91-A97, wherein the pharmaceutical composition is to be administered subcutaneously to the subject.

Embodiment A99. The use of Embodiment A98, wherein the pharmaceutical composition is to be administered to the subject according to an intermittent dosing schedule.

Embodiment A100. The use of Embodiment A99, wherein the wherein the pharmaceutical composition is to be administered to the subject twice a week on non-consecutive days.

Embodiment A101. The use of any one of Embodiments A91-A100, wherein the pharmaceutical composition is to be administered with one or more optional therapeutic agents to the subject.

Embodiment A102. The use of Embodiment A101, wherein the one or more optional therapeutic agents comprise one or more immune checkpoint inhibitors.

Embodiment A103. The use of Embodiment A102, wherein the one or more immune checkpoint inhibitors comprise a PD-1 inhibitor, a PD-L1 inhibitor, a CTLA-4 inhibitor, a LAG3 inhibitor, a TIM3 inhibitor, or a TIGIT inhibitor, or a combination thereof.

Embodiment A104. The use of Embodiment A103, wherein the one or more immune checkpoint inhibitors comprise an anti-PD-1 antibody.

Embodiment A105. The use of Embodiment A104, wherein the anti-PD-1 antibody is nivolumab, pembrolizumab, pidilizumab, STI-A1110, (spartalizumab), JTX-4014, sintilimab, MEDI 0680, AGEN2034, BGB-A317, AB122, dostarlimab, PF-06801591, cemiplimab, tislelizumab, toripalimab, camrelizumab, SYM021, JNJ 63723283, HLX10, LZM009, or MGA012.

Embodiment A106. The use of any one of Embodiments A102-A105, wherein the one or more immune checkpoint inhibitors comprise an anti-PD-L1 antibody.

Embodiment A107. The use of Embodiment A106, wherein the anti-PD-L1 antibody is avelumab, atezolizumab, durvalumab, KN035, or STI-A1014.

Embodiment A108. The use of any one of Embodiments A102-A107, wherein the one or more immune checkpoint inhibitors comprise an anti-CTLA-4 antibody.

Embodiment A109. The use of Embodiment A108, wherein the anti-CTLA-4 antibody is ipilimumab or tremelimumab.

Embodiment A110. The use of any one of Embodiments A102-A109, wherein the one or more immune checkpoint inhibitors comprise an anti-LAG3 antibody.

Embodiment A111. The use of Embodiment A110, wherein the anti-LAG3 antibody is GSK2831781.

Embodiment A112. The use of any one of Embodiments A102-A111, wherein the one or more immune checkpoint inhibitors comprise an anti-TIM3 antibody.

Embodiment A113. The use of any one of Embodiments A102-A112, wherein the one or more immune checkpoint inhibitors comprise an anti-TIGIT antibody.

Embodiment A114. The use of Embodiment A113, wherein the anti-TIGIT antibody is vibostolimab (MK-7684), tiragolumab (RG6058), EOS-448, BMS-986207, BGB-A1217, MTIG7192A, AB154, ASP8374, or MK-7684.

Embodiment A115. The use of any one of Embodiments A102-A114, wherein the cancer is or has become resistant to treatment with at least one immune checkpoint inhibitor.

EXAMPLE 1

Lyophilate Screening Studies

Study Number 1

Lyophilates were prepared from the ingredients provided in Table 4. In each case 13.4 mg of Compound 1 is used.

TABLE 4

| ID | Mannitol | PVP K12 | Poloxamer 188 | Tween 80 | $NaH_2PO_4$/ $Na_2HPO_4$ | Additional | Solvent (remaining % is $H_2O$) |
|---|---|---|---|---|---|---|---|
| P3 | 50 mg | 4.0 mg | 2.0 mg | | 2 mg/ 1 mg | | 25% TBA/ 20% EtOH |
| P4 | 50 mg | 4.0 mg | 2.0 mg | | 2 mg/ 1 mg | | 15% TBA/ 30% EtOH |
| P7 | 50 mg | 4.0 mg | 2.0 mg | | 2 mg/ 1 mg | | 15% TBA/ 20% EtOH |
| P8 | 50 mg | 4.0 mg | 2.0 mg | | 2 mg/ 1 mg | | 25% TBA/ 10% EtOH |
| P9 | 50 mg | 4.0 mg | | 4.0 mg | 2 mg/ 1 mg | | 15% TBA/ 30% EtOH |
| P10 | 50 mg | 4.0 mg | 6.0 mg | | 2 mg/ 1 mg | | 15% TBA/ 20% EtOH |

TABLE 4-continued

| ID | Mannitol | PVP K12 | Poloxamer 188 | Tween 80 | $NaH_2PO_4$/ $Na_2HPO_4$ | Additional | Solvent (remaining % is $H_2O$) |
|---|---|---|---|---|---|---|---|
| P11 | 50 mg | 8.0 mg | 2.0 mg | | 2 mg/ 1 mg | | 15% TBA/ 20% EtOH |
| P12 | 50 mg | | 2.0 mg | | 2 mg/ 1 mg | 5.0 mg HPMC | 15% TBA/ 20% EtOH |
| P13 | 50 mg | 4.0 mg | 2.0 mg | | | Replace Phos with Histidine | 15% TBA/ 20% EtOH |
| P14 | 50 mg | 4.0 mg | 2.0 mg | | 2 mg/ mg | 4 mg NaCl | 15% TBA/ 20% EtOH |
| P15 | 50 mg | 4.0 mg | 2.0 mg | | 2 mg/ 1 mg | 20 mg NaCl | 15% TBA/ 20% EtOH |
| P16 | 50 mg | 4.0 mg | 2.0 mg | | 2 mg/ 1 mg | 100 mg HPB-CD | 15% TBA/ 20% EtOH |
| P17 | 50 mg | 4.0 mg | 2.0 mg | | 2 mg/ mg | 44 mg PEG 3350 | 15% TBA/ 20% EtOH |
| P18 | 50 mg | 4.0 mg | | 4.0 mg | 2 mg/ 1 mg | | 15% TBA/ 20% EtOH |
| P19 | 50 mg | 4.0 mg | | 8.0 mg | 2 mg/ 1 mg | | 15% TBA/ 20% EtOH |
| P20 | 50 mg | 4.0 mg | | 4.0 mg | 2 mg/ 1 mg | 5 mg NaCl | 15% TBA/ 20% EtOH |
| P21 | 50 mg | 4.0 mg | | 4.0 mg | 2 mg/ 1 mg | | 50% TBA/ 5% EtOH |

The lyophilized cakes of P3, P4, P7, P8, and P9 had variable appearance with P7 giving the best formed cake. See FIG. 1.

The results of the screening performance of the lyophilized cakes are provided in Table 5 and Table 6. The solvent used to suspend the lyophilates in Table 6 was 1 mL of water for injection (WFI).

TABLE 5

| ID | Solvent for Suspension | Time* (min:sec) | Comments |
|---|---|---|---|
| P3 | 1 mL WFI | 6:20 | Separates in syringe. |
| P4 | 1 mL WFI | 3:30 | Separates in syringe. |
| P7 | 1 mL WFI | 5:10 | Separates in syringe. |
| P8 | 1 mL WFI | 5:50 | Separates in syringe |
| P9 | 1 mL WFI | 1:30 | Less grainy texture, more homogeneous appearance in the syringe. Slower to separate than 8. |
| P9 | 1 mL of 0.4% polysorbate 80 in WFI | 2:30 | Remains uniform |
| P4 | 1 mL of 0.4% polysorbate 80 in WFI | 3:50 | Some separation, but better than with water alone. |

*Time includes time for suspension, plus 1 additional minute.

TABLE 6

| ID | Time | Comments |
|---|---|---|
| P10 | 1.25 + 1 min | Slight separation after 11 min; more considerable flocculation after 1 h |
| P11 | 2 + 1 min | 1 min to separation and flocculation; it settled to the bottom of the syringe |
| P12 | 7 + 1 min | 9.5 min to slight separation at top of the syringe; after that there was a continuous separation and settling over time |
| P13 | 3 + 1 min | 30 seconds to separation; settling followed |
| P14 | 1 + 1 min | Less than 1 min to separation and settling in syringe. |
| P15 | 0.5 + 1 min | 30 seconds to see separation; settling followed |

TABLE 6-continued

| ID | Time | Comments |
|---|---|---|
| P16 | 0.5 + 1 min | Gradual separation within 30 seconds; had more translucent appearance. The separated components seemed to rise rather than settle. Clearly separated by 15 min. |
| P17 | 1.75 + 1 min | Within 30 seconds saw agglomerates and separation, but did not settle. |
| P18 | 0.66 + 1 min | Separation was noticeable with 13 mins. |
| P19 | 0.5 + 1 min | Some separation after 10 min; it settled to the bottom of syringe. |
| P20 | 0.5 + 1 min | By 10 min, separation and settling in the syringe. |
| P21 | 0.5 + 1 min | Separation was noticeable after 15 min in the syringe. |

Study Number 2

Lyophilates comprising Compound 1 and other ingredients are provided in Table 7. In each case 15 mg/mL of Compound 1 is used.

TABLE 7

| ID and Ingredients | Cake Description | Suspension with Water | Suspension with 1% Recombinant Albumin |
|---|---|---|---|
| E1 - 30 mg/mL mannitol; 1.7 mg/mL poloxamer 188; 5.6 mg/mL NaCMC | Nicely Formed | Suspension: 1 min, dirty wall, small lumps Stability: Flocculation in 1 min; settle in 5 min | Suspension: 1 min Stability: >40 min |
| E2 - 30 mg/mL mannitol; 1.7 mg/mL poloxamer 188 | | Suspension: 30 sec; dirty wall; uniform appearance Stability: Stable 15 min | Suspension: 1.3 min Stability: 24 min |
| E5 - 30 mg/mL mannitol; 6.8 mg/mL poloxamer 188 | | Suspension: 20 sec; D50 15.9 Stability: Stable 2 min; 40 sec to flocs | Suspension: 20 sec; dirty wall; D50 16.2 Stability: 5 min to flocs; 10 min to settle |
| E6 - 30 mg/mL mannitol; 6.8 mg/mL poloxamer 188; 5.6 mg/mL NaCMC | Nicely Formed | Suspension: 5 min; hard to draw up; D50 44.4 Stability: >15 min | Suspension: 90 sec; dirty wall; D50 21.7 Stability: >15 min |
| E7 - 30 mg/mL mannitol; 1.7 mg/mL poloxamer 188; 5.6 mg/mL NaCMC, 10 mM histidine | Nicely Formed | Suspension: 2 min; hard to draw up; dirty wall; D50 43.7 Stability: >15 min | Suspension: 2 min; dirty wall; D50 28.0 Stability: >15 min |
| E8 - 30 mg/mL mannitol; 1.7 mg/mL poloxamer 188; 5.6 mg/mL NaCMC; 10 mg/mL lecithin PL90G | Nicely Formed | Suspension: 30 sec; D50 13.2 Stability: >15 min; very uniform | Suspension: 1.25 min; D50 25.3 Stability: >15 min |
| E9 - 30 mg/mL mannitol; 1.7 mg/mL poloxamer 188; 10 mg/mL lecithin PL90G | | Suspension: 15 min; D50 25.1 Stability: 2 min to flocs; 15 min to settle | Suspension: 15 sec; D50 29.9 Stability: >15 min |

EXAMPLE 2

Preparation of Pharmaceutical Composition Comprising Compound 1 in Unit Dosage Form for Subcutaneous Administration to a Subject The amounts Compound 1, mannitol, sodium carboxymethyl cellulose, poloxamer 188, histidine, and other ingredients for preparing lyophilates L1, L2, and L3 are given in Table 8.

TABLE 8

| | Lyophilate ID | | |
|---|---|---|---|
| Ingredient | L1 Amount (g) | L2 Amount (g) | L3 Amount (g) |
| Compound 1 (g) | 0.06750 | 0.06750 | 0.0625 |
| Mannitol (g) | 0.135 | 0.135 | 0.125 |
| sodium carboxymethyl cellulose* (g) | 0.0252 | 0.009 | 0.00833 |
| poloxamer 188, NF*** | 0.00765 | 0.00765 | 0.00708 |
| soy lecithin** | 0.0450 | 0.0450 | 0.04167 |
| Histidine (g) | 0.00388 | 0.00388 | 0.00431 |
| Ethanol (g) | 0.355 | 0.355 | 0.3945 |
| Ethanol (L) (d = 0.789) | 0.000450 | 0.000450 | 0.0005 |
| t-Butanol (g) | 1.299 | 1.2285 | 1.365 |
| t-Butanol (L) (d = 0.780) | 0.00158 | 0.00158 | 0.00175 |
| QS to (with WFI) (L) | 0.0045 | 0.0045 | 0.0050 |
| 1M HCl (titrate to pH 6.6-6.8) (mL) | 0.0042 | 0.00416 | 0.00462 |

*Sodium CMC 7LF (Ashland Part Number 891158);
**Lipoid S 100;
***Spectrum Chemical MFG Corp. Product Code P1169

1. Dissolution to Give a Pre-Lyophilization Solution:

First, mannitol, sodium carboxymethyl cellulose, poloxamer 188, and histidine are dissolved in water at 40° C. After dissolution the solution may be cooled without precipitation to 25° C.

Second, the solution is titrated to pH 6.6-6.8 (target 6.7) using 1 M HCl.

Third, the solution is mixed with warm t-butanol and ethanol.

Fourth, the soy lecithin is dissolved in the solution at 30° C.

Fifth, Compound 1 is fully dissolved in the solution at 30° C. (this may take several hours). The solution is, optionally, protected from light.

Sixth, the temperature is reduced to 20-25° C.

Seventh, the solution is brought to the correct mass (or volume) using the target QS value, adding room temperature WFI until the target is reached.

After 12 hours at room temperature, the L2 pre-lyophilization solution contained precipitated solids that could be re-dissolved by mixing at 30° C.

2. Sterile Filtration

The drug product solution of step 1 was sterile filtered using redundant 1) Millipore Polysep II prefilter and 2) redundant Millipore Durapore 0.22 micron capsule filters. The pressure should be maintained at 20 PSI or less.

Precipitation occurred during filtration of the L2 pre-lyophilization solution.

3. Lyophilization

The initial shelf temperature is room temperature. The shelf temperature is decreased to −40° C., and the pressure is dropped to 45 mTorr. This condition is held for 44.5 h. Then, the shelf temperature is ramped up to 0° C. over 5 hours and held at that temperature for 12 hours. Then, the shelf temperature is ramped up to 35° C. over 1 h and held at that temperature for 28 hours. The shelf temperature is ramped back to room temperature over 1 h prior to nitrogen equilibration and then insertion of stoppers. The freezing/drying is accomplished according to one of the following programs.

| Program 1 | | | | |
|---|---|---|---|---|
| Step | Program Time (h) | Step Time (h) | Shelf Temperature (° C.) | Vacuum (mTorr) |
| Freezing | 0 to 6.5 | 6.5 | −40° C. | Ambient Pressure |
| −40° C. Hold | 6.5 to 51 h | 44.5 | −40° C. | 45 |
| Ramp to 0° C. | 51 to 56 h | 5 | Ramp to 0° C. | 45 |
| 0° C. Hold | 56 to 68 h | 12 | 0° C. | 45 |
| Ramp to 35° C. | 68 to 69 h | 1 | Ramp to 35° C. | 45 |
| 35° C. Hold | 69 to 97 h | 28 | 35° C. | 45 |
| Ramp to RT and Nitrogen Fill | 97 to 98 h | 1 | Ramp to RT and Nitrogen Fill | Ambient Pressure Following Nitrogen Fill |

| Program 2 | | | | |
|---|---|---|---|---|
| Step | Program Time (h) | Step Time (h) | Shelf Temperature (° C.) | Vacuum (mTorr) |
| Freezing | 0 to 6.5 | 6.5 | −40° C. | Ambient Pressure |
| −40° C. Hold | 6.5 to 51 h | 44.5 | −40° C. | 45 |
| Ramp to 0° C. | 51 to 56 h | 5 | Ramp to 0° C. | 45 |
| 0° C. Hold | 56 to 68 h | 12 | 0° C. | 45 |
| Ramp to 35° C | 68 to 69 h | 1.17 | Ramp to 35° C. | 45 |
| 35° C. Hold | 69 to 97 h | 28 | 35° C. | 45 |
| Ramp to RT and Nitrogen Fill | 97 to 98 h | 1 | Ramp to RT and Nitrogen Fill | Ambient Pressure Following Nitrogen Fill |

The chemical purity of Compound 1 in the lyophilate thus obtained is greater than or equal to 9700.

4. Preparation of a Pharmaceutical Composition

For L1 and L3, 2.5 mL of WFI is added to the lyophilate, and the container, e.g., a vial, is shaken to give a suspension. For L2, 2.25 mL of WFI is added to the lyophilate, and the container, e.g., a vial, is shaken to give a suspension.

EXAMPLE 3

Lyophilate Optimization Studies

Study Number 1

The compounding ingredients used to prepare lyophilates L4-L11 on a 100 mL scale (100 mL of each formulation was prepared) are provided in Table 9, and the results observed for these lyophilates are provided in Table 10.

| | Lyophilate ID | | | | | | | |
|---|---|---|---|---|---|---|---|---|
| Ingredient | L4 Amount | L5 Amount | L6 Amount | L7 Amount | L8 Amount | L9 Amount | L10 Amount | L11 Amount |
| Compound 1 (g) | 1.5 | 1.5 | 1.5 | 1.5 | 1.5 | 1.5 | 1.5 | 1.5 |
| Mannitol (g) | 3 | 3 | 3 | 5 | 3 | | | |
| PVP K12 | | | | | 0.5 | | | |
| Sucrose (g) | | | | | | 10 | | |
| Glucose (g) | | | | | | | 5 | |
| Trehalose dehydrate (g) | | | | | | | | 5 |
| Sodium CMC (g) | 0.28 | 0.12 | 0.06 | 0.06 | 0.06 | 0.06 | 0.06 | 0.06 |
| Poloxamer 188 (g) | 0.17 | 0.17 | 0.17 | 0.17 | 0.17 | 0.17 | 0.17 | 0.17 |
| Histidine (g) | 0.0862 | 0.0862 | 0.0862 | 0.0862 | 0.0862 | 0.0862 | 0.0862 | 0.0862 |
| Soy lecithin (g) | 1 | 1 | 1 | 1 | 1 | 1 | 1 | 1 |
| Ethanol (g) | 7.9 | 7.9 | 7.9 | 7.9 | 7.9 | 7.9 | 7.9 | 7.9 |
| Ethanol (mL) | 10 | 10 | 10 | 10 | 10 | 10 | 10 | 10 |
| t-butanol (g) | 27.6 | 27.6 | 27.6 | 27.6 | 27.6 | 27.6 | 27.6 | 27.6 |
| t-butanol (mL) | 35 | 35 | 35 | 35 | 35 | 35 | 35 | 35 |
| QS to (with WFI) (mL) | 100 | 100 | 100 | 100 | 100 | 100 | 100 | 100 |

TABLE 10

| | | Lyophilate ID | | | | | | | |
|---|---|---|---|---|---|---|---|---|---|
| | | L4 | L5 | L6 | L7 | L8 | L9 | L10 | L11 |
| Cake appearance | | Good | Crack in middle | Crack in middle | Crack in middle | Crack in middle | Good | Good | Good |
| Suspension time | | <30 s | <30 s | <30 s | <30 s | <30 s | <30 s | <30 s | <30 s |
| Suspension appearance at T0 | | Uniform | Uniform | Uniform | Uniform | Uniform | Uniform | Uniform | Uniform |
| Suspension appearance at 4 h | | Uniform | Uniform | Settle | Uniform | Settle | Uniform | Uniform | Uniform |
| PSD (μm) | $D_{10}$ | 11.7 | 9.8 | 13.5 | 13.5 | 4.4 | 8.9 | 5.4 | 3.9 |
| | $D_{50}$ | 17.7 | 14.3 | 25.3 | 25.3 | 10.3 | 14.4 | 12.1 | 7.7 |
| | $D_{90}$ | 26.8 | 20.6 | 40.9 | 40.9 | 21.2 | 23.3 | 25.8 | 17.6 |
| PSD at 4 h (μm) | $D_{10}$ | 5.0 | 5.7 | 6.2 | 6.1 | 3.6 | 5.3 | 4.3 | 3.5 |
| | $D_{50}$ | 12.9 | 15.2 | 17.4 | 17.3 | 8.8 | 13.6 | 7.2 | 6.2 |
| | $D_{90}$ | 45.6 | 46.3 | 46.4 | 46.0 | 23.2 | 40.0 | 11.7 | 10.7 |

TABLE 10-continued

| | Lyophilate ID | | | | | | | |
|---|---|---|---|---|---|---|---|---|
| | L4 | L5 | L6 | L7 | L8 | L9 | L10 | L11 |
| Re-suspend-ability | Easy | Easy | Easy | Easy | Easy | Easy | Easy | Easy |
| Micro-scopic image T0 | Uni-form | Uni-form | Uni-form | Uni-form | Uni-form | Uni-form | Uni-form | Uni-form |

Study Number 2

The compounding ingredients used to prepare lyophilates L12-L17 on a 100 mL scale (100 mL of each formulation was prepared) are provided in Table 11, and the results observed for these lyophilates are provided in Table 12 and Table 13.

TABLE 11

| | Formulation Code | | | | | | |
|---|---|---|---|---|---|---|---|
| Ingredients | L12 Amt | L13 Amt | L14 Amt | L18 Amt | L15 Amt | L16 Amt | L17 Amt |
| Compound 1 (g) | 1.5 | 1.5 | 1.5 | 1.5 | 1.5 | 1.5 | 1.5 |
| Sodium CMC 7L2P (g) | 0.56 | 0.28 | 0.14 | | | | |
| Sodium CMC 7LF (g) | | | | 0.28 | 0.25 | 0.20 | 0.18 |
| Poloxamer 188 (g) | 0.17 | 0.17 | 0.17 | 0.17 | 0.17 | 0.17 | 0.17 |
| Histidine (g) | 0.0862 | 0.0862 | 0.0862 | 0.0862 | 0.0862 | 0.0862 | 0.0862 |
| Soy lecithin (g) | 1 | 1 | 1 | 1 | 1 | 1 | 1 |
| Ethanol (g) | 7.9 | 7.9 | 7.9 | 7.9 | 7.9 | 7.9 | 7.9 |
| Ethanol (mL) | 10 | 10 | 10 | 10 | 10 | 10 | 10 |
| t-butanol (g) | 27.6 | 27.6 | 27.6 | 27.6 | 27.6 | 27.6 | 27.6 |
| t-butanol (mL) | 35 | 35 | 35 | 35 | 35 | 35 | 35 |
| 1M HCl (pH 6.6 to 6.8 | 6.7 | 6.7 | 6.7 | 6.7 | 6.7 | 6.7 | 6.7 |
| QS to (with WFI) (mL) | 100 | 100 | 100 | 100 | 100 | 100 | 100 |

TABLE 12

| | | Formulation Code | | | | | | |
|---|---|---|---|---|---|---|---|---|
| | | L12 | L13 | L14 | L18 | L15 | L16 | L17 |
| Cake appear-ance | | Good | Good | Crack in mid-dle | Good | Good | Good | Crack in mid-dle |
| Recon time | | 60-120 s | <30 s | <30 s | 60-120 s | <30 s | <30 s | <30 s |
| Sus-pension appear-ance at T0 | | Uni-form | Uni-form | Uni-form | Uni-form | Uni-form | Uni-form | Uni-form |
| Sus-pension appear-ance at 4 h | | Uni-form | Uni-form | Uni-form | ND | Uni-form | Uni-form | Uni-form |
| PSD (μm) | D10 | 3.8 | 3.6 | 3.8 | ND | 4.1 | 3.9 | 3.8 |
| | D50 | 8.3 | 7.0 | 8.3 | ND | 9.3 | 7.9 | 7.4 |
| | D90 | 18.6 | 13.9 | 21.3 | ND | 19.8 | 16.9 | 14.5 |
| PSD at 4 h (μm) | D10 | 4.4 | 4.1 | 3.9 | ND | 4.0 | 4.0 | 4.4 |
| | D50 | 6.8 | 6.6 | 7.7 | ND | 6.6 | 6.9 | 6.9 |
| | D90 | 10.4 | 10.6 | 14.8 | ND | 10.5 | 11.5 | 10.7 |
| Re-suspend-ability | | Easy | Easy | Easy | ND | Easy | Easy | Easy |
| Micro-scopic image T0 | | Uni-form | Uni-form | Uni-form | ND | Uni-form | Uni-form | Uni-form |

TABLE 13

| | Formulation Code | | | | | | | |
|---|---|---|---|---|---|---|---|---|
| | L12 | L13 | L14 | L18 | L15 | L16 | L17 | Water |
| Force (N) | 15.0 | 10.0 | 7.8 | 10.5 | 9.5 | 9.0 | 8.5 | 2.5 |
| Syringe ID (mm) | 8.1 | 8.1 | 8.1 | 8.1 | 8.1 | 8.1 | 8.1 | 8.1 |
| Area ($mm^2$) | 51.2 | 51.2 | 51.2 | 51.2 | 51.2 | 51.2 | 51.2 | 51.2 |
| Subjective Assessment by Lab Technician in Manual Injection | mild | mild | easy | mild | mild | easy | easy | easy |

EXAMPLE 4

Suspension Studies

Lyophilate L2, see EXAMPLE 2, was suspended in 1.5, 2.0, 2.25, and 2.5 mL of WFI. The results of testing of this pharmaceutical composition are provided in Table 14.

TABLE 14

| | WFI Volume | | | | |
|---|---|---|---|---|---|
| | 1.5 mL | 2.0 mL | 2.25 mL | 2.5 mL # 1 | 2.5 mL # 2 |
| Cake appearance | | | Good | | |
| Recon time | <30 s | <30 s | <30 s | <30 s | <30 s |
| Measured Volume | N/A* | N/A* | 2.28 mL | 2.54 mL | 2.54 mL |

TABLE 14-continued

| | | WFI Volume | | | | |
|---|---|---|---|---|---|---|
| | | 1.5 mL | 2.0 mL | 2.25 mL | 2.5 mL # 1 | 2.5 mL # 2 |
| Suspension appearance at T0 | | Uniform | Uniform | Uniform | Uniform | Uniform |
| Suspension appearance at 4 h | | Thick/ Paste-like | Thick/ Paste-like | Uniform | Uniform | Uniform |
| PSD (μm) | $D_{10}$ | N/A* | N/A* | 4.53 | 5.48 | 5.57 |
| | $D_{50}$ | | | 12.2 | 16.0 | 9.33 |
| | $D_{90}$ | | | 30.2 | 41.6 | 15.8 |
| PSD at 4 h (μm) | $D_{10}$ | | | 4.56 | 4.20 | 4.50 |
| | $D_{50}$ | | | 8.82 | 9.03 | 8.20 |
| | $D_{90}$ | | | 18.2 | 26.9 | 14.5 |
| Re-suspendability | | N/A* | N/A* | Easy | Easy | Easy |
| Microscopic image T0 | | Uniform | Uniform | Uniform | Uniform | Uniform |
| Moisture content of cake | | | | 2.09% | | |
| % HPLC (1 mL through syringe) | | N/A | N/A | 94.2 | 102.6 | N/A |
| % HPLC (Full dissolution of cake) | | | | 103.9 | | |

*Suspension became thick about 15-20 minutes after reconstitution, could not perform PSD test Injection force was tested using the Instron instrument (BD 3 mL syringe, 27G1/2 inch needle, injection rate 1 mm/s). The results are provided in Table 15

TABLE 15

| WFI Volume | 2.25 mL | 2.5 mL |
|---|---|---|
| Force (N) | 6.8 | 5.6 |
| Syringe ID (mm) | 8.1 | 8.1 |
| Area (mm2) | 51.2 | 51.2 |
| Manual injectability | mild | easy |

EXAMPLE 5

Subcutaneous Pharmaceutical Composition Studies

To assess the stability of the L1 pharmaceutical composition (also referred to as E8h) prepared according to EXAMPLE 2 at 2-8° C. over 5 days, a study was conducted to determine the chemical and colloidal stability for two concentrations—suspension of the lyophilate with 2.5 mL WFI and 10.0 mL WFI. At each concentration, 5 vials were used. All were suspended time zero and were subsequently assayed for their properties following varying hold times. Data on the suspension (Recon) time and appearance is summarized below in Table 16.

TABLE 16

| Sample | Test | T0 | 1 h | 24 h | 3 d | 5 d |
|---|---|---|---|---|---|---|
| 2.5 mL recon | Recon time | 60 s | 83 s | 83 s | 58 s | 77 s |
| 10 mL recon | | 85 s | 93 s | 81 s | 101 s | 98 s |
| 2.5 recon | Appearance (Lyo) | Off-white uniform suspension, Clean wall | Settled, easy to re-suspend. Off-white uniform suspension, clean wall | No change | No T change | Big particles observed, not uniform and dirty wall |
| 10 mL recon | | Off-white uniform suspension, Clean wall | Settled, easy to re-suspend; off-white uniform suspension, Clean wall | No change | No change | Big particles observed, not uniform and dirty wall |

Over the first 3 days, the vials could easily be resuspended (shaken again to achieve a uniform drug product), but on Day 5, the appearance was no longer uniform.

The particle size distribution (PSD) was measured over the course of the study, with each test vial suspended on Day 0 and held until it was resuspended and sampled at its scheduled test time. Data on the PSD is summarized in Table 17.

TABLE 17

| Sample | Test | T0 | 1 h | 24 h | 3 d | 5 d |
|---|---|---|---|---|---|---|
| 2.5 mL recon | D10 (v, μm) | 5.9 | 5.6 | 5.8 | 6.2 | 7.9 |
| | D50 (v, μm) | 13.0 | 12.9 | 13.3 | 15.0 | 29.1 |
| | D90 (v, μm) | 24.7 | 24.2 | 25.4 | 28.9 | 66.6 |
| 10 mL recon | D10 (v, μm) | 7.1 | 7.0 | 7.0 | 8.7 | 5.3 |
| | D50 (v, μm) | 21.8 | 22.3 | 19.7 | 26.0 | 25.8 |
| | D90 (v, μm) | 46.9 | 48.9 | 47.0 | 56.1 | 55.8 |

The PSD is uniform through Day 3, but on Day 5 it has a shift upward. No change in impurities as measured by HPLC was seen over the 5-day study. A decrease in Compound 1 was seen on Day 5 in the 10 mL resuspension. This data is summarized in the table of percent label claim as shown in Table 18.

TABLE 18

| Sample | Test | T0 | 1 h | 24 h | 3 d | 5 d |
|---|---|---|---|---|---|---|
| 2.5 mL recon | % | 92 | 96 | 94 | 96 | 96 |
| 10 mL recon | LC | 97 | 98 | 98 | 97 | 91 |

Following resuspension, the accuracy of delivery of Compound 1 from the pharmaceutical composition using a 0.5 mL tuberculin syringe was tested. 150 microliters of the suspension was drawn up in the syringe and injected into a volumetric flask for assay. Repeated trials were conducted using fresh syringes in order to confirm the relative standard deviation (RSD) with HPLC assays conducted in duplicate. The data is tabulated in the tables below.

| # of repetition | Same Name | Peak Area | HPLC Assay (mg/mL) |
|---|---|---|---|
| 1 | Accuracy-10-1 | 425.4 | 0.100 |
| | Accuracy-10-1 | 427.6 | 0.100 |
| 2 | Accuracy-10-2 | 412.8 | 0.097 |
| | Accuracy-10-2 | 410.3 | 0.096 |
| 3 | Accuracy-10-3 | 422.8 | 0.099 |
| | Accuracy-10-3 | 422.1 | 0.099 |
| 4 | Accuracy-10-4 | 417.5 | 0.098 |
| | Accuracy-10-4 | 416.8 | 0.098 |
| 5 | Accuracy-10-5 | 417.8 | 0.098 |
| | Accuracy-10-5 | 416.9 | 0.098 |
| Avg. | | 419.0 | 0.098 |
| % RSD | | 1.3 | 1.3 |

Average % LC of E8h with 10 mL reconstruction

| Sample | API amount by assay (mg) | Label claimed API amount (mg) | % LC |
|---|---|---|---|
| E8h 10 mL recon | 67.0 | 67.5 | 99.2 |

Precision and accuracy of E8h with 2.5 mL reconstruction

| # of repetition | Same Name | Peak Area | HPLC Assay (mg/mL) |
|---|---|---|---|
| 1 | Accuracy-2.5-1 | 1549.2 | 0.362 |
| | Accuracy-2.5-1 | 1544.0 | 0.361 |
| 2 | Accuracy-2.5-2 | 1573.2 | 0.368 |
| | Accuracy-2.5-2 | 1565.3 | 0.366 |
| 3 | Accuracy-2.5-3 | 1576.7 | 0.369 |
| | Accuracy-2.5-3 | 1569.5 | 0.367 |
| 4 | Accuracy-2.5-4 | 1548.8 | 0.362 |
| | Accuracy-2.5-4 | 1544.3 | 0.361 |
| 5 | Accuracy-2.5-5 | 1537.9 | 0.356 |
| | Accuracy-2.5-5 | 1525.1 | 0.357 |
| Avg. | | 15553.4 | 0.363 |
| % RSD | | 1.1 | 1.1 |

Average % LC of E8 with 2.5 mL reconstruction

| Sample | API amount by assay (mg) | Label claimed API amount (mg) | % LC |
|---|---|---|---|
| E8h 2.5 mL recon | 66.9 | 67.5 | 99.1 |

EXAMPLE 6

In-Use Studies with the L3 Pharmaceutical Composition

In this study, mock injections were delivered at doses of 3, 6, and 50 mg in order to assess stability and absorption of Compound 1 during resuspension and administration of the L3 pharmaceutical composition. Assays were performed at 0, 4, and 24 hours. The results are provided in Table 19, Table 20, Table 21, and Table 22.

TABLE 19

| Vial Stability Study | | |
|---|---|---|
| ASSAY | | ASSAY RESULT |
| Reconstitution Time | | 30 s |
| Suspension appearance | $T_0$ | Uniform |
| | $T_{4\ h}$ | Slight phase separation |
| | $T_{24\ h}$ | Phase separation |
| PSD at $T_0$ (μm) | $D_{10}$ | 9.10 |
| | $D_{50}$ | 19.6 |
| | $D_{90}$ | 36.3 |
| PSD at $T_{4\ h}$ (μm) | $D_{10}$ | 4.13 |
| | $D_{50}$ | 6.50 |
| | $D_{90}$ | 10.0 |
| PSD at $T_{24\ h}$ (μm) | $D_{10}$ | 3.76 |
| | $D_{50}$ | 6.63 |
| | $D_{90}$ | 11.4 |
| Re-suspendability | $T_0$ | N/A |
| | $T_{4\ h}$ | 5 s |
| | $T_{24\ h}$ | 5 s |
| % Label Claim | $T_0$ | 104.1 |
| | $T_{4\ h}$ | 104.8 |
| | $T_{24\ h}$ | 104.7 |

TABLE 19-continued

| Vial Stability Study | | |
|---|---|---|
| ASSAY | | ASSAY RESULT |
| Impurities | $T_0$ | ND* |
| | $T_{4\ h}$ | ND* |
| | $T_{24\ h}$ | ND* |

*Below quantification limit 2.48 μg/mL

TABLE 20

| Instron Force of Injection Measurements | | | |
|---|---|---|---|
| | $T_0$ | $T_{4\ hr}$ | $T_{24\ hr}$ |
| Force (N)* | 5.5 | 6.5 | 8.0 |

*Syringe ID: 8.1 mm; Syringe Area: 51.2 mm$^2$

TABLE 21

| Syringe Stability Study (BD 3 mL syringe, 27G1/2 inch needle, injection rate 1 mm/s) | | |
|---|---|---|
| ASSAY | | RESULT |
| Suspension appearance | $T_0$ | Uniform |
| | $T_{1\ h}$ | Uniform |
| | $T_{2\ h}$ | Slight phase separation |
| Re-suspendability | $T_0$ | N/A |
| | $T_{1\ h}$ | 5 s |
| | $T_{2\ h}$ | 5 s |
| % Label Claim | $T_0$ | 98.8 |
| | $T_{1\ h}$ | 100.1 |
| | $T_{2\ h}$ | 99.1 |
| Impurities | $T_0$ | ND |
| | $T_{1\ h}$ | ND |
| | $T_{2\ h}$ | ND |

TABLE 22

| Syringe Delivery Mock Injection Study | | | |
|---|---|---|---|
| INJECTION AMOUNT/ INJECTION NUMBER | | Compound 1 delivered (mg) - HPLC | % Theoretical Compound 1 delivery |
| 3 mg (0.12 mL) | #1 | 3.3 | 110 |
| | #2 | 3.2 | 106 |
| | #3 | 3.3 | 110 |
| 6 mg (0.24 mL) | #1 | 5.9 | 98 |
| | #2 | 5.9 | 98 |
| | #3 | 6.2 | 104 |

EXAMPLE 7

Pharmacokinetic Studies

The L1 and L2 pharmaceutical compositions described in EXAMPLE 2 were administered to dogs via subcutaneous (SC) injection at 0.83 mg/kg. Blood samples were collected from all animals via the saphenous vein or cephalic vein at pre-dose, 0.25, 0.5, 1, 2, 4, 6, 8, 12, 24, 36, 48, 60 and 72 hours post-dose in the SC group into test tubes containing potassium ethylenediaminotetraacetic acid (K2EDTA). Plasma was separated from the blood by centrifugation at 4° C. and stored at −80° C. until analysis. Compound 1 and DON concentration in plasma was quantified using a liquid chromatography with tandem mass spectrometry (LC-MS/MS) method.

Following single SC dosing of the L1 pharmaceutical composition at 0.83 mg/kg in dogs, the mean peak plasma concentration ($C_{max}$=120±33.5 nM) of Compound 1 was reached at 0.500 hours (median $T_{max}$) post dose. The mean terminal $T_{1/2}$ was 8.71±3.90 hours. The $AUC_{last}$ and $AUC_{inf}$ were calculated to be 1270±469 and 1430±468 hr*nM, respectively. The $MRT_{last}$ and $MRT_{INF}$ was 9.31±2.30 hr and 13.0±4.98 hr, respectively.

Following single SC dosing of the L2 pharmaceutical composition at 0.83 mg/kg in dogs, the mean peak plasma concentration ($C_{max}$=70.7±18.9 nM) of Compound 1 was reached at 4.00 hours (median $T_{max}$) post dose. The mean terminal $T_{1/2}$ was 12.1±12.3 hours. The $AUC_{last}$ and $AUC_{inf}$ were calculated to be 759±230 and 1030±478 hr*nM, respectively. The $MRT_{last}$ and $MRT_{INF}$ was 7.61±2.09 hr and 17.0±16.5 hr, respectively.

In contrast, following single SC dosing of a solution formulation of Compound 1 (vehicle: 5% ethanol, 45% PEG 400, and 0.2% Poloxamer 188 in phosphate buffer) at 0.15 mg/kg in dogs, the mean peak plasma concentration ($C_{max}$=170 nM) Compound 1 in dogs was reached at 0.50 hour (median $T_{max}$) post dose. The mean terminal $T_{1/2}$ was 0.71 h. The $AUC_{last}$ was calculated to be 0.249 hr*μM.

It is to be understood that the foregoing described embodiments and exemplifications are not intended to be limiting in any respect to the scope of the disclosure, and that the claims presented herein are intended to encompass all embodiments and exemplifications whether or not explicitly presented herein.

All patents and publications cited herein are fully incorporated by reference in their entirety.

What is claimed is:

1. A lyophilate comprising about 20% wt/wt to about 45% wt/wt of (S)-isopropyl 2-((S)-2-acetamido-3-(1H-indol-3-yl) propanamido)-6-diazo-5-oxohexanoate, about 35% wt/wt to about 55% wt/wt of a bulking agent, and about 1% wt/wt to about 10% wt/wt of a cellulose-based suspension modulator.

2. The lyophilate of claim 1 further comprising about 1% wt/wt to about 5% wt/wt of a poloxamer-based suspension modulator.

3. The lyophilate of claim 1 further comprising about 10% wt/wt to about 20% wt/wt of a lecithin-based suspension modulator.

4. The lyophilate of claim 1 further comprising about 0.5% wt/wt to about 2.5% wt/wt of a buffer.

5. The lyophilate of claim 1 comprising:

(i) about 20% wt/wt to about 30% wt/wt of(S)-isopropyl 2-((S)-2-acetamido-3-(1H-indol-3-yl) propanamido)-6-diazo-5-oxohexanoate;

(ii) about 45% wt/wt to about 55% wt/wt of a bulking agent;

(iii) about 1% wt/wt to about 9% wt/wt of a cellulose-based suspension modulator;

(iv) about 1% wt/wt to about 4% wt/wt of a poloxamer-based suspension modulator;

(v) about 12% wt/wt to about 20% wt/wt of a lecithin-based suspension modulator; and (vi) about 1% wt/wt to about 2% wt/wt of a buffer.

6. The lyophilate of claim 1 comprising:

(i) about 62.5 mg of (S)-isopropyl 2-((S)-2-acetamido-3-(1H-indol-3-yl) propanamido)-6-diazo-5-oxohexanoate;

(ii) about 125 mg of mannitol;

(iii) about 8.3 mg of sodium carboxymethyl cellulose;

(iv) about 7.1 mg of Poloxamer 188, NF;

(v) about 41.7 mg of soy lecithin; and (vi) about 4.3 mg of histidine.

7. A pharmaceutical composition comprising the lyophilate of claim 1, wherein the lyophilate is suspended in a pharmaceutically acceptable carrier.

8. The pharmaceutical composition of claim 7, wherein the (S)-2-((S)-2-acetamido-3-(1H-indol-3-yl)propanamido)-6-diazo-5-oxohexanoate isopropyl concentration is about 20 mg/mL to about 60 mg/mL.

9. The pharmaceutical composition of claim 7, wherein the average particle size distribution of (S)-isopropyl 2-((S)-2-acetamido-3-(1H-indol-3-y1)propanamido)-6-diazo-5-oxohexanoate in the suspension is about 1 μm to about 30 μm.

10. A method for treating cancer in a subject in need thereof, the method comprising administering a therapeutically effective amount of the pharmaceutical composition of claim 7 to the subject.

11. The method of claim 10, wherein the cancer is one or more of adrenal cancer, acinic cell carcinoma, acoustic neuroma, acral lentigious melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological cancer, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogeous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, preimary primary peritoneal cancer, prostate cancer, pancreatic cancer, pharyngeal cancer, pseudomyxoma periotonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, or Wilms' tumor.

12. The method of claim 10, wherein the cancer is hepatocellular carcinoma, glioblastoma, lung cancer, breast cancer, head and neck cancer, prostate cancer, melanoma, or colorectal cancer.

13. The method of claim 10, wherein the pharmaceutical composition is administered subcutaneously to the subject.

14. The method of claim 13, wherein the pharmaceutical composition is administered to the subject according to an intermittent dosing schedule.

15. The method of claim 10 further comprising administering one or more optional therapeutic agents to the subject.

16. The method of claim 15, wherein the one or more optional therapeutic agents comprise one or more immune checkpoint inhibitors.

17. A kit comprising the lyophilate of claim 1 packaged as single unit dose in a container.

18. The kit of claim 17 further comprising instructions for suspending the lyophilate in a solvent to give a pharmaceutical composition.

19. A method of making the lyophilate of claim 1, the method comprising:

(i preparing a pre-lyophilization solution comprising (S)-isopropyl 2-((S)-2-acetamido-3-(1H-indol-3-yl) propanamido)-6-diazo-5-oxohexanoate, a bulking agent, a cellulose-based suspension modulator, and water;

(ii) cooling the pre-lyophilization solution until it is frozen or partially frozen; and (iii) applying a vacuum to the frozen or partially frozen pre-lyophilization solution to give the lyophilate.

* * * * *